(12) United States Patent
Kozuka et al.

(10) Patent No.: US 7,542,659 B2
(45) Date of Patent: Jun. 2, 2009

(54) RECORDING MEDIUM, PLAYBACK DEVICE, RECORDING METHOD, PLAYBACK METHOD, AND COMPUTER PROGRAM

(75) Inventors: Masayuki Kozuka, Neyagawa (JP); Tomoyuki Okada, Nara (JP); Tomoki Ogawa, Amagasaki (JP)

(73) Assignee: Panasonic Corporation, Osaka (JP)

( * ) Notice: Subject to any disclaimer, the term of this patent is extended or adjusted under 35 U.S.C. 154(b) by 192 days.

(21) Appl. No.: 10/546,052

(22) PCT Filed: Feb. 20, 2004

(86) PCT No.: PCT/JP2004/002026

§ 371 (c)(1), (2), (4) Date: May 22, 2006

(87) PCT Pub. No.: WO2004/074976

PCT Pub. Date: Sep. 2, 2004

(65) Prior Publication Data

US 2007/0140653 A1    Jun. 21, 2007

(51) Int. Cl.
*H04N 5/91* (2006.01)
*H04N 5/00* (2006.01)

(52) U.S. Cl. .......................................... 386/95; 386/126

(58) Field of Classification Search .................. None
See application file for complete search history.

(56) References Cited

U.S. PATENT DOCUMENTS

| 2004/0151083 | A1 | 8/2004 | Ichikawa et al. |
| 2004/0197083 | A1 | 10/2004 | Kim et al. |
| 2004/0228618 | A1 | 11/2004 | Yoo et al. |
| 2005/0008338 | A1 * | 1/2005 | Yamauchi et al. ............. 386/95 |
| 2005/0084245 | A1 | 4/2005 | Taira et al. |
| 2005/0254787 | A1 | 11/2005 | Ando et al. |
| 2006/0193606 | A1 * | 8/2006 | Lamkin et al. ................. 386/95 |

FOREIGN PATENT DOCUMENTS

| JP | 2001-332006 | 11/2001 |
| JP | 2004-213714 | 7/2004 |
| JP | 2004-342173 | 12/2004 |
| JP | 2005-85335 | 3/2005 |
| JP | 2006-514394 | 4/2006 |
| WO | WO 2004/074976 | 9/2004 |

* cited by examiner

*Primary Examiner*—Thai Tran
*Assistant Examiner*—Heather R Jones

(57) ABSTRACT

A recording medium capable of executing menu calls based on the particular characteristics of different versions of the same movie work when these different versions are recorded on a single recording medium. An AV clip and a dynamic scenario are recorded on a BD-ROM 100 (recording medium). The dynamic scenario is a command string showing a playback control procedure relating to video data, and has attribute information attached thereto. Attribute information is information showing a control procedure for when a user requests a menu call during AV clip playback, and includes a resume_intension_flag. The resume_intension_flag shows whether playback resumption of video data after the menu call ends is intended.

29 Claims, 39 Drawing Sheets

```
MovieObject(1){
resume_intension_flag=0
     menu_call_mask=0
   Title_search_mask=0
function{PlayPL(PL#1,PI#1)
  if(SPRM(0)=="Japanese"){
  PlayPL(PL#4,PI#1);
  }else{
  PlayPL(PL#2,PI#1);}
  PlayPL(PL#3,PI#1);
          }
               }
```

FIG. 1A
DYNAMIC SCENARIO
```
function{PlayPL(PL#1,Pl#1)
 if(SPRM(0)=="Japanese"){
PlayPL(PL#4,Pl#1);
}else{
PlayPL(PL#2,Pl#1);}
PlayPL(PL#3,Pl#1);
          }
                }
```
FIG. 1B
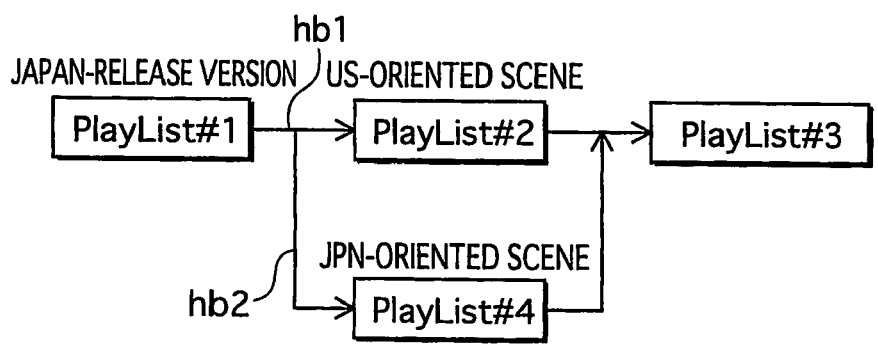
FIG. 1C
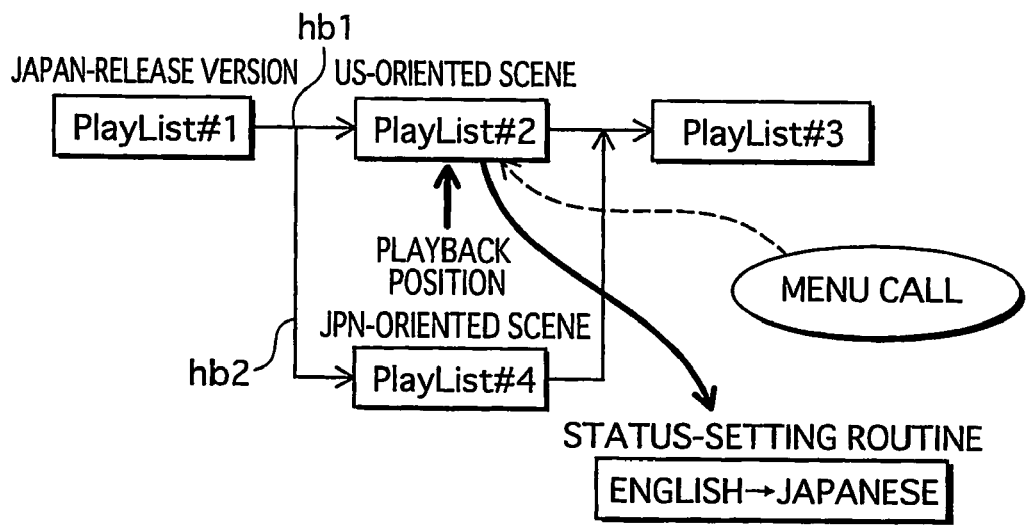

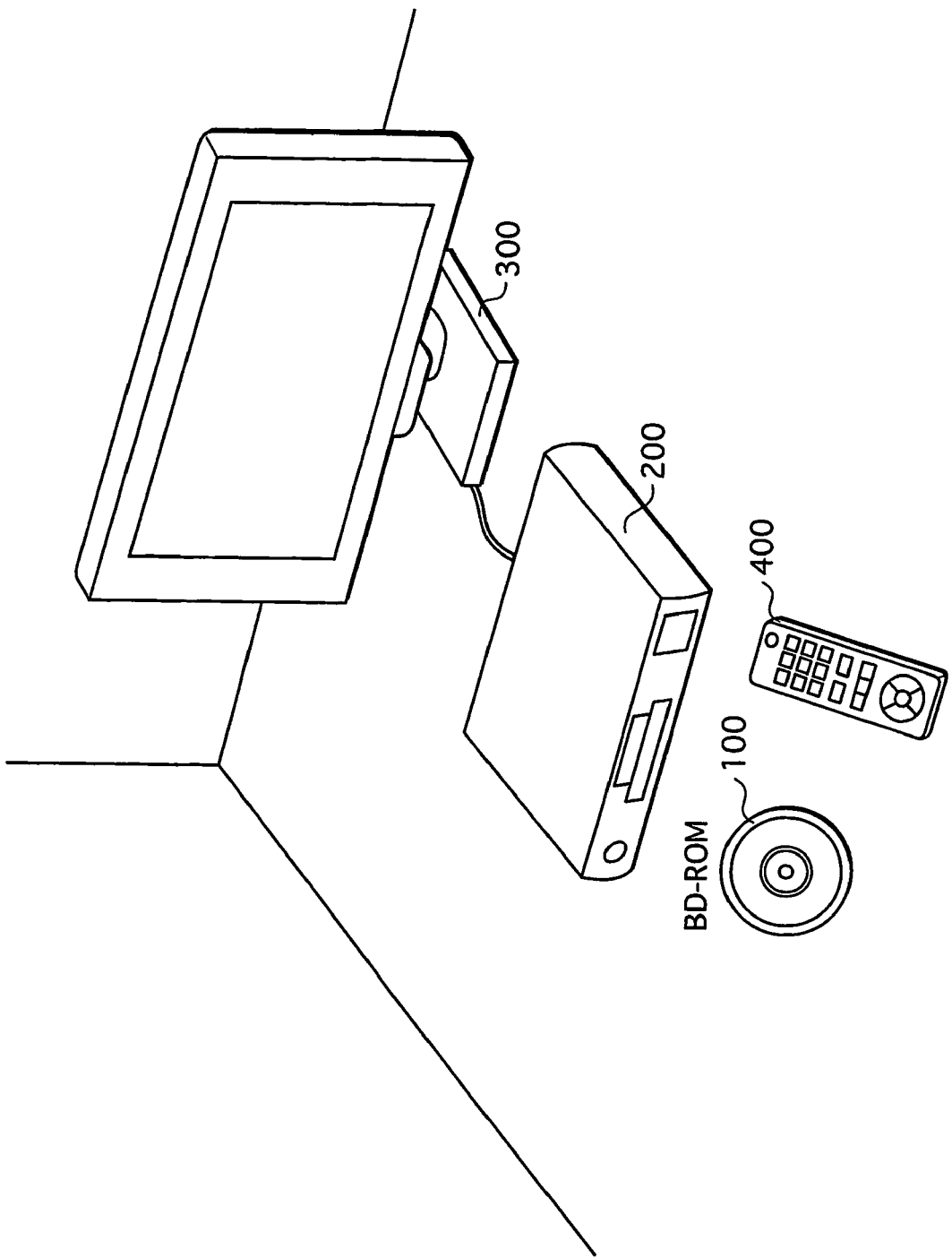

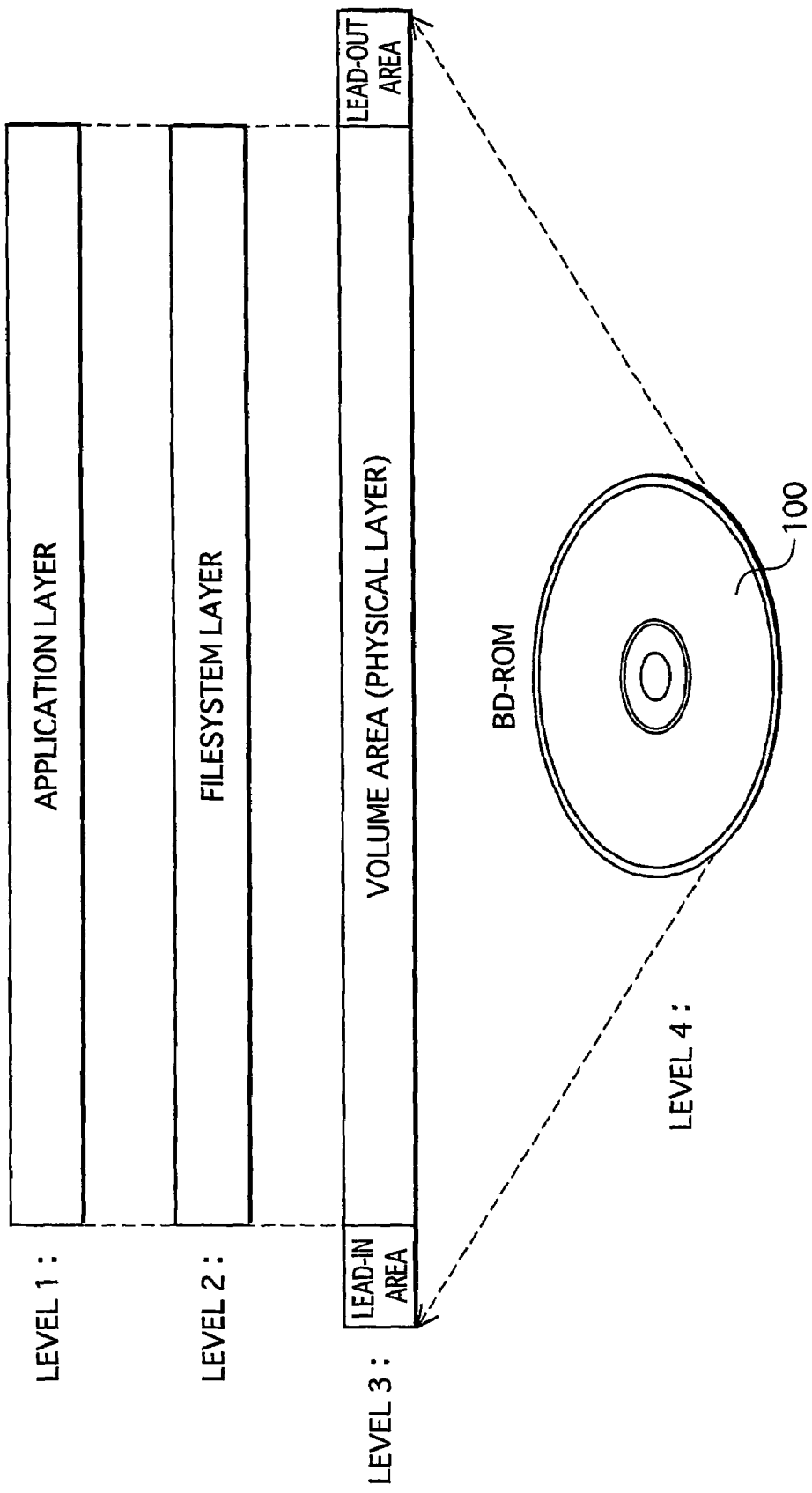

FIG. 14A
```
MovieObject(1){
resume_intension_flag=0
    menu_call_mask=0
   Title_search_mask=0
function{PlayPL(PL#1,Pl#1)
 if(SPRM(0)=="Japanese"){
 PlayPL(PL#4,Pl#1);
 }else{
 PlayPL(PL#2,Pl#1);}
 PlayPL(PL#3,Pl#1);
         }
              }
```
FIG. 14B
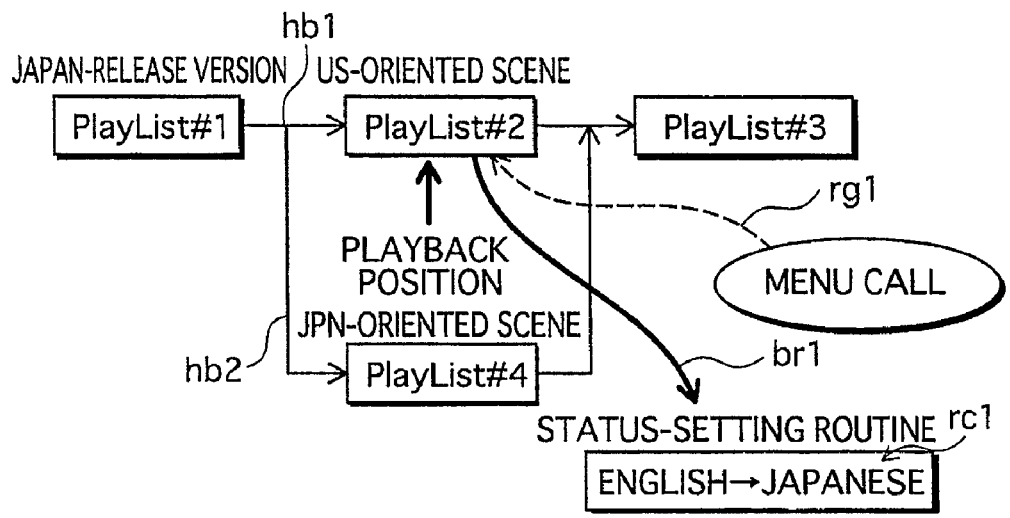
FIG. 14C
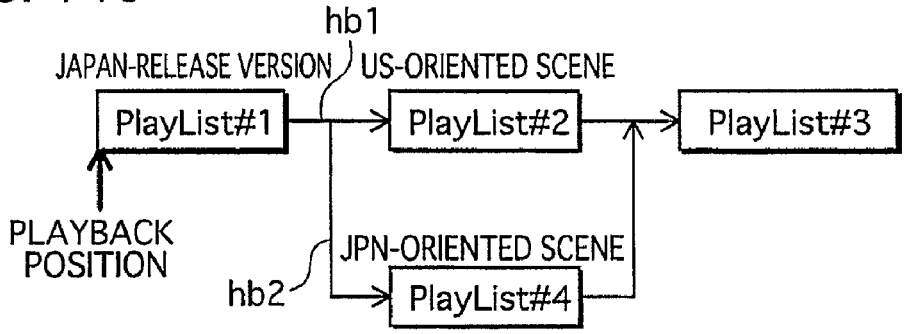

FIG. 16A
```
MovieObject(1){
resume_intension_flag=1
    menu_call_mask=0
    Title_search_mask=0
function{PlayPL(PL#1,PI#1)
  if(GPRM(0)=="Answer1"){
  PlayPL(PL#4,PI#1);
  }else{
  PlayPL(PL#2,PI#1);}
  PlayPL(PL#3,PI#1);
       }
            }
```
FIG. 16B
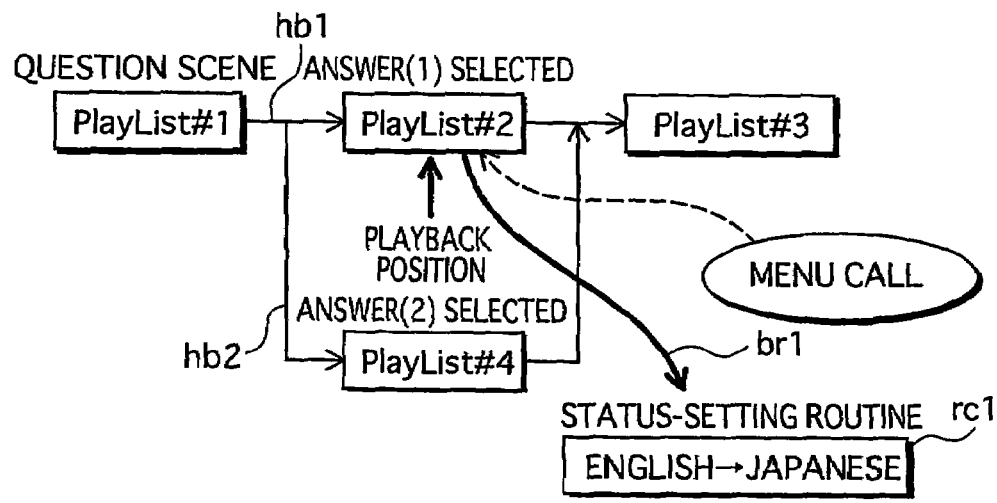
FIG. 16C
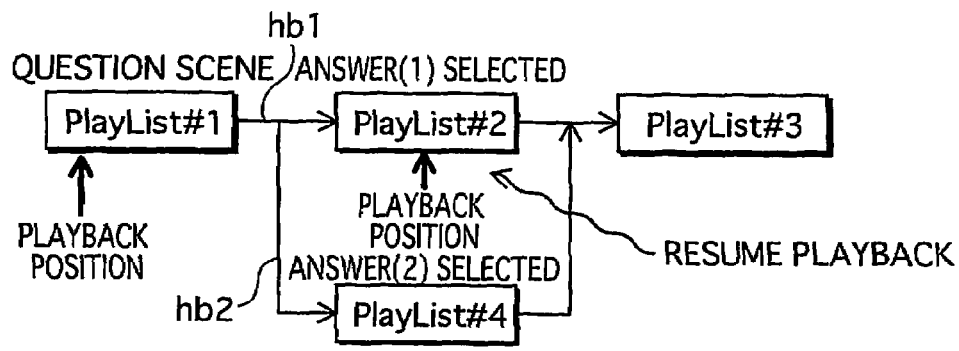

FIG. 17A
```
MovieObject(1){
resume_intension_flag=0
     menu_call_mask=0
     Title_search_mask=0
function{PlayPL(PL#4,PI#1)
 PlayPL(PL#1,PI#1);
 if(SPRM(13)=="kids"){
 PlayPL(PL#4,PI#1);
 }else{
 PlayPL(PL#2,PI#1);}
 PlayPL(PL#3,PI#1);
}
```
FIG. 17B
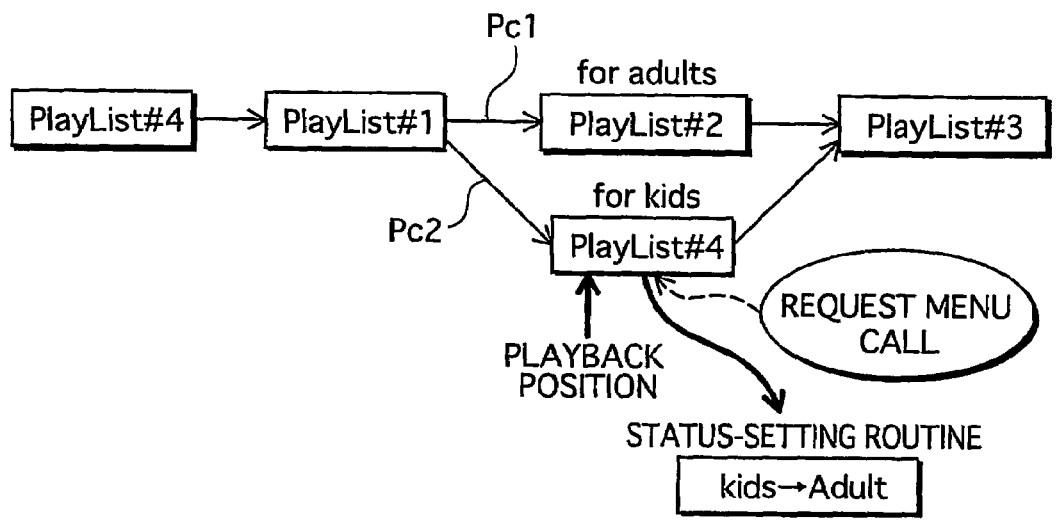
FIG. 17C
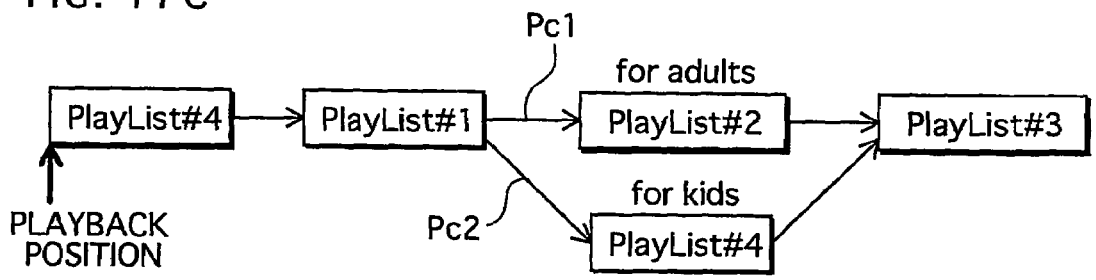

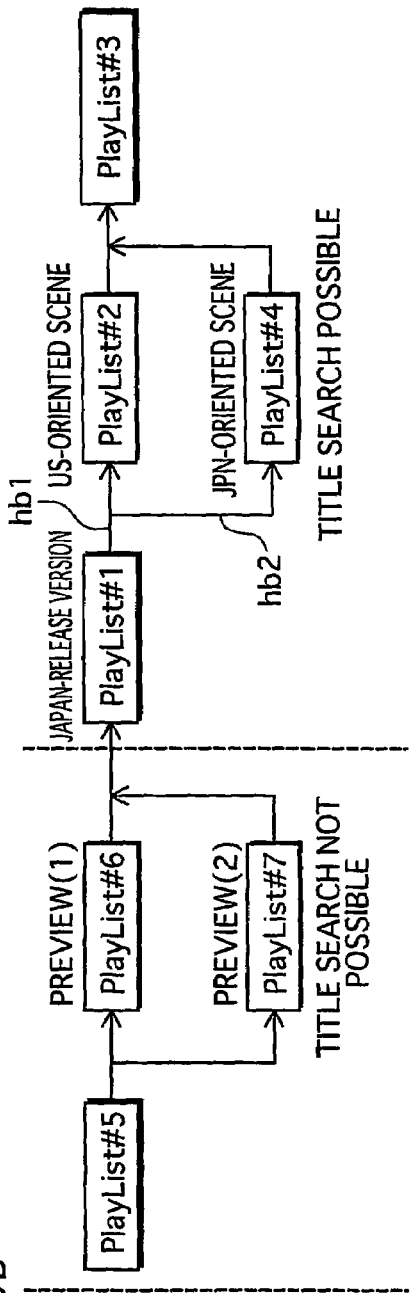

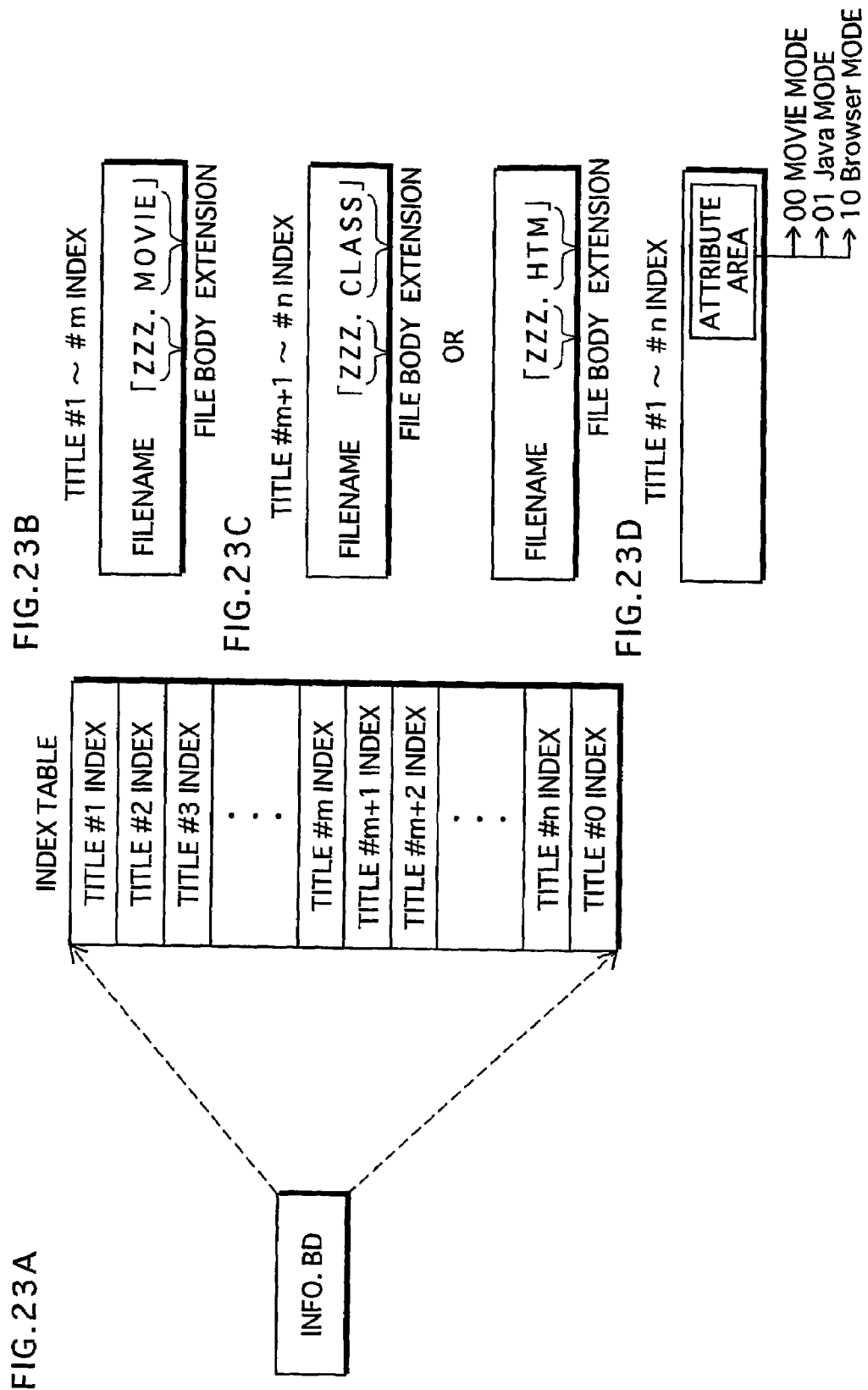

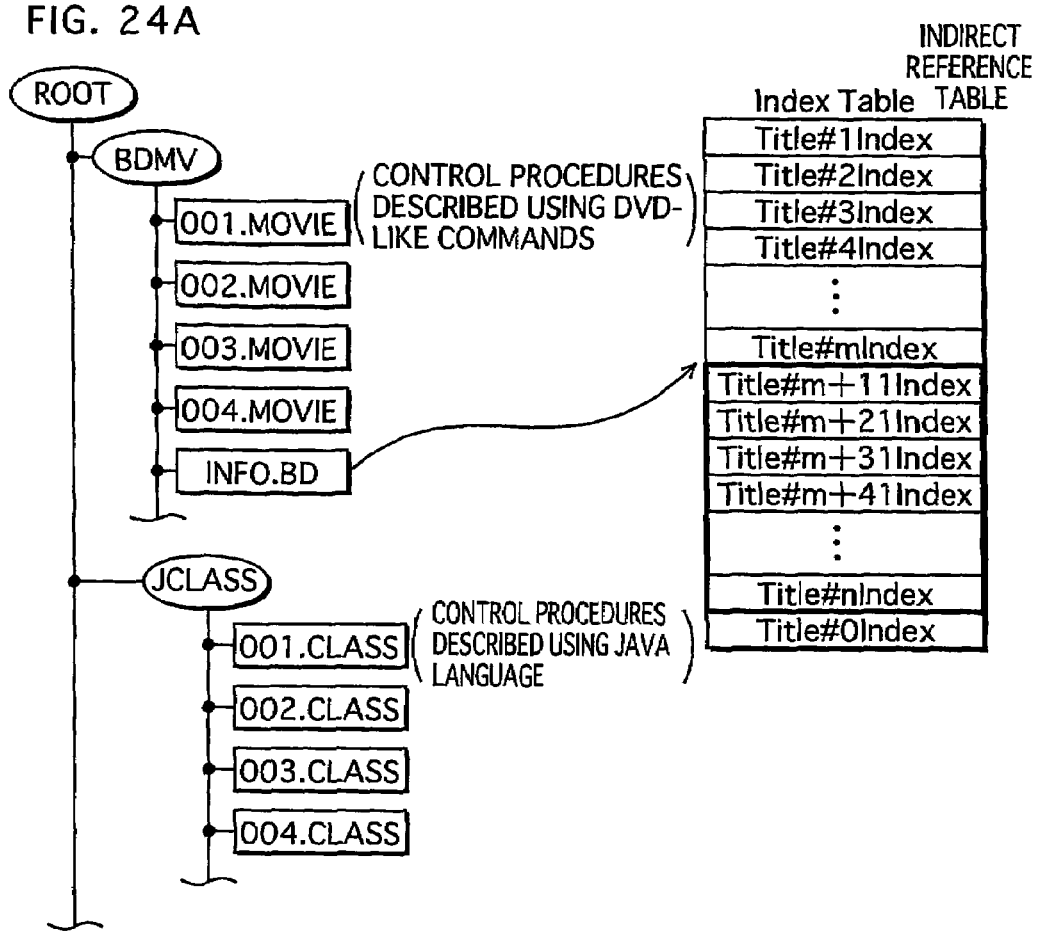

MOVIE MODE + JAVA MODE-POSSIBLE (FULL SYSTEM)

ONLY MOVIE MODE POSSIBLE (CORE SYSTEM)

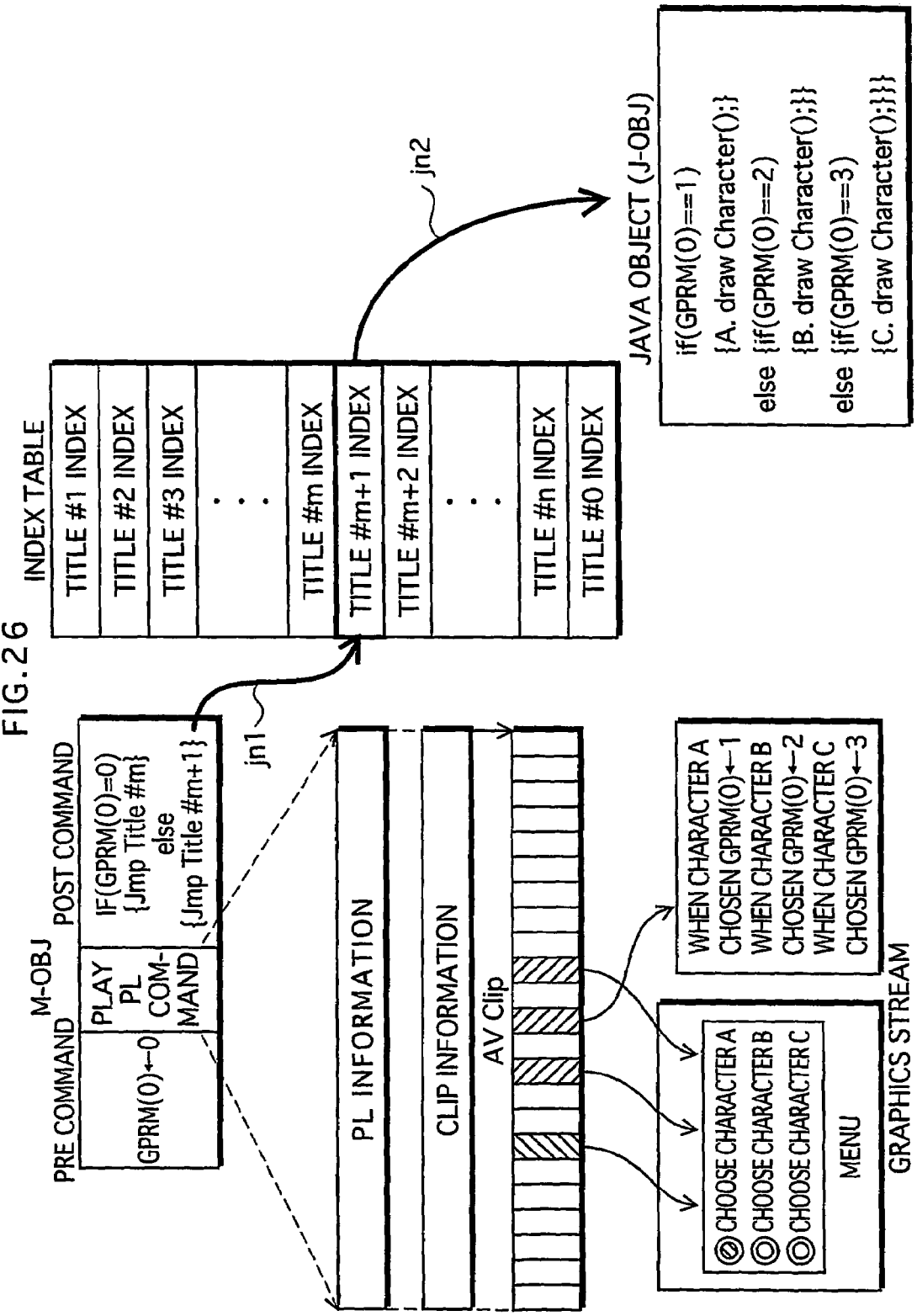

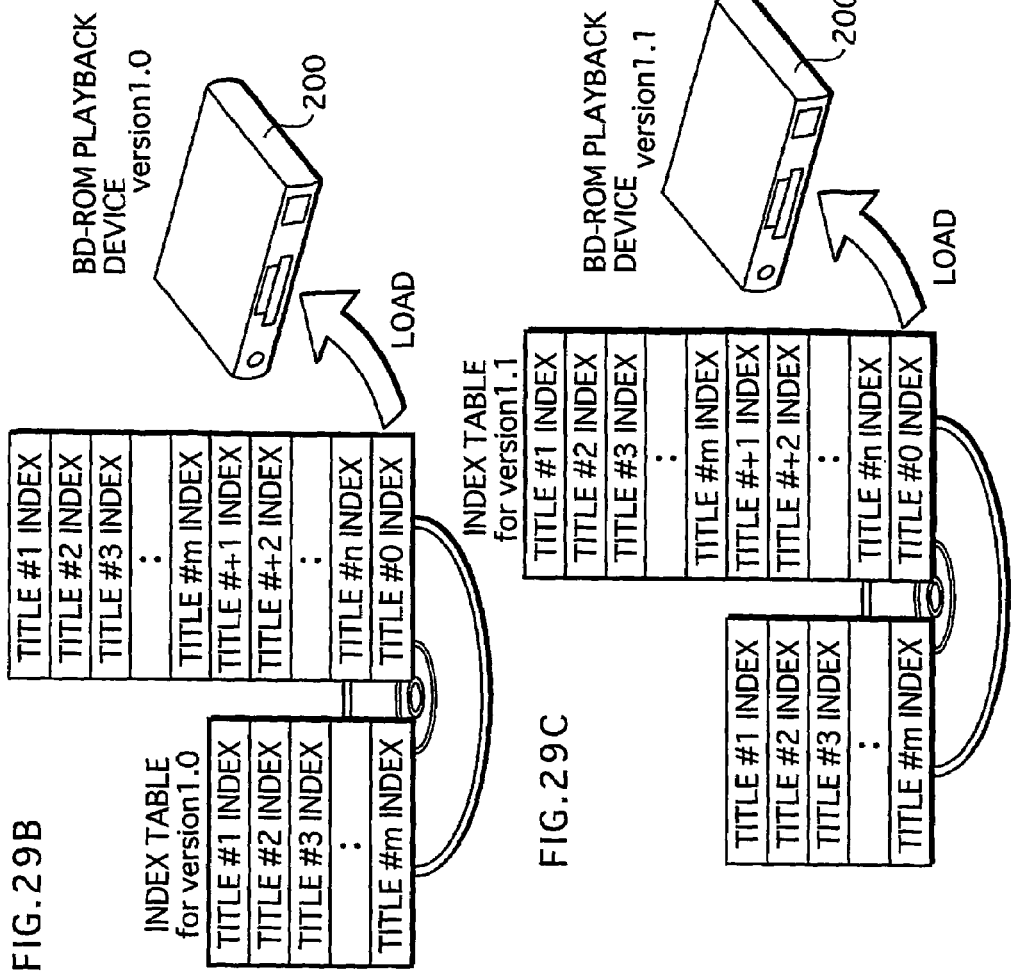
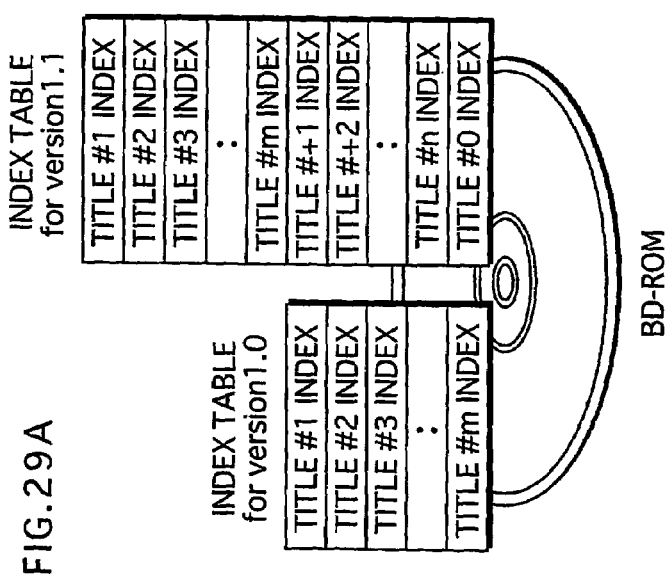

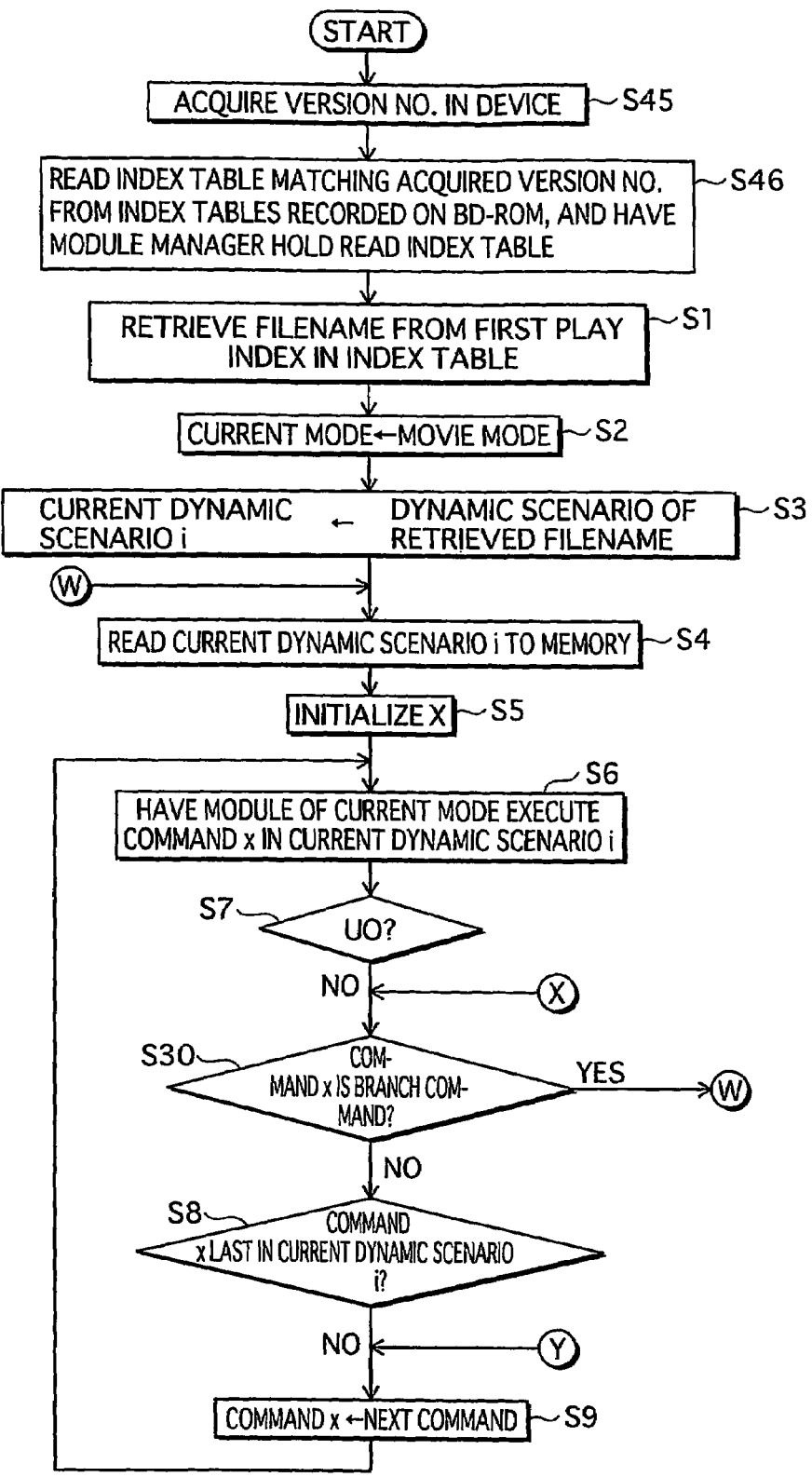

FIG. 37  COMMENTARY USING Audio_PID3

RECORDING MEDIUM, PLAYBACK DEVICE, RECORDING METHOD, PLAYBACK METHOD, AND COMPUTER PROGRAM

TECHNICAL FIELD

The present invention relates to recording media such as BD-ROMs for distributing movie works and playback devices for playing such recording media, and in particular to improving the way in which movie works that realize dynamic playback controls are provided.

BACKGROUND ART

With the retail of DVD-ROMs and BD-ROMs, the greater the number of variations of a movie work (title) that can be sold on a single disk, the greater the added value of the product. Scenario data called static scenarios and dynamic scenarios plays a positive role in increasing the number of title variations. A static scenario is information showing a playback path defined in advance by a disk creator. In comparison, a dynamic scenario is a scenario that dynamically changes the progress of playback according to a status setting of the device.

FIGS. 1A-1C show a dynamic scenario. The dynamic scenario realizes a "language credit" for switching playback scenes according to a language setting in the playback device. In FIGS. 1A-1C, "PL" is short for PlayList, which is a playback path, and "PI" is short for PlayItem, which is a playback section. The dynamic scenario in FIGS. 1A-1C realizes conditional playback such that if the language setting (SPRM(0)) in the playback device is "Japanese" (i.e. "if (SPRM(0))==Japanese"), playback section PI#1 of playback path PL#4 (PL#4, PI#1) is played, and if the language setting in the playback device is other than PL#4 (i.e. "else"), playback section PI#1 of playback path PL#2 (PL#2, PI#1) is played. As a result of this conditional playback, playback is performed via playback paths that differ depending on the language setting made by the user. The arrows hb1 and hb2 in FIG. 1B symbolically show the conditional branching that results from a dynamic scenario. The prior art relating to DVD playback controls includes the known technology disclosed in Japanese patent application no. 2856363.

However, if the user conducts a menu call while the playback device is executing a playback control in accordance with an internal status setting, there is a danger that the status setting of the playback device will be altered. A menu call is an on-demand type branch for branching to a status-setting routine in the playback device triggered by the user depressing a menu key. Being a call rather than a jump, the menu call follows processing (1) for saving a value held in a register of the playback device prior to the execution of the status-setting routine, and follows processing (2) for restoring the saved value to the register after the execution of the status-setting routine. Register-held values that are saved and restored show the current point in time of playback. As such, even if the user requests a menu call in the middle of a playback path, thereby initiating a status-setting routine, playback is resumed from immediately after the previous playback position once the status-setting routine has ended.

In the example given here, the language setting in the playback device is English, and the playback time in FIGS. 1A-1C is over PL#2, which is the playback path specifically for English. If a menu call is conducted in the above state and the status setting in the playback device is updated from English to Japanese, the playback device loses the position for resuming playback. This is because it does not make sense to resume playback on the English language playback path when the language setting has changed from English to Japanese as a result of the menu call. Also, the setting of a meaningless playback position risks inviting a hang up when software is implemented in the playback device.

These difficulties can be avoided by uniformly prohibiting menu calls. However, when a number of versions of a movie work are recorded on a single optical disk, it is fully conceivable that a title that does not execute language credits is recorded on the optical disk. Uniformly preventing menu calls during the playback of titles shows a lack of consideration to the user.

An object of the present invention is to provide a recording medium capable of executing menu calls in response to the particular characteristics of individual titles when different versions of a movie work are recorded on a single recording medium.

DISCLOSURE OF THE INVENTION

A recording medium provided to achieve the above object has video data and a dynamic scenario recorded thereon, the dynamic scenario being a command string showing a playback control procedure of the video data and having attribute information appended thereto, the attribute information showing a control procedure for when a user requests a menu call during playback of the video data and including a first flag, and the first flag indicating, when the menu call ends during playback of the video data, whether to resume playback of the video data from the playback position at the time that the menu call was requested.

According to this structure, control procedures relating to menu calls are set at a dynamic scenario level, which is the highest layer in a layer model comprising, from bottom to top, streams, playback paths, and dynamic scenarios. When a title that the creator particularly wants to create realizes a language credit, controls can be performed to accept requests for menu calls without resuming playback. As a result, titles can be easily divided into two types even when the streams and playback paths are the same; namely, titles with respect to which menu calls are permitted, and titles with respect to which menu calls are prohibited. With the creation of titles, the number of variations having different control procedures can be increased with little effort, since there is no increase the number of playback paths or streams.

Japanese patent application no. 2856363 discloses technology for setting the permissibility of user operations based on stream levels and playback paths. According to the disclosed technology, dividing titles into those with respect to which menu calls are either permitted or prohibited would result in an indiscriminate increase the number of streams and playback paths because of the permissibility of user operations being set based on stream levels and playback paths. In contrast, with the present invention, there is no increase in the number of streams and playback paths, because the permissibility of playback resumption after completion of a menu call is set at a dynamic scenario level. Since there is little if any increase in the number of streams and playback paths, it is possible according the present invention to prevent errors such as titles with respect to which menu calls should be permitted being confused with titles with respect to which menu calls are prohibited.

BRIEF DESCRIPTION OF THE DRAWINGS

FIGS. 1A-1C show a dynamic scenario;

FIG. 2 shows a usage application of a recording medium pertaining to the present invention;

FIG. 3 shows a structure of a BD-ROM;

FIG. 14A shows a dynamic scenario having resume_intension_flag, menu_call_mask, and Title_search_mask appended thereto;

FIG. 14B shows a playback control based on the MOVIE object in FIG. 14A;

FIG. 14C shows playback being restarted from the head of a title;

FIGS. 16A-16C show a descriptive example of a MOVIE object when branching that results from a question is realized;

FIGS. 17A-17C show a descriptive example of a dynamic scenario when indicating a parental lock;

FIGS. 18A-18b show an exemplary setting of the Title_search_mask;

FIG. 23A-23D show an internal structure of INFO.BD;

FIG. 24A shows a BD-ROM having a plurality of dynamic scenarios (001.MOVIE, 002.MOVIE, 003.MOVIE, . . . , 001.CLASS, 002.CLASS, 003.CLASS, . . . )recorded thereon;

FIG. 24B shows a descriptive example of an Index Table when the dynamic scenarios shown in FIG. 24A are listed;

FIG. 26 schematically shows how branching from a MOVIE object to a Java object is performed;

FIG. 29A shows a BD-ROM having a plurality of Index Tables for different versions recorded thereon;

FIG. 29B assumes the BD-ROM in FIG. 29A being mounted in a version 0.1 playback device;

FIG. 29C assumes the BD-ROM in FIG. 29A being mounted in a version 1.1 playback device;

FIG. 30 is a flowchart showing processing procedures performed by module manager 20;

BEST MODE FOR CARRYING OUT THE INVENTION

Embodiment 1

An embodiment of a recording medium pertaining to the present invention is described below. Firstly, a usage act is described in relation to the implementation of a recording medium pertaining to the present invention. FIG. 2 shows a usage act of a recording medium pertaining to the present invention. BD-ROM 100 in FIG. 2 is a recording medium pertaining to the present invention. BD-ROM 100 is used to supply movie works in a home theater system formed from a playback device 200, a television 300, and a remote controller 400.

Next, a production act is described in relation to the implementation of a recording medium pertaining to the present invention. A recording medium pertaining to the present invention can be implemented as a result of enhancements in the application layer of BD-ROMs. FIG. 3 shows the structure of a BD-ROM.

Level 4 in FIG. 3 shows a BD-ROM, and the third level shows a track on the BD-ROM. The track at level 3 depicts, in a laterally drawn-out form, the tracks spiraling from the inside to the outside of the BD-ROM. These tracks are formed from a lead-in area, a volume area, and a lead-out area. The volume area in FIG. 3 has a layer model consisting of a physical layer, a filesystem layer, and an application layer. A recording medium pertaining to the present invention is industrially manufactured by forming the data format shown in FIG. 3 on the application layer of a BD-ROM.

Figure 4:
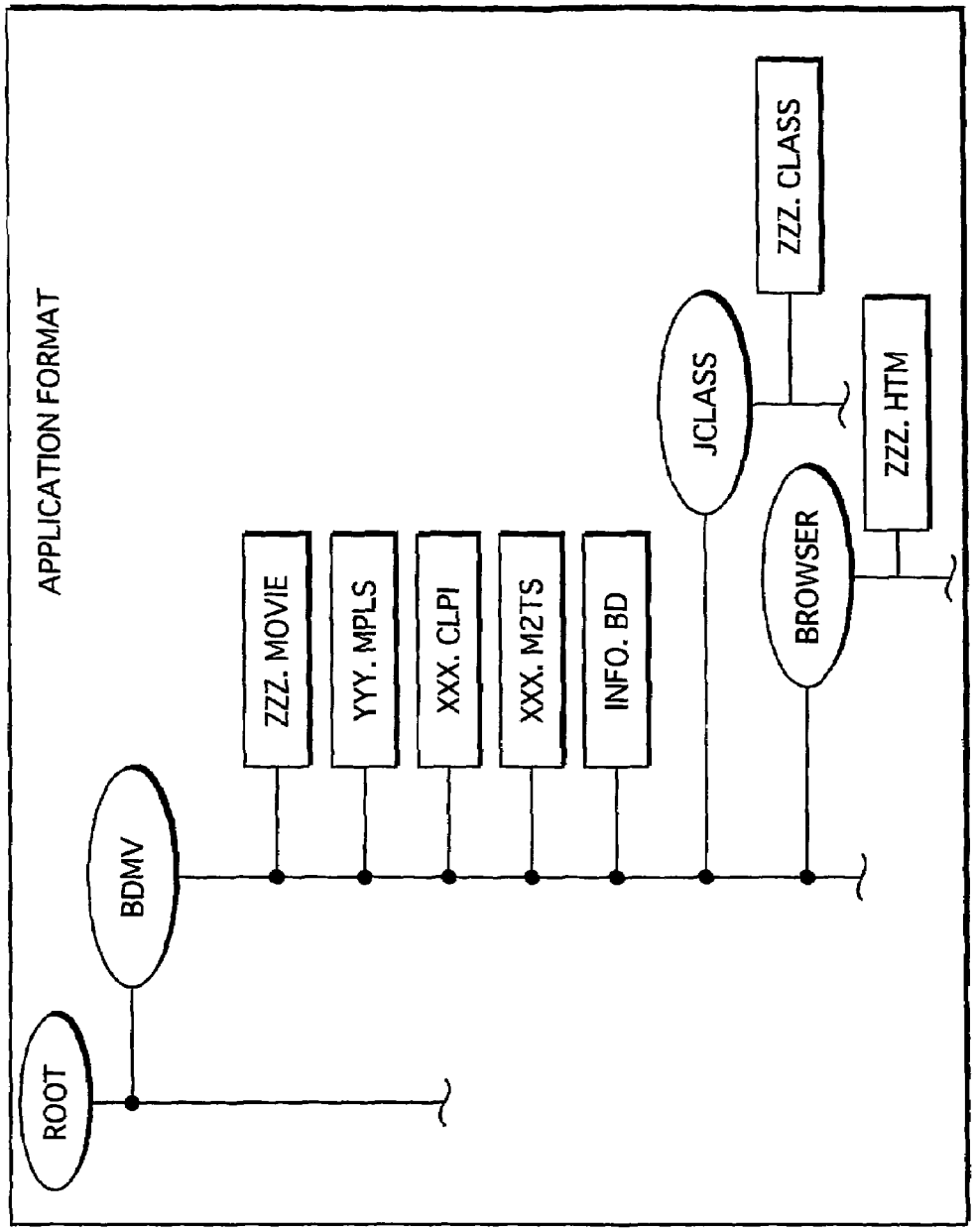
FIG. 4 represents an application format of a BD-ROM using a directory structure.

FIG. 4 expresses an application layer format (hereinafter, simply "application format") of a BD-ROM using a directory structure. As shown in FIG. 4, below a ROOT directory in the BD-ROM is a BDMV directory, and below the BDMV directory is a JCLASS directory and a BROWSER directory. Subordinate to the BDMV directory exist the following files: INFO.BD, XXX.M2TS, XXX.CLPI, YYY.MPLS, and ZZZ.MOVIE. Subordinate to the JCLASS directory is disposed ZZZ.CLASS, and subordinate to the BROWSER directory is disposed ZZZ.HTM.

Figure 5:
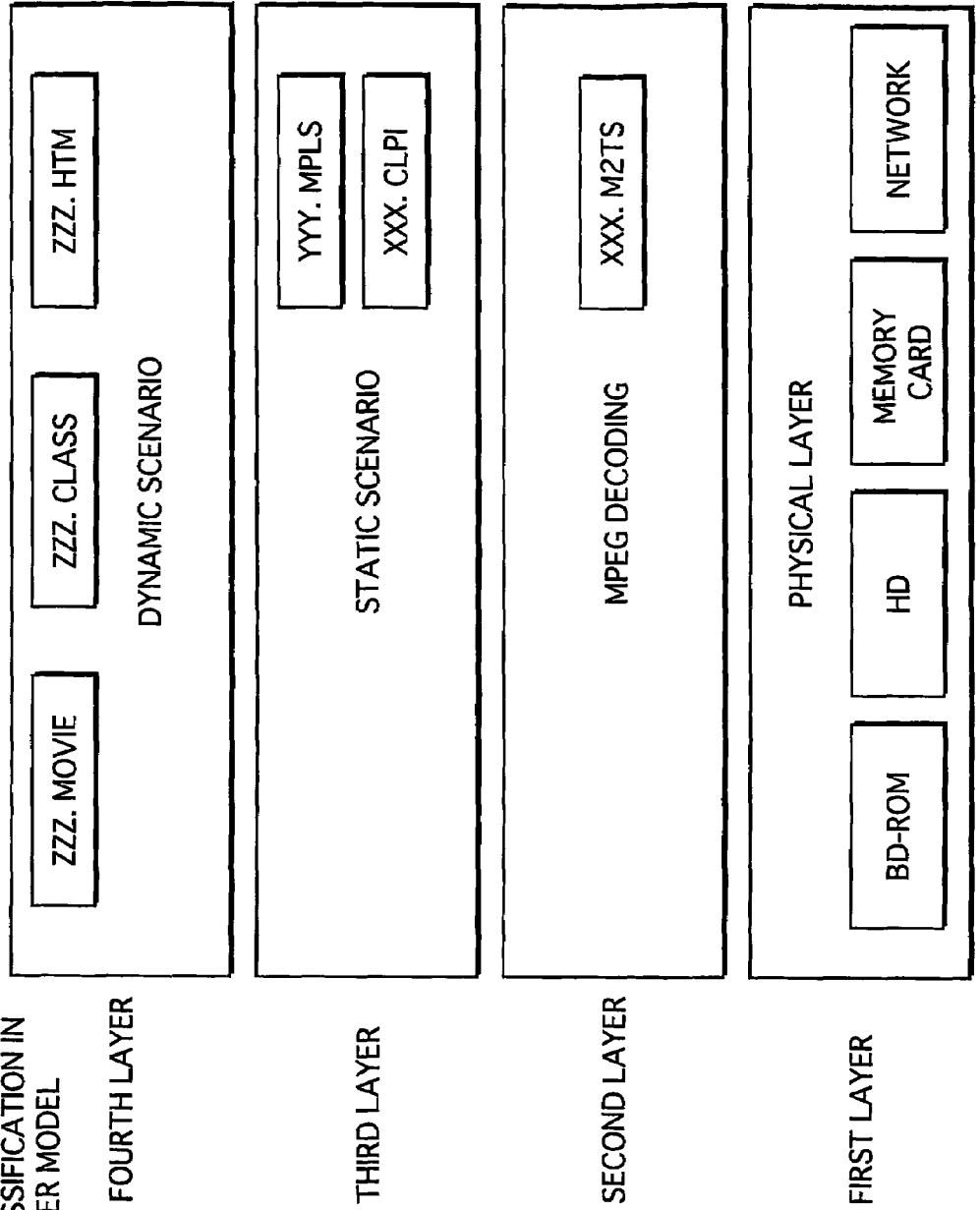
FIG. 5 is a classification diagram showing the files in FIG. 4 classified in terms of functionality.

FIG. 5 is a classification diagram of when these files are classified from a functionality viewpoint. In FIG. 5, the hierarchy formed from the first, second, third and fourth layers symbolically shows the classifications in the diagram. In FIG. 5, XXX.M2TS is grouped in the second layer. XXX.CLPI and YYY.MPLS are grouped in the third layer (static scenarios). ZZZ.MOVIE, which is subordinate to the BDMV directory, ZZZ.CLASS, which is subordinate to the JCLASS directory, and ZZZ.HTM, which is subordinate to the BROWSER directory, are grouped in the fourth layer.

Figure 6:
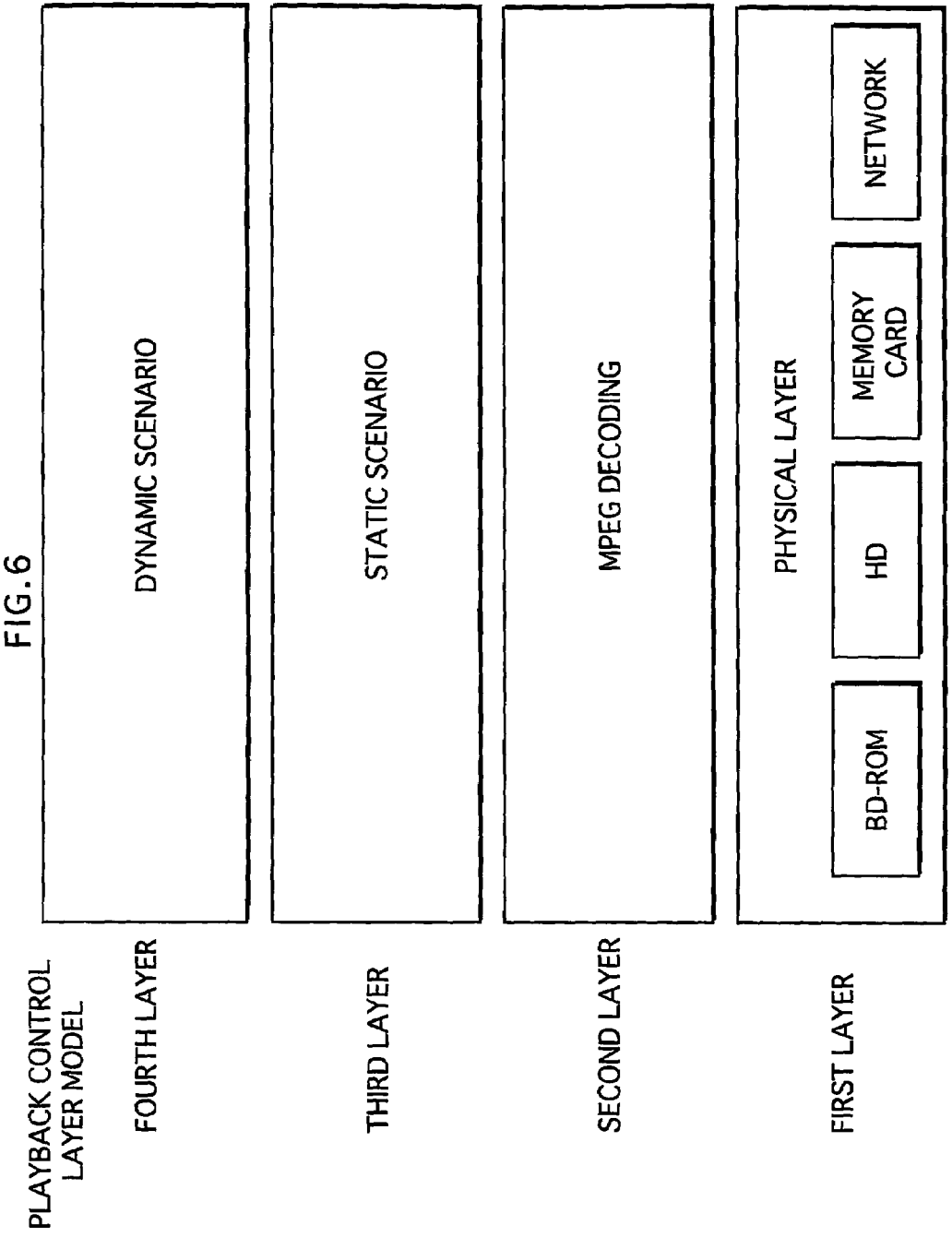
FIG. 6 shows a layer model that targets a BD-ROM.

The classifications in FIG. 5 (first to fourth layers) target a layer model such as shown in FIG. 6. A layer model in control software that targets a BD-ROM is described below while referring to FIG. 6.

The first layer in FIG. 6 is a physical layer in which supply controls relating to streams targeted for processing are implemented. As shown in the first layer, target streams have as their supply source not only BD-ROMs but also HDDs (hard disk drives), memory cards, networks and other kinds of recording and communication media. Controls (disk access, card access, network communication) directed towards these HDDs, memory cards, and networks are implemented on the first layer.

The second layer is a decoding format layer. This second layer is where the decoding format used in decoding streams supplied by the first layer is defined. The MPEG-2 decoding format is employed in the present embodiment.

The third layer (static scenarios) defines the static scenarios of streams. Static scenarios are playback path information and Clip information defined in advance by the disk creator, the third layer (static scenarios) being where playback controls based on these static scenarios are defined.

The fourth layer is for realizing dynamic scenarios in streams. Dynamic scenarios are scenarios for dynamically changing the progress of playback as a result of user operations, the device status, and the like, the fourth layer being where playback controls based on these dynamic scenarios are defined. Files relating to streams, static scenarios, and dynamic scenarios are described below in accordance with this layer model.

Firstly, an AVClip (XXX.M2TS) belonging to the second layer is described.

Figure 7:
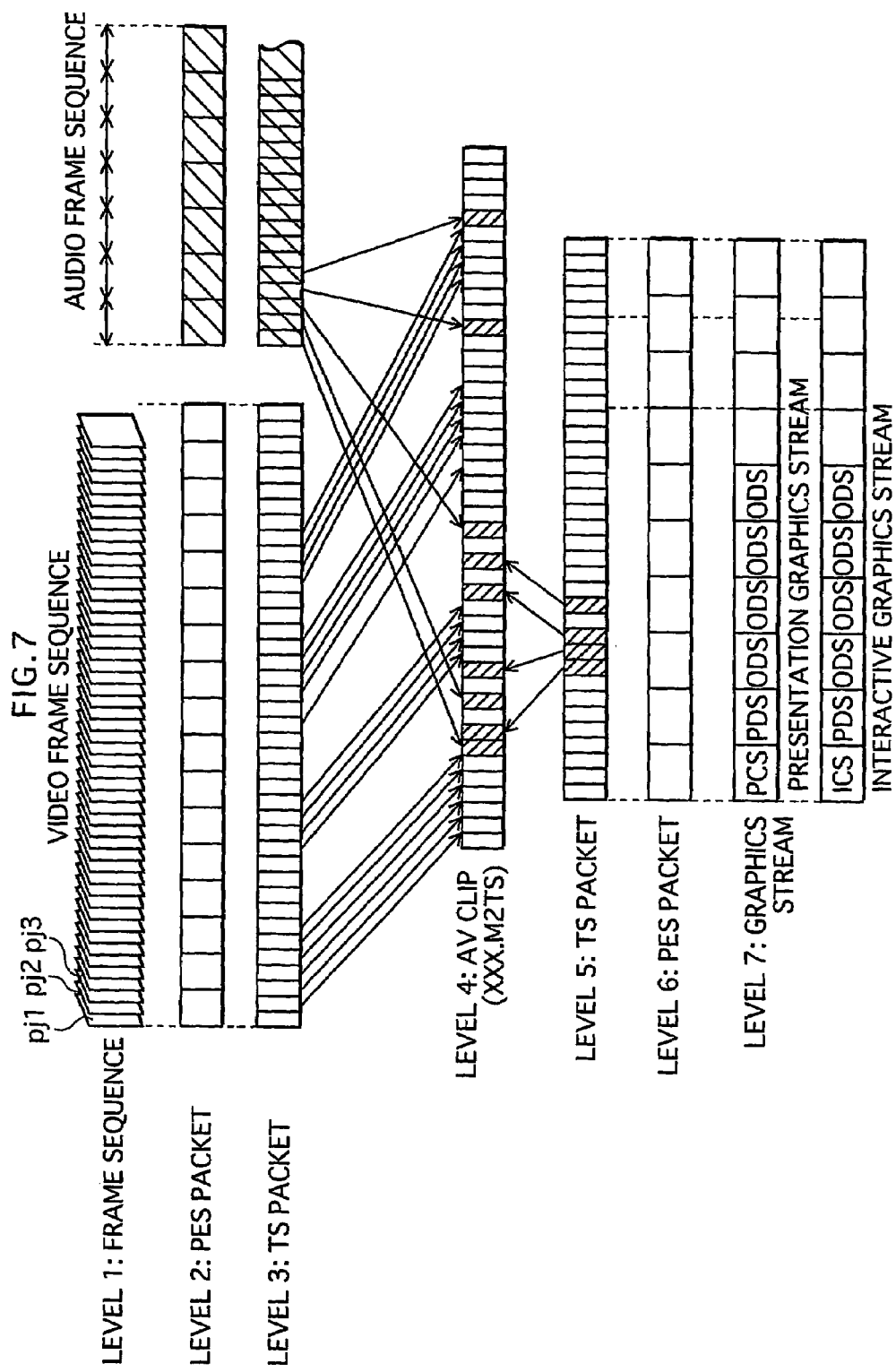
FIG. 7 schematically shows how an AV clip is structured.

AVClip (XXX.M2TS) is an MPEG-TS (transport stream) format digital stream obtained by multiplexing a video stream, one or more audio streams, and one or more graphics streams, being presentation graphics streams and interactive graphics streams. Video streams show the moving image portions of a movie, audio streams show the audio portions of a movie, presentation graphics streams show the subtitles of a movie, and interactive graphics streams show procedures involved in dynamic playback controls that target menus. FIG. 7 schematically shows how an AVClip is constituted.

An AVClip ($4^{th}$ level) is formed by converting a video stream comprising a plurality of video frames (pictures pj1, pj2, pj3) and an audio stream comprising a plurality of audio frames ($1^{st}$ level) into a PES packet string ($2^{nd}$ level), which is then converted to TS packets ($3^{rd}$ level). Likewise, a subtitle-related presentation graphics stream and a dialogue-related interactive graphics stream ($7^{th}$ level) are converted to a PES packet string ($6^{th}$ level), which is converted to TS packets ($5^{th}$ level), and the TS packets are then multiplexed. The multiplexing involves arranging TS packets storing video frames and TS packets storing audio frames so that audio frames are positioned close to video frames that are to be read from the BD-ROM at the same time as the audio frames.

AVClips generated though the above process are portioned into a plurality of extents and recorded in an area of a BD-ROM, as is the case with normal computer programs. An AVClip comprises one or more ACCESS UNITs, and can be cued in these ACCESS UNITs. An ACCESS UNIT is the smallest decoding unit that includes a single GOP (group of pictures) and audio frames to be read at the same time as the GOP. GOPs include bi-directionally predictive (B) pictures, which are compressed using time-correlation characteristics with images to be played in a past direction and a future direction, predictive (P) pictures, which are compressed using time-correlation characteristics with images to be played in a past direction, and intra (I) pictures, which are compressed using frequency-correlation characteristics (i.e. not time-correlation characteristics) in the images of individual frames.

Moreover, the filename "XXX" in XXX.M2TS abstracts the 3-digit identification number appended to the AVClip in the BD-ROM. That is, the AVClip in FIG. 7 is uniquely identified using the "XXX". Thus completes the description of the stream (XXX.M2TS). It should be noted that the 3-digit number referred to here is merely exemplary, and may be any length.

Static Scenarios

Static scenarios files (XXX.CLPI, YYY.MPLS) are described below.

Figure 8:
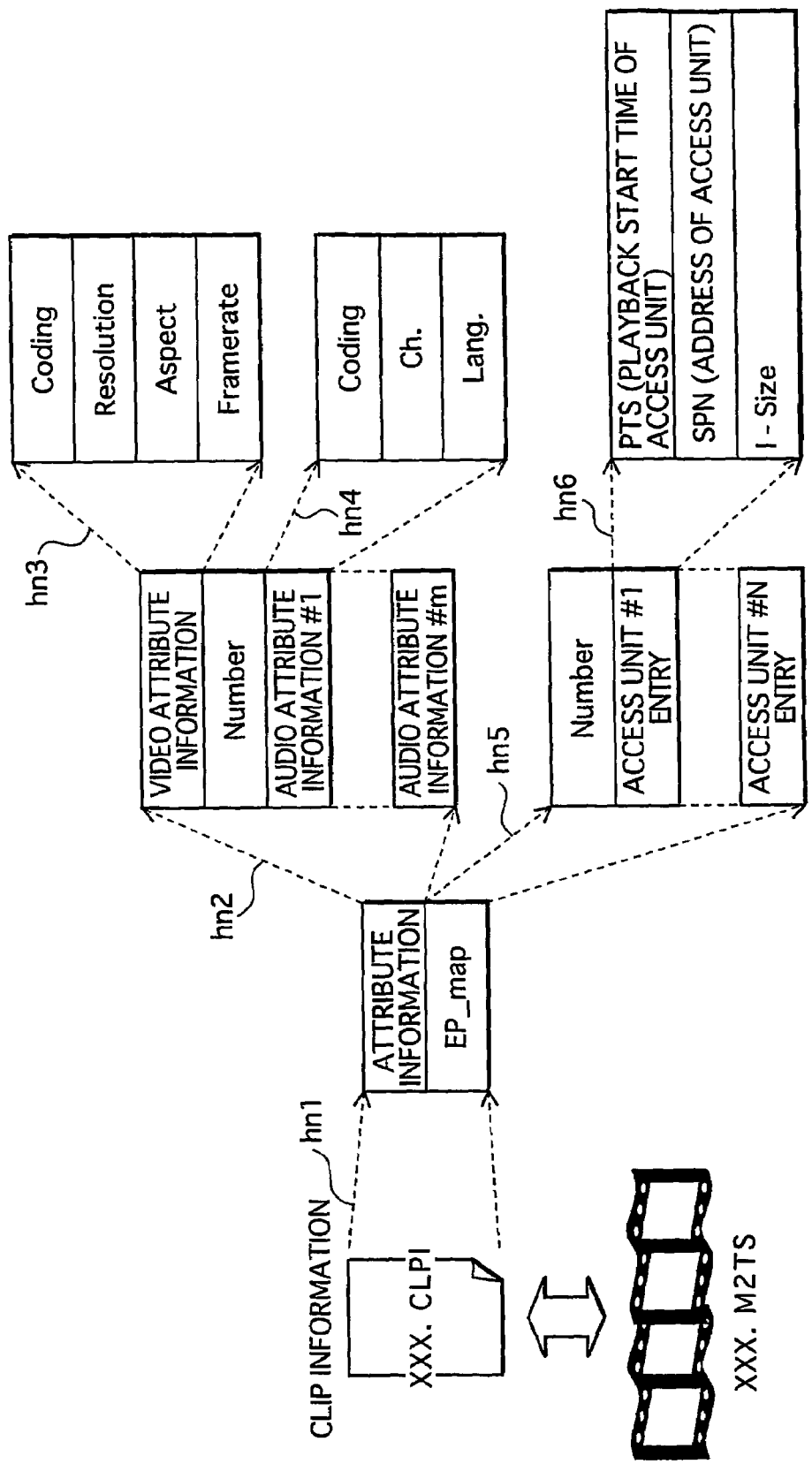
FIG. 8 shows an internal structure of Clip information.

Clip information (XXX.CLPI) is management information relating to individual AVClips. FIG. 8 shows an internal structure of Clip information. AVClips are obtained by multiplexing video and audio streams, and since AVClips can be cued in ACCESS UNITs, management items of the Clip information include the attributes of the video and audio streams and where the cue positions are in the AVClips. The leaders in FIG. 8 highlight the Clip information structure. As shown by the leader hn1, Clip information (XXX.CPLI) comprises "attribute information" relating to video and audio streams and "EP_map", which is reference table for cueing ACCESS UNITs.

Attribute information (Attribute), as shown by the leader hn2, comprises attribute information relating to a video stream (Video attribute information), an attribute information number (Number), and attribute information relating to each of a plurality of audio streams multiplexed on the AVClip (Audio attribute information #1-#m). The Video attribute information, as shown by the leader hn3, indicates the compression format used to compress the video stream (Coding), and the resolution (Resolution), aspect ratio (Aspect) and frame rate (Framerate) of individual pieces of picture data structuring the video stream.

On the other hand, Audio attribute information #1-#m relating to the audio stream, as shown by the leader hn4, indicates the compression format used to compress the respective audio streams (Coding), and the channel number (Ch.) and corresponding language (Lang.) of respective audio streams.

EP_map is a reference table for referring indirectly to the addresses of a plurality of cue positions using time information, and, as shown by the leader hn5, comprises plural pieces of entry information (ACCESS UNIT#1 entry, ACCESS UNIT#2 entry, ACCESS UNIT#3 entry, . . . ) and an entry number (Number). Each entry, as shown by the leader hn6, indicates a playback start time of a corresponding ACCESS UNIT in correspondence with an address and the size (I-size) of the head I-picture in the ACCESS UNIT. The playback start time of an ACCESS UNIT is expressed as a timestamp (presentation timestamp) of picture data positioned at the head of the ACCESS UNIT. Also, the addresses in the ACCESS UNITs are expressed by the serial numbers of TS packets (Source Packet Number or "SPN"). Since a variable-length coding compression format is employed, it is possible to cue from an arbitrary playback time to a piece of picture data in an ACCESS UNIT corresponding to the playback time by referring to the entry of the ACCESS UNIT, even when sizes and playback times of ACCESS UNITs that include GOPs are not uniform. Moreover, the filename "XXX" of XXX.CPLI uses the same name as the AVClip to which the Clip information corresponds. In other words, the filename of the Clip information in FIG. 8, being "XXX", corresponds to AVClip (XXX.M2TS). Thus concludes the description of Clip information. Playlist information is described next.

Figure 9:
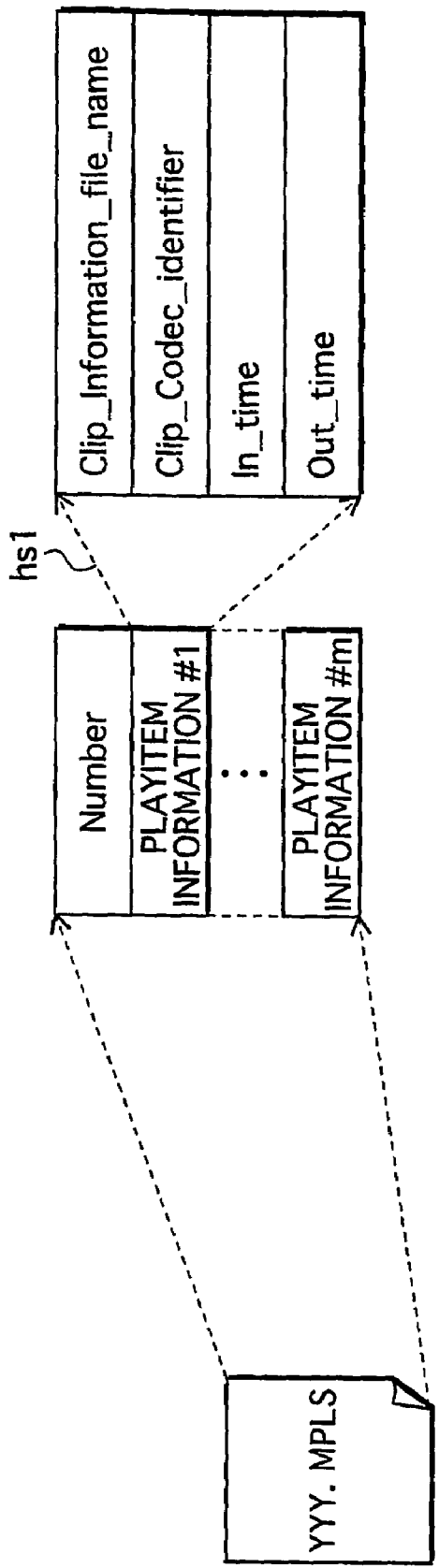
FIG. 9 shows an internal structure of PL information.

YYY.MPLS (PlayList information) is a table structuring a PlayList, which is playback path information, and comprises plural pieces of PlayItem information (PlayItem information #1, #2, #3, . . . , #n), and a PlayItem information number (Number) FIG. 9 shows an internal structure of PL information. PlayItem information is pointer information that defines one or more playback logical sections structuring a PlayList. The structure of PlayItem information is highlighted by the leader hs1. PlayItem information is, as shown by the leader hs1, structured from a "Clip_information_filename" indicating the filename of playback section information relating to an AVClip to which the In-point and Out-point of a playback section belong, a "Clip_codec_identifier" showing the encoding format used to encode the AVClip, an "In_time", which is time information showing the start of a playback section, and an "Out_time", which is time information showing the end of a playback section.

Figure 10:
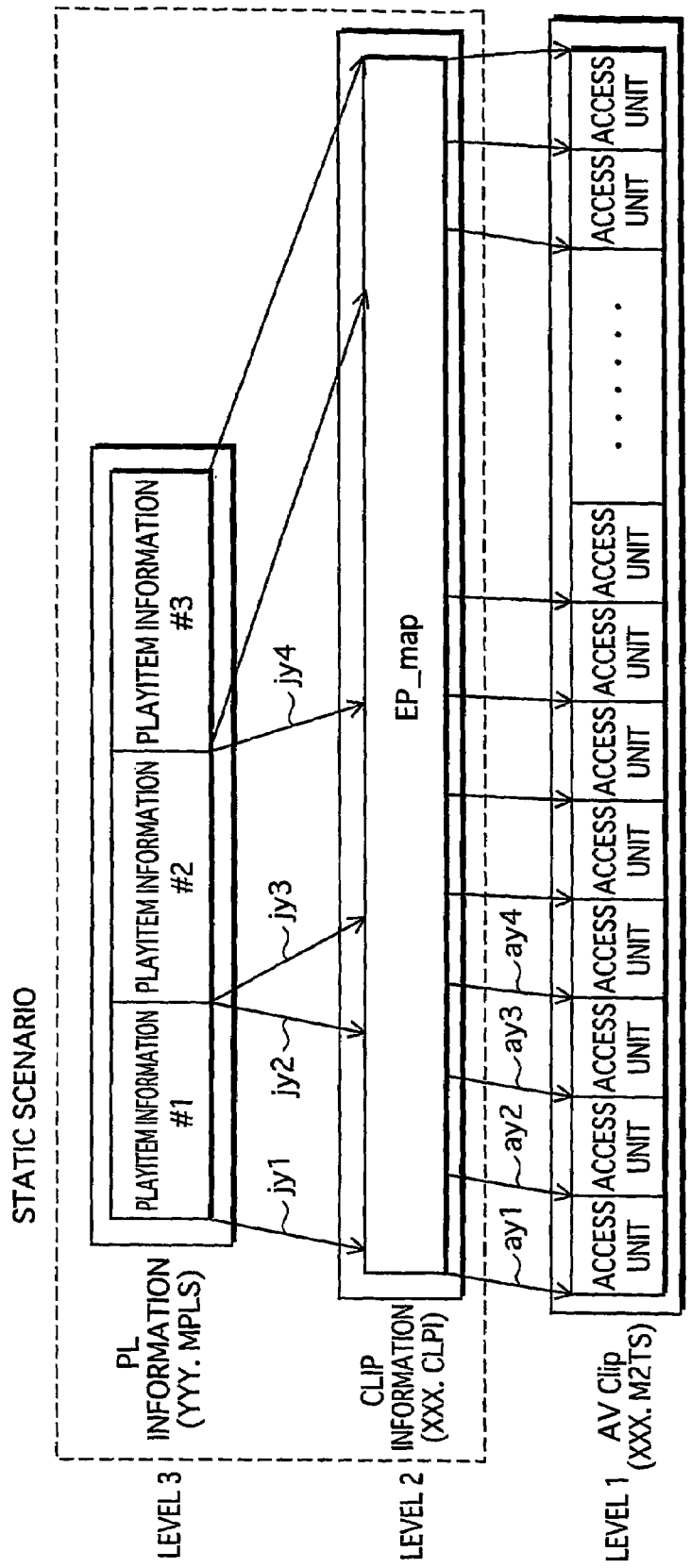
FIG. 10 schematizes indirect referencing using PL information.

A characteristic of PlayItem information is the notation. That is, playback sections are defined by an indirect referencing format that uses an EP_map as a reference table. FIG. 10 schematizes indirect referencing using PL information. The AVClip in FIG. 1 is structured from a plurality of ACCESS UNITs. The EP_map in the Clip information specifies the sector addresses of the ACCESS UNITs, as shown by the arrows ay1, ay2, ay3 and ay4. Arrows jy1, jy2, jy3 and jy4 in FIG. 10 schematically show the referencing of ACCESS UNITs using PlayItem information. In other words, this shows that referencing by PlayItem information (jy1, jy2, jy3, jy4) involves indirect referencing in which the addresses of ACCESS UNITs included in the AVClip are specified via the EP_map.

Figure 11:
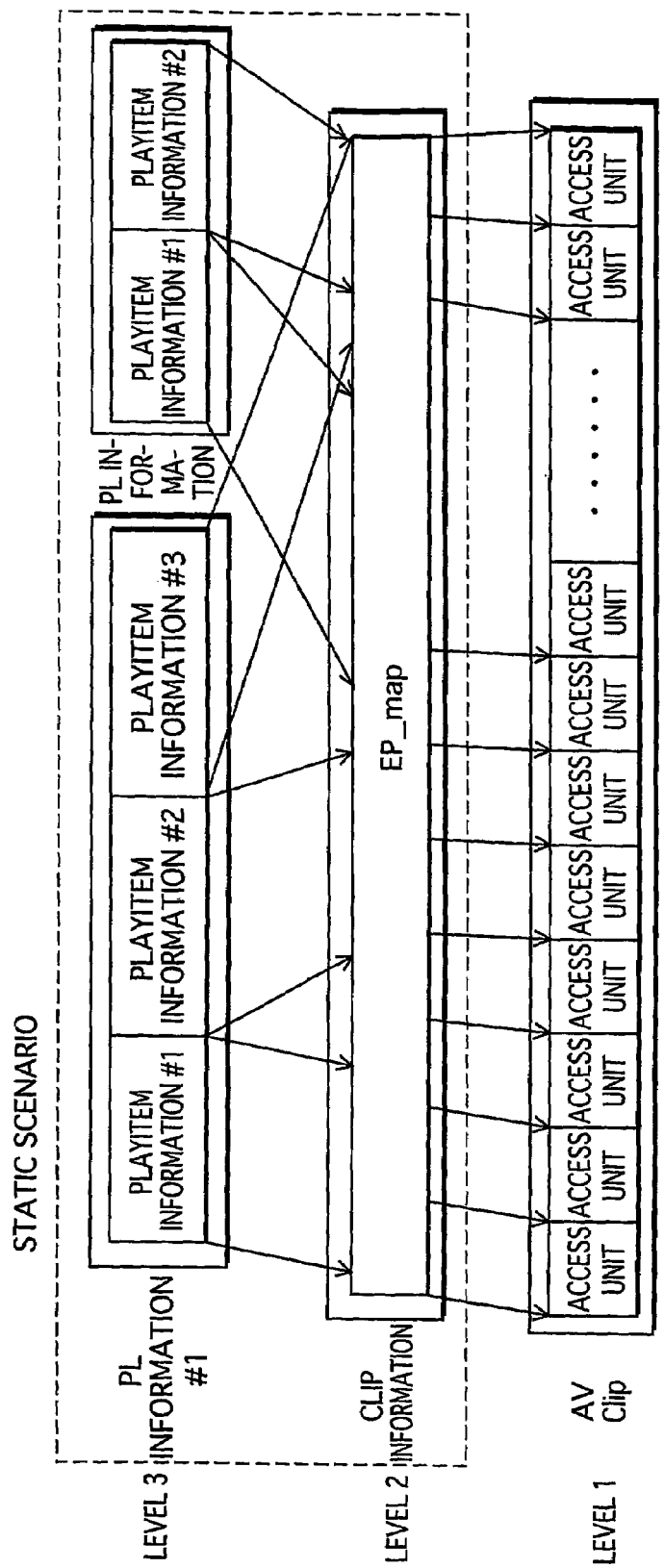
FIG. 11 shows an example of a different piece of PL information (PLinfo#2) to that (PLinfo#1) in FIG. 10 being defined.

Playback sections on BD-ROM formed from groupings of PlayItem information, Clip information and AVClips are called "PlayItems". Playback units on a BD-ROM that are formed from groupings of PL information, Clip information and AVClips are called "PlayLists" (abbreviated as "PL"). Movie works recorded on a BD-ROM are structured in these logical playback units (PLs). Since movie works on a BD-ROM are structured in logical playback units, it is possible to easily create, as distinct from the main movie work, movie works from scenes in which only certain characters appear, for instance, by defining the PLs specifying these scenes. FIG. 11 shows an example of when a different PL (PL information #2) to the PL (PL information #1) shown in FIG. 10 is defined.

The greatest merit of static scenarios is being able to increase the range of a moviemaker's expression, since the variations of a movie work increase simply by defining different pieces of PL information.

There are, in addition to PLs and PlayItems, playback units in BD-ROM called Chapters. Chapters are structured from one, two, or more PlayItems.

Also, the filename "YYY" of PL information abstracts the 3-digit identification number appended to PL information in BD-ROM. That is, the PL information in FIG. 11 is uniquely identified using the identification number YYY. Expressing the identification number of PL information as "YYY" shows that this identification number is a different numbering system to the identification number XXX of the AVClip and Clip information (the 3-digit number used here is merely exemplary, and may be any number of digits).

Thus concludes the description of static scenarios. Dynamic scenarios are described next.

Dynamic Scenarios

Figure 12:
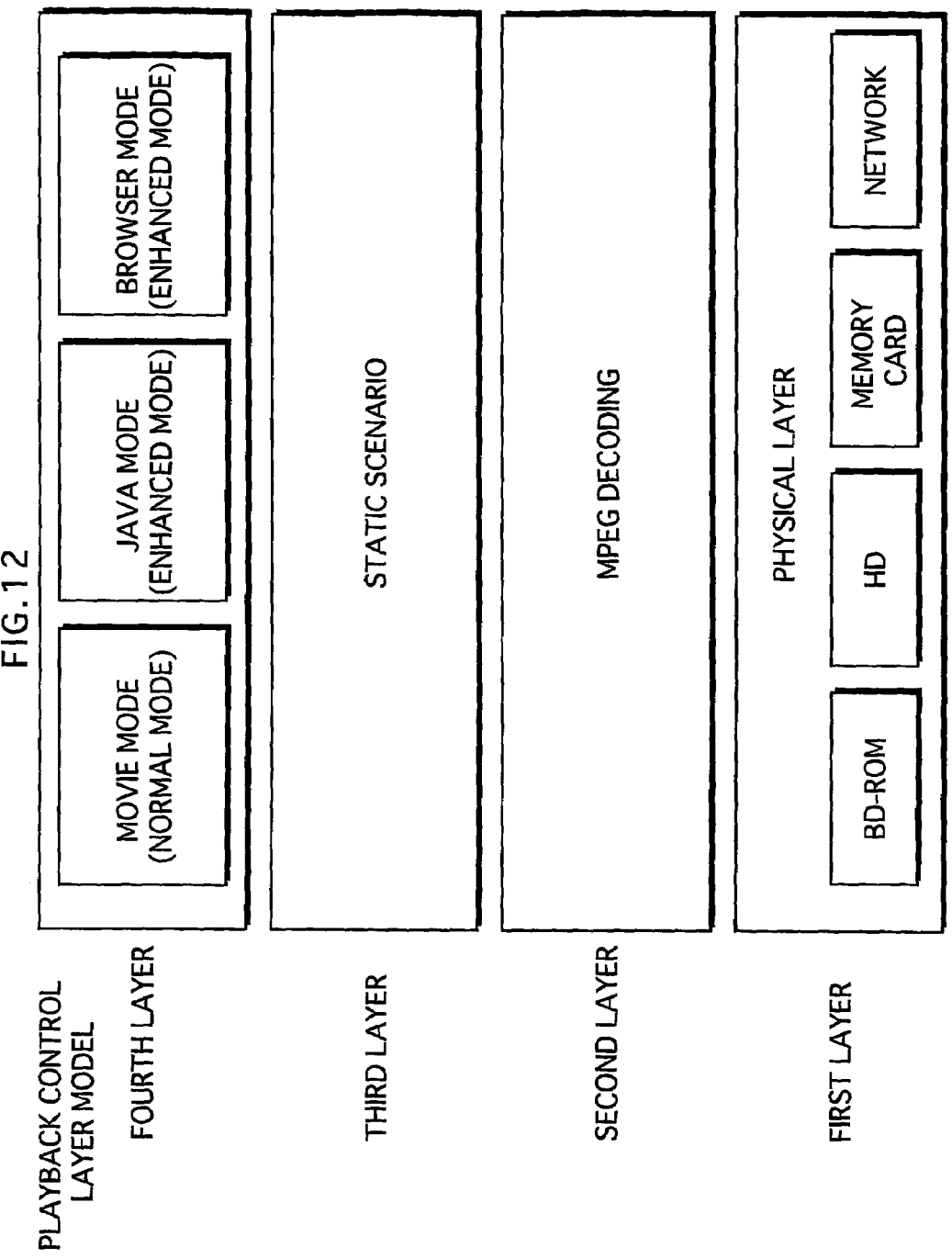
FIG. 12 shows playback modes at a fourth layer in a layer model.

Dynamic scenarios are command strings showing dynamic playback control procedures relating to AVClips. Dynamic playback control procedures change in response to user operations with respect to a device, and are similar to computer programs in character. Here, dynamic playback controls have two modes. One of the two modes is for playing video data recorded on BD-ROM (normal mode) and the other mode is for enhancing the added value of video data recorded on BD-ROM (enhanced mode) in a playback environment specific to AV devices. FIG. 12 shows playback modes on the fourth layer of the layer model. One normal mode and two enhanced modes are described on the fourth layer in FIG. 12. The normal mode, called a MOVIE mode, is a playback mode for a DVD-like environment. Of the two enhanced modes, the first, called a Java mode, is a playback mode used mainly with Java virtual machines. The second enhanced mode, called a Browser mode, is a playback mode used mainly with browsers. Since there are three modes on the fourth layer (i.e. the MOVIE mode, Java mode and Browser mode), it is preferable to describe the modes with which dynamic scenarios can be executed. When wanting to describe control commands using commands that closely resemble DVD-oriented commands, MOVIE mode playback control procedures are preferably described. In this way, it is possible to have a playback device execute playback controls that closely resemble those in existing DVD playback devices. When control procedures are described using a page description language, Browser mode playback control procedures are preferably described. As such, it is possible to describe control procedures for accessing network sites, downloading files, and the like. ZZZ.CLASS in FIG. 4 is a Java mode dynamic scenario, ZZZ.HTM is a Browser mode dynamic scenario, and ZZZ.MOVIE is MOVIE-mode dynamic scenario.

Dynamic Scenarios in MOVIE Mode

The following description relates to dynamic scenarios in MOVIE mode. MOVIE objects (ZZZ.MOVIE) are dynamic scenarios described in commands similar to those used in DVD playback devices. MOVIE objects consist of playback commands instructing PL playback, commands to be executed prior to PL playback (pre-commands), and commands to be executed after PL playback (post-commands). Pairings of one or more dynamic scenarios with PLs whose playback is instructed in the dynamic scenarios are known as Titles. Titles are units corresponding to entire movie works on BD-ROM. It should be noted that "MOVIE object" is sometimes shortened to "M-OBJ" below.

Technique for Describing Scenarios

The above dynamic scenarios can be described using functions supplied from the third layer (static scenarios). The following description relates to functions supplied from the third layer (static scenarios).

(a) Playback Functions: start playback of PlayLists specified by first arguments from positions specified by second arguments.

Format: PlayPL (first argument, second argument)

First arguments are able to specify PLs for playback using the numbers of PlayLists. Second arguments are able to specify playback start positions using PlayItems included in the PLs, and arbitrary times, Chapters and Marks in the PLs.

A PlayPL function specifying a playback start position using a PlayItem is called a "PlayPLatPlayItem( )", a PlayPL function specifying a playback start position using a Chapter is called a "PlayPLatChapter( )", and a PlayPL function specifying a playback start position using time information is called a "PlayPLatSpecified Time( )"

(b) Functions for status-acquisition and status setting of a playback device.

The status of a playback device is shown in 32 individual Player Status Registers (the setting values of these registers are called System Parameters (SPRM)), and 32 individual General Purpose Registers (the setting values of these registers are called General Parameters (GPRM)).

MOVIE objects, Java objects, and WebPage objects are able, for example, to set values in and acquire values from these registers by using the following functions (i) to (iv).

(i) "Get value of Player Status Register" Function
   Format: Get value of Player Status Register (argument)
   This function acquires setting values of Player Status Registers specified by arguments.
(ii) "Set value of Player Status Register" Function
   Format: Set value of Player Status Register (first argument, second argument)
   This function causes values specified by second arguments to be set in Player Status Registers specified by first arguments.
(iii) "Get value of General Purpose Register" Function
   Format: Get value of General Purpose Register (argument)
   This function acquires setting values of General Purpose Registers specified by arguments.
(iv) "Set value of General Purpose Register" Function
   Format: Set value of General Purpose Register (first argument, second argument)
   This function causes values specified by second arguments to be set in General Purpose Registers specified by first arguments.

The setting values (SPRM) of the Player Status Registers have the following meanings. The notation "SPRM(x)" below refers to the setting value of the $x^{th}$ Player Status Register.

SPRM(0): Reserved
SPRM(1): stream number of audio stream targeted for decoding
SPRM(2): stream number of graphics stream targeted for decoding
SPRM(3): number showing angle setting by user
SPRM(4): number of Title currently targeted for playback
SPRM(5): number of Chapter currently targeted for playback
SPRM(6): number of PL currently targeted for playback
SPRM(7): number of PlayItem currently targeted for playback
SPRM(8): time information showing current playback time
SPRM(9): count value of navigation timer
SPRM(10): number of button currently in selected state
SPRM(11)-(12): Reserved
SPRM(13): setting of parental level by user
SPRM(14): setting related to video playback of playback device
SPRM(15): setting related to audio playback of playback device
SPRM(16): language code showing audio setting in playback device
SPRM(17): language code showing subtitle setting in playback device
SPRM(18): language setting for rendering menu
SPRM(19)-(31): Reserved Of these SPRMs, SPRM(4) is updated when a Title is selected by a user via a menu operation. SPRMs(5)-(7) are updated whenever the current playback time moves forward. That is, SPRM(7) is updated if the current playback time moves from one PlayItem to another PlayItem, SPRM(6) is updated if one PL is switched for another PL, and SPRM(5) is updated if one Chapter is switched for another Chapter.

In this way, the Title and PL being played as well as the PlayItem and Chapter being played in the PL are revealed by referring to SPRMs(4)-(7).

SPRM(8), which is time information showing the current playback time (i.e. a point in time), is updated whenever picture data belonging to an AVClip is displayed. That is, if a playback device displays new picture data, SPRM(8) is updated to a value showing the display start time of the new picture data (Presentation Time).

Java objects and WebPage objects are able to find out the status of a playback device in detail by referring to the Player Status Registers using the "Get value of Player Status Register" function and the "Get value of General Purpose Status Register" function.

(c) There also exist branches from one dynamic scenario to another dynamic scenario, although these are not programming functions supplied from the third level (static scenarios). Functions for executing branches from one dynamic scenario to another dynamic scenario include the following JMP and CALL functions.

JMP function
   Format: JMP Argument
CALL function
   Format: CALL Argument

The JMP function is a branch for discarding the current dynamic scenario during operation, and executing branch-target dynamic scenario specified by an argument. JMP commands include direct reference commands that specify branch-target dynamic scenarios directly, and indirect reference commands that specify branch-target dynamic scenarios indirectly.

The Call function is a branch for causing a branch-target dynamic scenario specified by an argument to operate after suspending the operation of the current dynamic scenario, and then resuming the operation of the suspended scenario once the branch-target dynamic scenario has ended. Resume commands are placed at the end of dynamic scenarios forming the branch-targets of Call commands. Resume commands, which are the so-called Return commands of subroutines, are for reactivating dynamic scenarios that are in a suspended state due to the execution of a Call function. Call commands, as with JMP commands, include direct reference commands that specify branch-target dynamic scenarios directly, and indirect reference commands that specify branch-target dynamic scenarios indirectly.

Thus concludes the description of functions and variables supplied by the third layer (static scenario).

Figure 13:
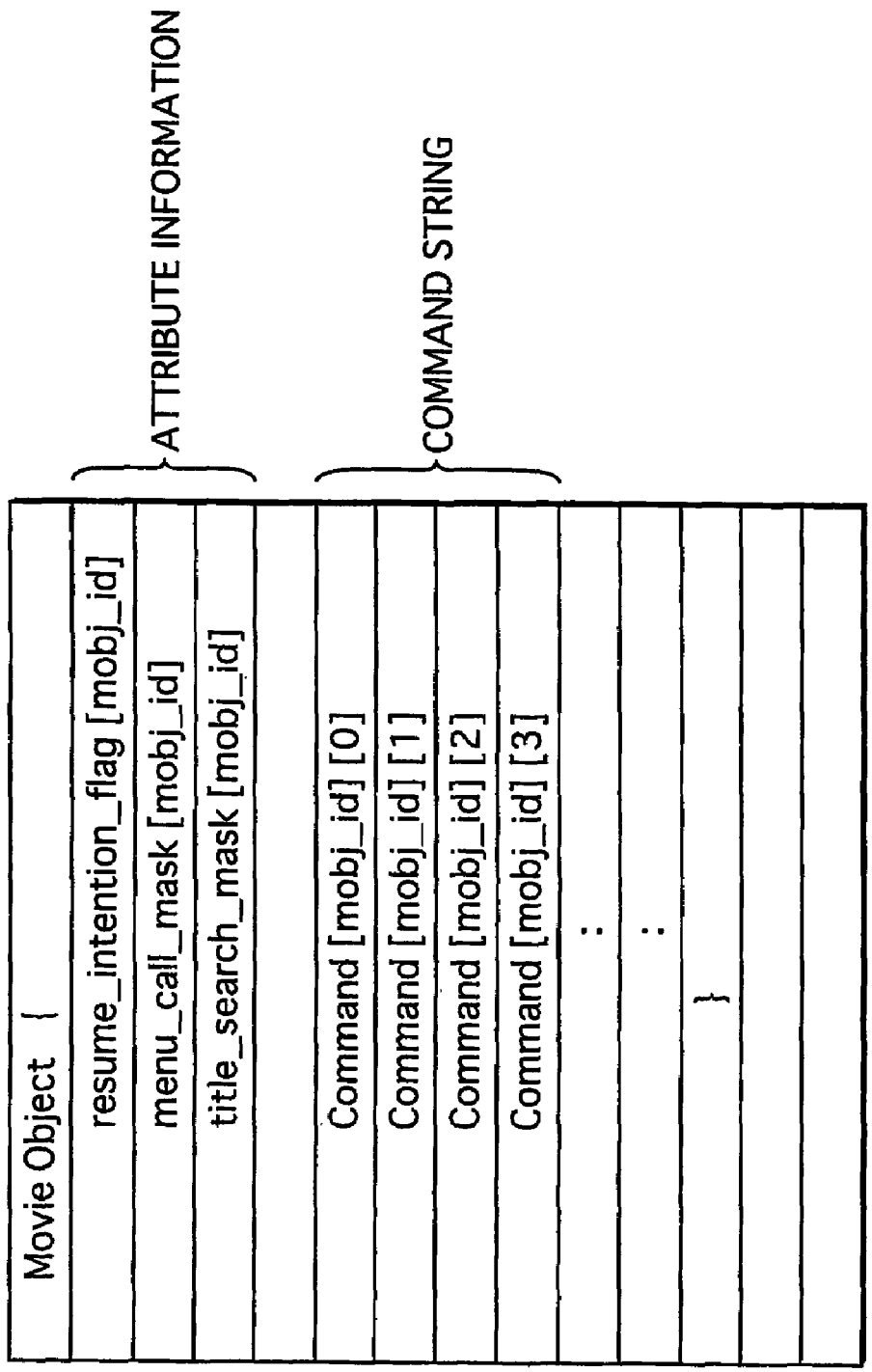
FIG. 13 shows an internal structure of a MOVIE object.

FIG. 13 shows the internal structure of a MOVIE object. A MOVIE object as shown in FIG. 13 comprises attribute information and a command string. The attribute information comprises a resume_intension_flag, a menu_call_mask, and a Title_search_mask.

The "resume_intension_flag" shows what controls the MOVIE object should perform when a menu call is requested. If the resume_intension_flag is OFF, a status-setting routine is called when a user requests a menu call. At this time, the MOVIE object currently being executed is discarded, since the resuming operation described above is riot performed. If the current MOVIE object is discarded in the playback device, playback by the playback device needs to be restarted. There are two approaches regarding which playback position to return when restarting playback. One approach involves restarting playback from a state in the current MOVIE object immediately prior to the branching.

The other approach involves restarting playback from the head of the plurality of commands structuring the current MOVIE object when the playback device has already executed some of the commands. Since the former approach involves complicated processing to recreate the pre-branching state, the present invention employs the latter approach.

The latter approach to restarting playback is performed by initializing parameters showing the execution position of the current MOVIE object and parameters showing the current playback position. That is, SPRMs(5)-(8) showing the playback position are initialized when branching to a status-setting routine as the result of a menu call. If SPRMs(4)-(8) are saved after the initialization, SPRMs(4)-(8) can be reset in the original register during the restore processing performed after the status-setting routine ends. Since SPRMs(5)-(8) have been initialized, the playback device restarts playback using the reset values.

On the other hand, if the resume_intension_flag is ON, a MOVIE object for menu-call usage is jumped to after suspending the current MOVIE object and saving the SPRMs. When processing of the MOVIE object for menu-call usage has ended, playback using the current MOVIE object is resumed after restoring the SPRMs. With MOVIE objects that realize language credits as shown in FIGS. 1A-1C, the resume_intension_flag preferably is set to OFF. This is because if a menu call is requested and the language setting is changed from English to Japanese when the playback device is on PL#2, the playback device loses the playback resumption position.

The creator is able to prevent operational errors occurring in the playback device when playback is performed by setting to OFF the resume_intension_flag piece of attribute information in MOVIE objects where there is a danger of losing the playback position as described above. In this way, the creator can feel assured in creating MOVIE objects that perform playback controls according to SPRM settings.

Since playback resumptions or restarts using the resume_intension_flag are possible in MOVIE object units, creating MOVIE objects comprising one or two commands and branching these MOVIE objects allows playback resumptions or restarts to be performed in units of one or two commands. That is, MOVIE objects preferably are created depending on the units in which playback resumption or restarting is executed. Thus concludes the description of the resume_intension_flag.

The "menu_call_mask" is a flag showing whether or not to mask menu calls. Requests for menu calls by a user are permitted if this flag is OFF and prohibited if ON.

The "Title_search_mask" is a flag showing whether or not to mask Title searches. Requests for Title searches by a user are permitted if this flag is OFF and prohibited if ON. If the current MOVIE object is for playing a trailer (preview video) or warning video by the FBI, for instance, it is possible to make sure that the user views and understands the content of this video by setting the Title_search_mask in the MOVIE object to ON.

Specific exemplary setting of the resume_intension_flag and Title_search_mask are described below. FIGS. 14A-14C show the exemplary description of a MOVIE object when realizing a language credit and playback controls resulting from this exemplary description.

In the exemplary MOVIE object description shown in FIG. 14A, resume_intension_flag, menu_call_mask, and Title_search_mask have been added to the exemplary MOVIE object description shown in FIG. 1A. The resume_intension_flag, menu_call_mask, and Title_search_mask have all been set to "0". FIG. 14B shows a playback control based on the MOVIE object described in FIG. 14A. The exemplary description in FIG. 14A realizes conditional playback such that PL#4 is played (Link(PL#4, PI#1)) if the language setting (SPRM(0)) in the playback device is "Japanese", and PL#2 is played (Link(PL#2, PI#1)) if the language setting in the playback device is anything other than "Japanese" (i.e. "else"). Here, the playback device proceeds on PL#2 if the language setting in the playback device is English.

Figure 15A:
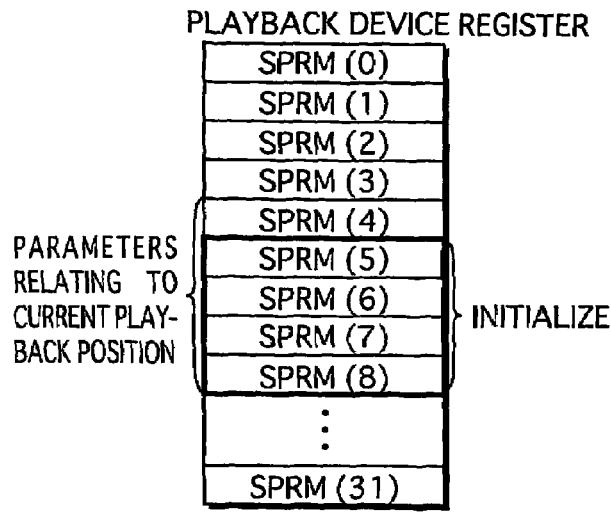
FIG. 15A-15C show processing on the side of the playback device to initiate restarting of playback.
Figure 15B:
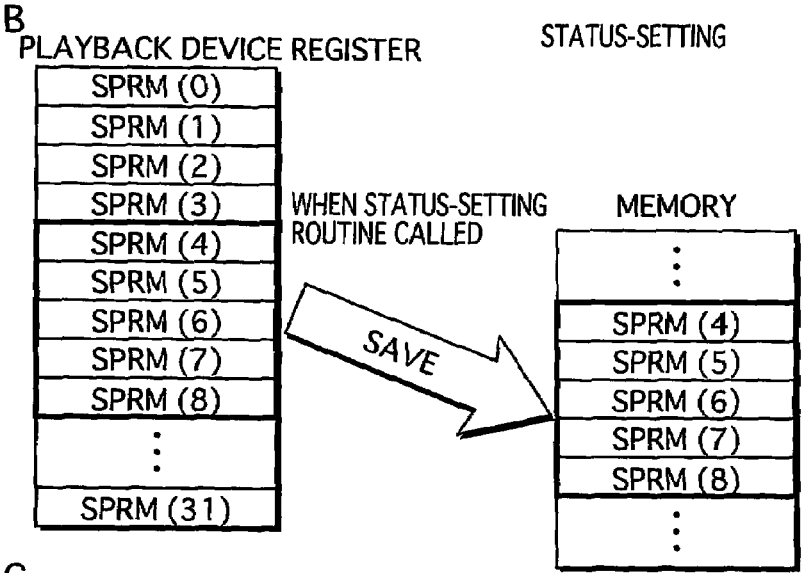
Figure 15C:
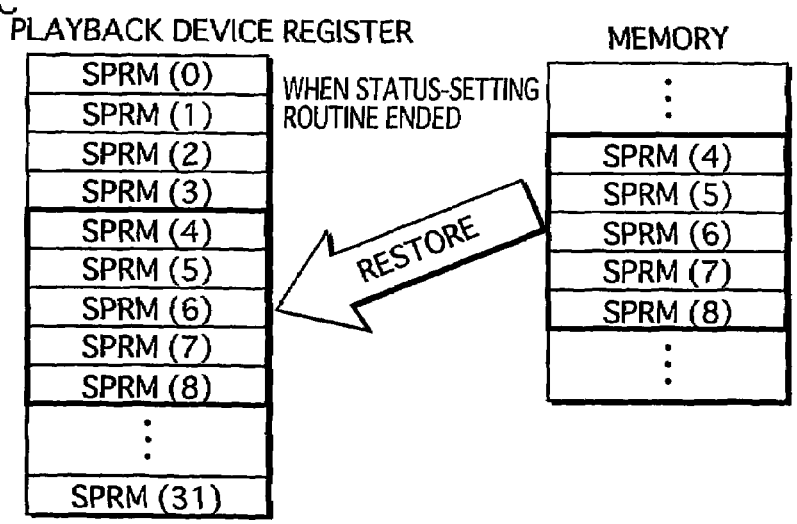

Assume that the user requests a menu call when the playback device is on PL#2 (rg1). In this case, the processing in FIGS. 15A-15C to restart playback is performed because of the resume_intension_flag in the given MOVIE object being set to "0". FIGS. 15A-15C show processing in the playback device for restarting playback. If the resume_intension_flag is set to "0", SPRMs(4)-(8) showing the playback position are saved to memory (FIG. 15B) after initializing SPRMs(5)-(8) (FIG. 15A). A branch br1 to a status-setting routine rc1 is executed after SPRMs(4)-(8) have been saved. Assume that the user changes the language setting from English to Japanese using this status-setting routine (English→Japanese in FIG. 15B). Once processing of the status-setting routine has ended, the playback device restores SPRMs(4)-(8) saved in memory to the register. Since the initialized SPRMs(5)-(8) showing the playback position are set in the register, the playback position is set to the head of the Title in FIG. 14B. As a result, restarting from the head of the Title is carried out. Moreover, in the FIG. 14C example, the playback position is set to the Title head because of the playback device not initializing SPRM(4), which shows the number of the Title currently being played. If this Title number is initialized, playback is restarted from a Title menu that encourages the user to select a Title.

A further exemplary description is shown FIGS. 16A-16C.

FIGS. 16A-16C show the exemplary description of a MOVIE object when realizing branching that results from a question, and playback controls resulting from this exemplary description. The exemplary MOVIE object description shown in FIG. 16A differs from that shown in FIG. 14A in that FIG. 16A realizes dialogue playback controls, whereas FIG. 14 realizes a language credit. In FIG. 16A, PL#1 is a question scene, and PL#2 and PL#4 are scenes that appear when answers (1) and (2) are respectively selected in response to the question. Which answer to select is set in GPRM(0). Playback switching resulting from IF statements, is performed according to GPRM(0). GPRM(0), which is merely a general-purpose register value, is not updated in response to the setting of status-setting routines. Also, in this exemplary description, resume_intension_flag is set to "1".

FIG. 16B shows a playback control based on the MOVIE object described above.

Assume that the user requests a menu call when the playback device is on PL#2. In this case, the playback device omits FIG. 15A and performs the FIG. 15B processing because of the resume_intension_flag in the given MOVIE object being set to "1". That is, SPRMs(4)-(8) showing the playback position are saved from the register to memory. Branch br1 to status-setting routine rc1 is executed after SPRMs(4)-(8) have been saved. Assume that the user changes the language setting from English to Japanese using this status-setting routine (English→Japanese in FIG. 16B). Once processing of the status-setting routine has ended, the playback device executes processing to restore SPRMs(4)-(8) from memory to the register. Since SPRMs(4)-(8) are set in the register as a result of the restoration, the playback position is such that playback is resumed from the previous playback position.

A further exemplary MOVIE object is shown in FIGS. 17A-17C. If SPRM(13), which is the parental level setting in the playback device, is "kids" in the MOVIE object shown in FIG. 17A (if (SPRM(13)=="kids")), PL#4 (Link(PL#4, PL#1)) is played, and if the parental level in the playback device is any other setting apart from "kids" (i.e. "else"), PL#2 (Link(PL#2,PL#1)) is played. Here, it is possible to realize a so-called parental lock, since playback switches between extreme scenes and child-oriented scenes depending on the SPRM(13) setting when PL#2 and PL#4 are assumed to be an extreme scene and a child-oriented scene, respectively. Since SPRM(13) can be changed using a status-setting routine, the resume_intension_flag in the attribute information is set to "0".

FIG. 17B shows a playback control by the MOVIE object described above. This playback control is for setting SPRM (13) in the playback device to "kids". PL#4 is thus played since even SPRM(13) in the playback device is set to show "kids" (Link(PL#4,PL#1)).

Assume that a menu call is requested when the playback device is on PL#4. Since the resume_intension_flag is set to "0" in FIG. 17A, SPRMs(4)-(8) are saved (FIG. 15B) after initializing SPRMs(5)-(8) (FIG. 15A). Branching to the status-setting routine is then executed.

Assume here that in this status-setting routine an operation is performed to update SPRM(13) and the status-setting routine has ended. Since SPRMs(4)-(8) are returned to the register in the playback device in the restoration performed after the end of the status-setting routine (FIG. 15B), the playback position is set to the head of the Title and playback is restarted from this position (FIG. 17C).

The examples shown above in FIGS. 14, 16 and 17 are examples involving the resume_intension_flag setting. FIGS. 18A-18B show an example of Title_search_mask being set in MOVIE objects.

MOVIE object (0) in FIG. 18A is the MOVIE object executed prior to MOVIE object (1) shown in FIG. 14A. In this MOVIE object, PL#6 is a preview (1), PL#7 is a preview (2), and PL#5 is video for having the user select one of PL#6 and PL#7. Which of the preview is selected is set in GPRM (0). Playback switching by an IF statement is performed according to GPRM(0). Jmp Movie Object (1) is a branch command executed after the switching, MOVIE object (1) being the branch target. Since Title_search_mask in MOVIE object (1) is set to "1", Title search requests are masked while playback controls are being performed by the MOVIE object. Conversely, a Title search will be activated if either of previews (1) and (2) is viewed (FIG. 18B). Since a control is realized to "prohibit title searches until either of previews (1) and (2) is viewed" by merely setting a 1-bit Title_search_mask, freedom in describing the control is increased. Let us draw a comparison with when the same playback controls as in FIG. 18B are performed using Japanese patent application no. 2856363. According to Japanese patent application no. 2856363, the permissibility of user operations is set with respect to individual playback path, which means that when there is a large number of previews that can be played alternately, the number of playback paths set to prohibit user operations must equal that number. As such, the number of playback paths that must be provided increases with the number of playable previews, thus inviting complications.

In contrast, with the MOVIE object in FIGS. 18A-18B, a playback control for refusing Title searches until a preview is played can be described simply by setting the Title_search_ mask in the MOVIE object to "1", even when there is a large number of alternately playable previews.

Because of the easy description of this playback control, MOVIE objects pertaining to the present embodiment are effective when distributing Titles.

Figure 19:
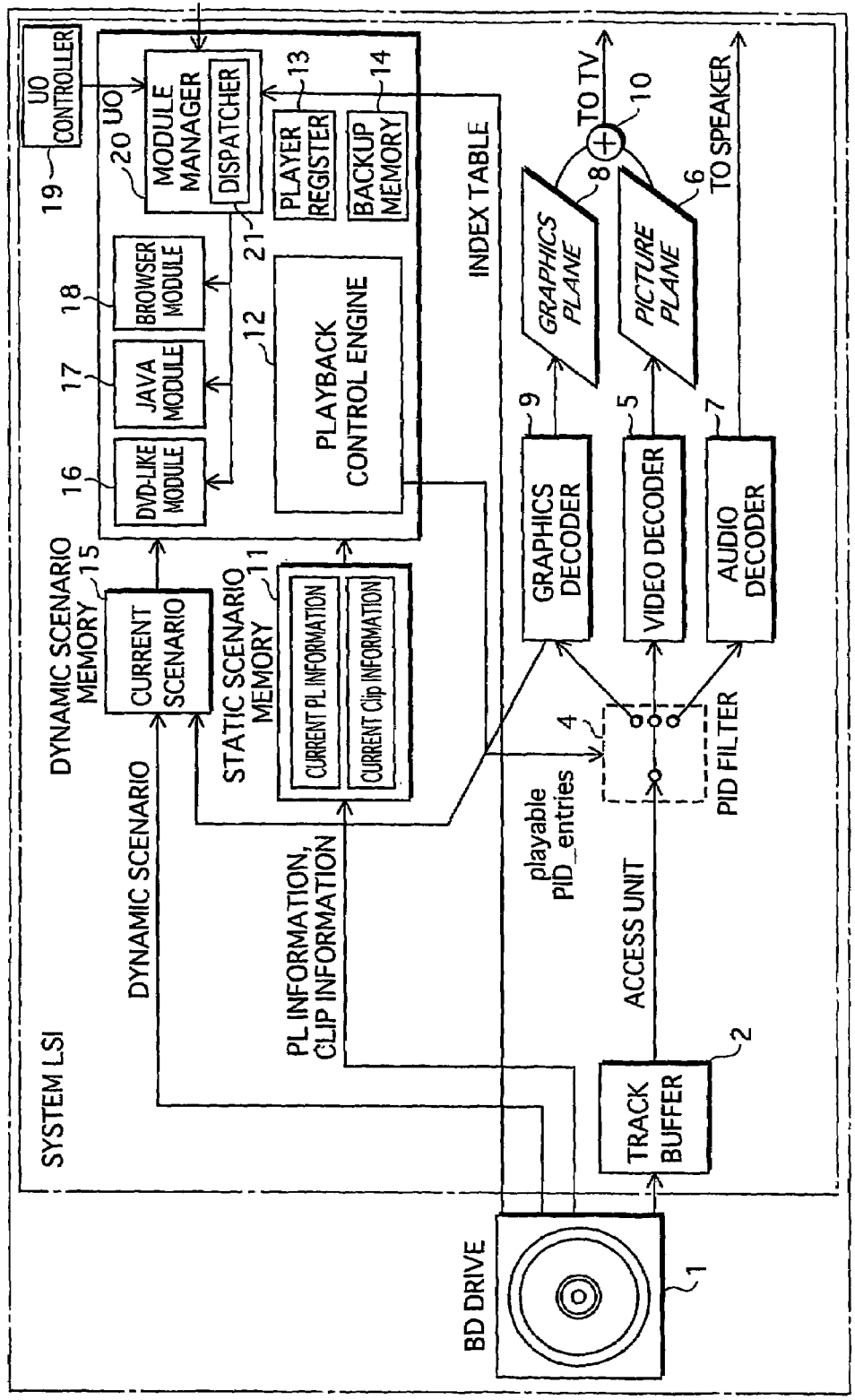
FIG. 19 shows an internal structure of a playback device pertaining to the present invention.

Thus concludes the description relating to an embodiment of a recording medium pertaining to the present invention. The following description relates to an embodiment of a playback device pertaining to the present invention. FIG. 19 shows the internal structure of a playback device pertaining to the present invention. A playback device pertaining to the present invention comprises two main parts, namely, a system LSI and a drive device, and can be produced industrially by mounting these parts to the cabinet and substrate of a device. The system LSI is an integrated circuit that integrates a variety of processing units for carrying out the functions of the playback device. A playback device thus produced is structured from a DVD drive 1, a track buffer 2, a PID filter 4, a video decoder 5, a picture plane 6, an audio decoder 7, a graphics plane 8, a graphics decoder 9, an adder 10, a static scenario memory 11, an playback control engine 12, a player register 13, a BACKUP memory 14, a dynamic scenario memory 15, a DVD-like module 16, a Java module 17, a BROWSER module 18, a UO controller 19, a module manager 20, and a dispatcher 21.

BD-ROM drive 1 performs loading/ejecting of BD-ROMs, and accesses loaded BD-ROMs.

Track buffer 2 is a FIFO memory that stores ACCESS UNITs read from BD-ROMs on a first-in first-out basis.

PID filter 4 retrieves ACCESS UNITs from track buffer 2 and converts TS packets structuring ACCESS UNITs into PES packets. Desired PES packets obtained as a result of the conversion are outputted to one of video decoder 5, audio decoder 7, and graphics decoder 9. The outputting is performed while referring to the IDs (PIDs) of the PES packets. PES packets whose PID shows video are outputted to video decoder 5, PES packets whose PID shows audio are outputted to audio decoder 7, and PES packets whose PID shows graphics image are outputted to graphics decoder 9.

Video decoder 5 writes uncompressed-format pictures obtained by decoding the plurality of PES packets outputted from PID filter 4 to picture plane 6.

Picture plane 6 is a memory for storing uncompressed-format pictures.

Audio decoder 7 outputs uncompressed-format audio data obtained by decoding PES packets outputted from PID filter 4.

Graphics plane 8 is a memory having a single screen capacity area that can stores one screen worth of graphics images.

Graphics decoder 9 writes raster images obtained by decoding graphics streams to graphics plane 8. Subtitles, menus and the like appear on a screen as a result of decoding graphics streams.

Adder 10 outputs the result of synthesizing images expanded in graphics plane 8 with uncompressed-format picture data stored in picture plane 6.

Static scenario memory 11 is a memory for storing current PL information, Clip information, and the like. Current PL information is the piece currently targeted for processing from among the plurality of PL information recorded on the BD-ROM. Current Clip information is the piece currently targeted for processing from among the plurality of Clip information recorded on the BD-ROM.

Playback control engine 12 executes various functions, such as AV playback functions (1), PlayList playback functions (2), and status-acquisition/setting functions (3) in the playback device. AV playback functions in the playback device, which consist of a function group similar to that found in DVD and CD players, refer to the execution in response to user operations of processing such as Play, Stop, Pause-On, Pause-Off, Still-Off, Forward Play (fast), Reverse Play (fast), Audio Change, Subtitle Change, and Angle Change. PL playback functions refer to the execution of Play, Stop and other of the AV playback functions in accordance with PL information. Playback control engine 12 carries out the functions of the third layer (playback controls based on static scenarios) in the layer model by executing these PL playback functions. On the other hand, playback control engine 12 executes functions (2) to (3) in accordance with function calls from DVD-like module 16, Java module 17, and BROWSER module 18. That is, playback control engine 12 executes the functions of playback control engine 12 in response to instructions resulting from user operations and instructions from superordinate layers in the layer model.

Player register 13 comprises 32 individual System Parameter Registers and 32 individual General Purpose Registers. The stored values of these registers are used in programming as SPRMs and GPRMs. Since System Parameter Registers and General Purpose Registers are managed by playback control engine 12, which is separate from modules 16 to 18, it is possible, even when a change in playback modes occurs, for instance, for the module that executes the playback mode after the switch to find out the playback status of the playback device simply by referring to SPRMs(0)-(31) and GPRMs (0)-(31) in playback control engine 12.

BACKUP memory 14 is a stack memory for saving stored values of the playback device register when one of modules 16 to 18 executes Suspend. The stored values of BACKUP memory 14 are restored to the stored values of the register possessed by the playback device when one of modules 16 to 18 executes Resume in a dynamic scenario. The stored values of registers are stored in a first-in first-out basis in the event that one of modules 16 to 18 performs Suspend two or more times. If the number of stored values is greater than or equal to the number of slots in the stacks, stored values that have been saved are overwritten. SPRMs saved to BACKUP memory 14 includes the number of the Title currently being played (Title Number), the currently-being-played Chapter number, the currently-being-played PL number (PlayList Number), the currently-being-played PlayItem number (PlayItem Number), the number of the button in a selected-state (Selected Button), and time information showing the current playback time.

Dynamic scenario memory 15 is a memory storing the current dynamic scenario, and is jointly processed by DVD-like module 16, Java module 17 and BROWSER module 18. The current dynamic scenario is the dynamic scenario currently targeted for processing from among the plurality of scenarios recorded on the BD-ROM.

DVD-like module 16, which is a DVD virtual player that is the main execution body of MOVIE mode, executes current MOVIE objects read to dynamic scenario memory 15.

Java module 17 is a Java platform formed from a Java virtual machine, a configuration and a profile.

Java module 17 creates current Java objects from ZZZ.CLASS files read to dynamic scenario memory 15, and executes the current Java objects. The Java virtual machine converts Java objects described using a Java language into native codes for the CPU in the playback device, and has the CPU execute the native codes.

BROWSER module 18, which is a browser that is the main execution body of Browser mode, executes current WebPage objects read to dynamic scenario memory 15.

UO controller 19 detects user operations performed with respect to a remote controller, a front panel of the playback device or the like, and outputs information showing detected user operations (hereinafter "UO information") to module manager 20.

Module manager 20 holds an Index Table read from the BD-ROM and performs mode management and branch controls. Mode management performed by module manager 20 refers to the allocation of modules; namely, which of modules 16 to 20 is to execute what dynamic scenarios. The principle of module allocation is that DVD-like module 16 executes dynamic scenarios. This principle is upheld even if in the case of branches resulting from intra-modes (i.e. branches within the same mode). An exception is when inter-mode branching occurs (i.e. branching between modes). When branching from a MOVIE object to a java object/Webpage object occurs, Java module 17 and BROWSER module 18 respectively execute the current object.

Dispatcher 21 chooses only UOs apposite to the current mode of the playback device, and passes chosen UOs on to the module for executing the current mode. For example, if arrow key or activate UOs are received during the execution of MOVIE mode, dispatcher 21 outputs these UOs to the module executing MOVIE mode. These UOs are only required for menu behavior in MOVIE mode, and are not required by Java and Browser modes.

Thus concludes the description of the playback device elements. Module manager 20 will now be described in detail.

Figure 20:
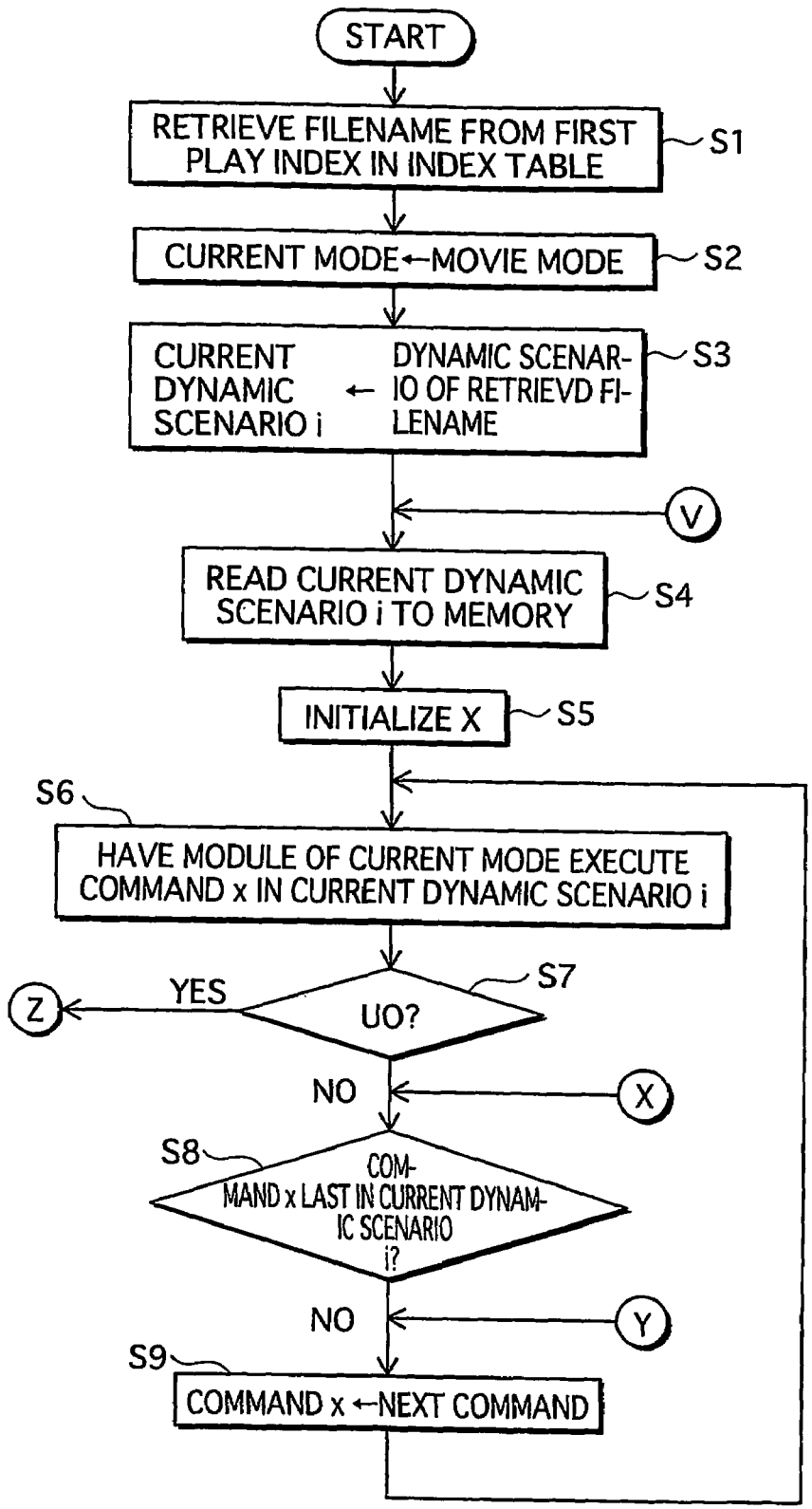
FIG. 20 is a flowchart showing processing procedures performed by a module manager 20.
Figure 21:
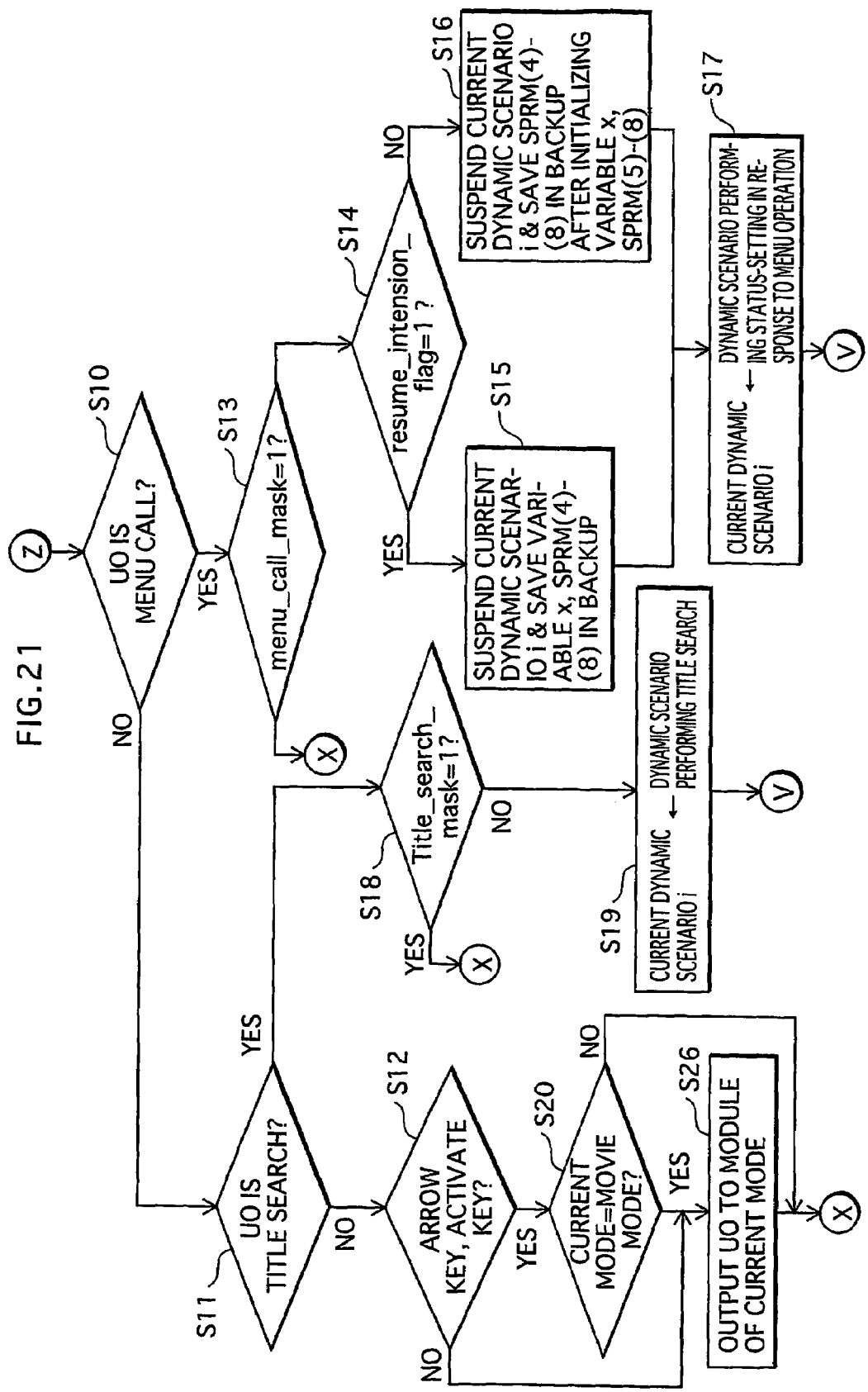
FIG. 21 is a flowchart showing processing procedures performed by module manager 20.
Figure 22:
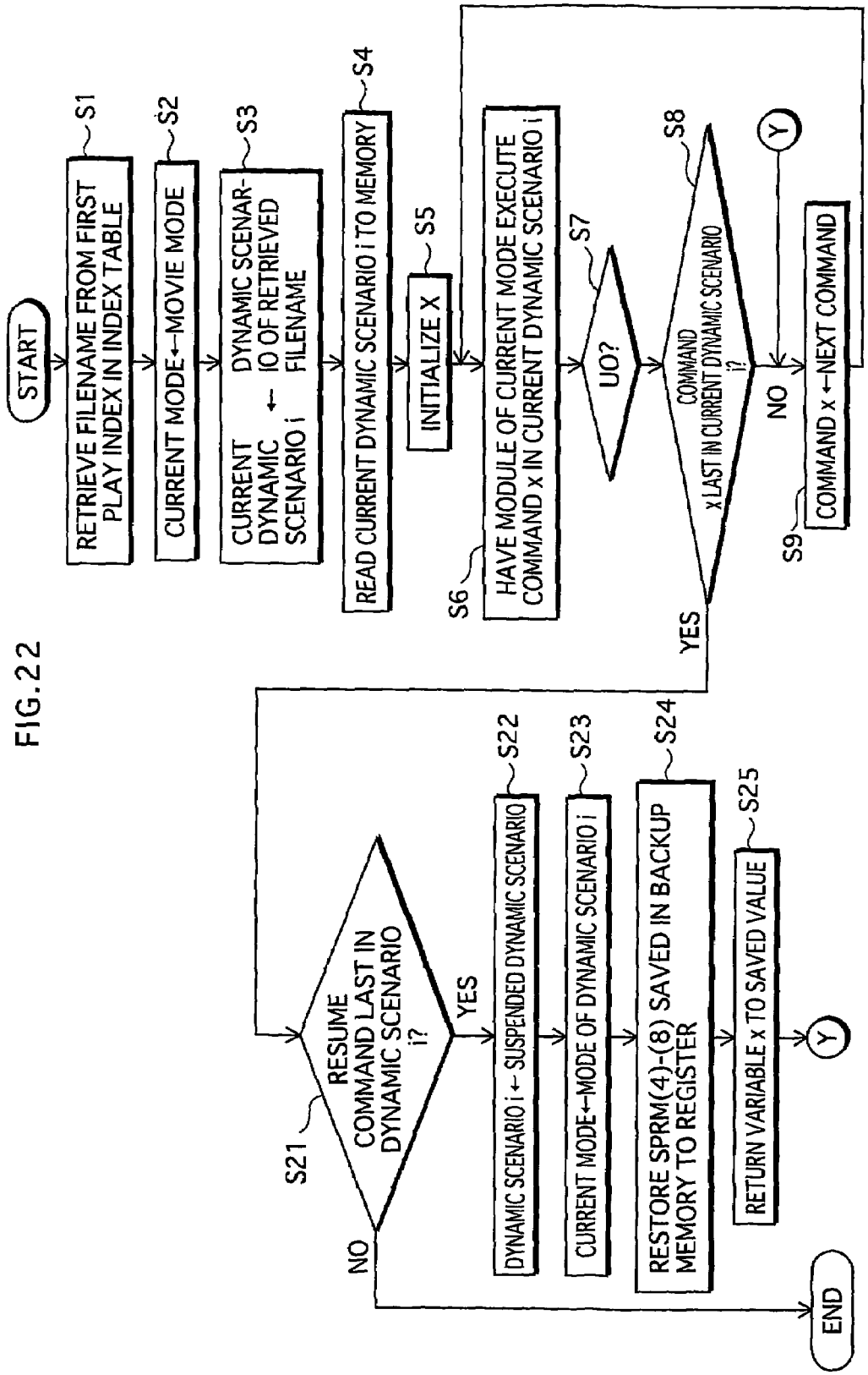
FIG. 22 is a flowchart showing processing procedures performed by module manager 20.

Module manager 20 can be implemented by having a general purpose CPU read programs for performing the processing procedures shown in FIGS. 20 to 22. FIGS. 20 to 22 are flowcharts showing the processing procedures performed by module manager 20. Branch controls performed by module manager 20 will now be described while referring to these flowcharts. In the FIG. 20 flowchart, module manager 20 retrieves a filename from the First Play Index in the Index Table (step S1). The Index Table is integrated information relating to MOVIE objects, and the First Play Index is an Index showing MOVIE objects that describe BD-ROM startup procedures.

Once the filename has been retrieved, module manager 20 sets the current mode to MOVIE mode (step S2), sets the dynamic scenario of the retrieved filename as the current dynamic scenario (step S3), reads the current dynamic scenario i to memory (step S4), and executes current dynamic scenario in memory (steps S5-S9).

Steps S4 to S9 are executed whenever the current dynamic scenario is newly set.

Steps S5 to S9 form a loop processing procedure in which the processing of steps S6 to S9 is repeated for each command structuring a scenario. The "x" in the flowcharts is a variable that identifies processing targets from among the commands structuring a dynamic scenario. The loop processing involves module manager 20 repeating the following processing: initializing variable x (step S5), having the module of the current mode execute command x included in the current dynamic scenario i (step S6), performing the judgment processing defined in steps S7 to S8, and then incrementing variable x (step S9), before returning the step S6. The processing of steps S6 to S9 is repeated for all of the commands structuring the scenario.

If a UO occurs during execution of the loop processing (step S7=YES), module manager 20 outputs the UO to the module executing the current mode (step S26) after passing though the judgment processing of steps S10 to S12.

Step S10 is a step for judging whether the user operation is a menu call. If a menu call, module manager 20 performs the save processing of one of steps S15 and S16 in FIG. 21 after passing through the judgments of steps S13 and S14. Module manager 20 then sets a dynamic scenario for performing status setting as the current dynamic scenario i (step S17), and returns to step S4. Since a dynamic scenario for performing status setting becomes the current dynamic scenario i as a result of step S17, the dynamic scenario for status setting is executed at steps S5 to S9.

Step S13 is a judgment as to whether the menu_call_mask in the current dynamic scenario i is "1". If "1", module manager 20 returns to step S8 in FIG. 20 without performing any processing.

Step S15 is processing to suspend the current dynamic scenario i and save variable x and SPRMs(4) to (8) in BACKUP memory 14. Step S15 is executed if the resume_intension_flag is "1" (step S14=YES).

Step S16 is processing to suspend the current dynamic scenario i and save variable x and SPRMs(4) to (8) in BACKUP memory 14 after initializing variable x and SPRMs (5) to (8). Step S16 is executed if the resume_intension_flag is "0" (step S14=NO).

Step S11 is a judgment as to whether the user operation requests a Title search. If a Title search is requested, module manager 20 judges in step S18 whether the Title_search_mask of the current dynamic scenario i is "1". If "1", module manager 20 sets a dynamic scenario for performing title searches as the current dynamic scenario i in step S19.

Step S12 is for executing dispatch processing of the UO. Dispatch processing of a UO involves module manager 20 judging whether a UO that occurs during command execution is an arrow key or activate operation (step S12), and if the current mode is MOVIE mode (step S20), outputting the UO to the module that executes the current mode. If the UO that occurred during command execution is other than an arrow key or activate operation, the UO is simply outputted to the module that executes the current mode (step S26). If the UO that occurred during command execution is an arrow key or activate operation but the current mode is not MOVIE mode, the UO is not outputted to a module. Thus concludes the description of dispatch processing.

The requirement for ending the loop processing of steps S4 to S19 is that judgment in step S8 be YES. If the command x is the final command in dynamic scenario i (step S8=YES), a judgment is conducted as to whether a Resume command is last in dynamic scenario i (step S21 in FIG. 22).

A Resume command is a command instructing the playback device to perform status-restoration of the dynamic scenario that is the call source. Resume commands are placed at the end of dynamic scenarios for status setting (i.e. status-setting routines).

If a Resume command exists at the end of dynamic scenario i, module manager 20 sets the suspended dynamic scenario as dynamic scenario i (step S22), sets the mode of dynamic scenario i as the current mode (step S23), restores the SPRMs saved in BACKUP memory 14 to the register (step S24), and returns variable x to the saved value (step S25).

Here, since SPRMs(4)-(8) and variable x are saved to memory 14 after being set to values showing the playback position up until that point in time if the resume_intension_flag is "1", the player register shows the playback position prior to the call for a status-setting routine as a result of the restore processing performed at step S24. Processing to resume Title playback is performed because of these values being set in the player register.

On the other hand, since SPRMs(4)-(8) and variable x are saved to memory 14 after SPRMs(5)-(8) and variable x have been initialized if the resume_intension-flag is "0", the player register shows the playback start position of the Title currently being played. Processing to restart the Title is performed because of these values being set in the player register. It should be noted that although in the flowcharts of FIGS. 20 to 22 the restart is executed from the Title currently being played, the restart may be performed with respect to the entire BD-ROM by initializing all SPRMs showing playback positions at step S16. Thus concludes the description of processing procedures performed by module manager 20.

According to the present embodiment as described above, control procedures pertaining to menu calls at an upper-most layer (dynamic scenarios) are set in a layer mode comprising, from bottom to top, streams, playback paths, and dynamic scenarios. In particular, when Titles that the user wants to create are for realizing language credits, it is possible to realize controls in which menu calls are accepted but playback is not resumed. As a result, it is possible to easily create two types of Titles, namely, those that permit menu calls and those that prohibit menu calls, even with the same streams and playback paths. Since there is no increase in the number of playback paths and streams with the creation of Titles, it is possible with little effort to increase the number of variations having different control procedures.

Embodiment 2

Embodiment 2 relates an enhancement that allows Stop and Restart in a playback device to be avoided. Stop and Restart in a playback device can occur when any of the following three situations arise in the playback device.

1) When branching to a Java object or a WebPage object occurs with a BD-ROM corresponding to Java mode and Browser mode loaded in a playback device corresponding only to MOVIE mode.

2) When attempting to read a non-existent stream, or attempting to branch to a Title structured from a non-existent dynamic scenario.

3) When recovering an error that occurs with a Java object is not possible.

With the present embodiment for avoiding Stop and Restart, an INDEX relating to Titles for use in exception processing is provided in information for integrating/managing dynamic scenarios.

INFO.BD shown in FIG. 4 is information for integrating/managing dynamic scenarios in MOVIE mode, Java mode, and Browser mode.

FIG. 23A shows an internal structure of INFO.BD. As shown in FIG. 23A, INFO.BD includes an Index Table. The Index Table is an indirect reference table that is referenced when branching from one dynamic scenario to another dynamic scenario, and comprises Indexes corresponding one-to-one with a plurality of labels. In each Index is described a filename of a dynamic scenario corresponding the label of the Index. As shown in FIG. 23B, Each filename comprises a file body and an extension. The labels include Title#1~#m, Title#m+1~#n, and Title#0. The Index Table is also referred to from dynamic scenarios of any of the three modes. Branching from MOVIE objects to Java objects or from MOVIE objects to WebPage objects is only possible when via the Index Table. To rephrase, it is not possible to branch from a MOVIE object to a Java or WebPage object that does not have an Index in the Index Table.

The TITLE#1~#m Indexes relate to the $1^{st}$ to $m^{th}$ Titles entered in the BD-ROM. In these Indexes are described the filenames of MOVIE objects that are to be branch targets when the $1^{st}$ to $m^{th}$ Title numbers are selected. FIG. 23B shows the content of TITLE#1~#m. As shown in FIG. 23B, the filenames of MOVIE objects are described in the Title#1·#m Indexes. Each filename comprises a file body (ZZZ) and an extension (.MOVIE).

The TITLE#m+1~#n Indexes relate to the $1^{st}$ to m+$1^{th}$ Titles entered in the BD-ROM. In these Indexes are described the filenames of WebPage objects/Java objects that are to be the branch target when the m+1th to nth Title numbers are selected. FIG. 23C shows an internal structure of the TITLE#m+1~#n Indexes. As shown in FIG. 23C, in each of Indexes TITLE#m+1~#n is stored either the file body (ZZZ) and extension (.CLASS) of a Java object or the file body (ZZZ) and extension (.HTM) of a WebPage object. It should be noted that Index format may be as shown in FIG. 23D; The Index in the FIG. 23D format has an attribute area showing an attribute of the branch-target Title, the Index being structured to show in the attribute area whether the dynamic scenario of the corresponding branch-target Title is MOVIE mode ("00" setting), Java mode ("01" setting), or Browser mode ("10" setting).

TITLE#0INDEX relates to an exception processing Title, and stores the filename of a MOVIE mode scenario. The exception processing described here is executed when any of the above three situations arises. A playback device in which enhanced mode execution is not possible for any of these three reasons is called a core system. On the other hand, a playback device in which program execution using a Java virtual machine or a Browser is possible is called a full system. Indirect referencing of a BD-ROM by a core system and a full system is described below while referring to FIGS. 24A-24B. The description of indirect referencing assumes a BD-ROM on which a plurality of dynamic scenarios is recorded (001.MOVIE, 002.MOVIE, 003.MOVIE, ..., 001.CLASS, 002.CLASS, 003.CLASS, ...), as shown in FIG. 24A. FIG. 24B shows an exemplary description of an Index Table when the plurality of dynamic scenarios shown in FIG. 24A is recorded on the BD-ROM. In the exemplary description shown in FIG. 24B, the filenames of MOVIE mode scenarios (001.MOVIE, 002.MOVIE, 003.MOVIE, ...) are described in Title#1Index to Title#mIndex. On the other hand, the filenames of enhanced mode scenarios (001.CLASS, 002.CLASS, 003.CLASS, ...) are described in Title#m+1Index to Title#nIndex.

Figure 25A:
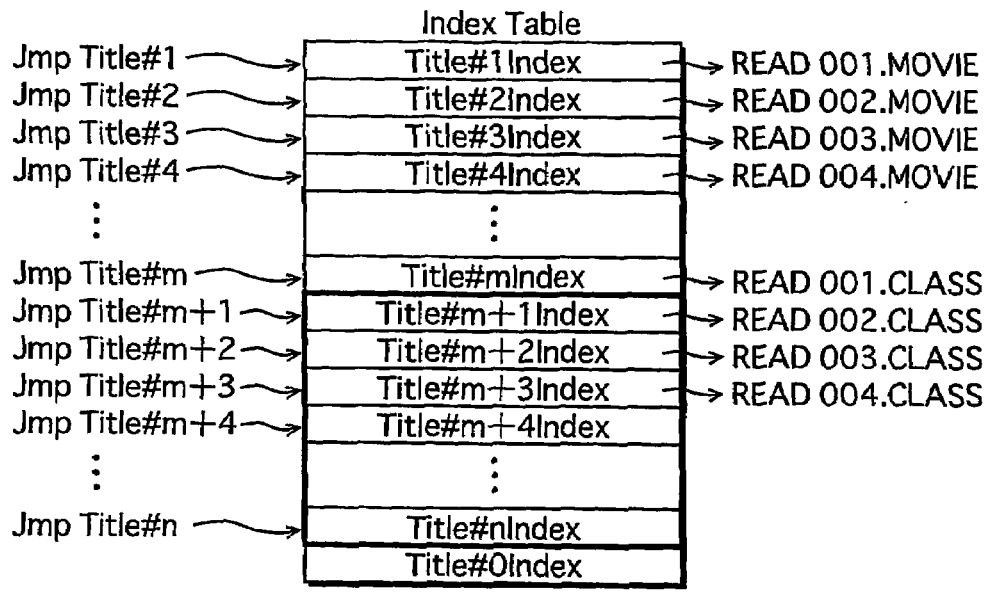
FIG. 25A shows indirect referencing in a full system when the Index Table is as shown in FIG. 24B.

FIG. 25A shows indirect referencing in a full system when the Index Table is described as in FIG. 24B. Because of the Index Table being described as such, filenames "001.MOVIE, 002.MOVIE, 003.MOVIE, ..." are retrieved from Title#1Index to Title#mIndex when executing branch commands specifying labels Title#1 to Title#m as branch targets, and filenames "001.CLASS, 002.CLASS, 003.CLASS, ..." are retrieved from Title#m+1Index to Title#nIndex when executing branch commands specifying labels Title#m+1 to Title#n as branch targets. Dynamic scenarios specified by these filenames are then read to memory and executed. Thus concludes the description of indirect referencing by a full system.

Figure 25B:
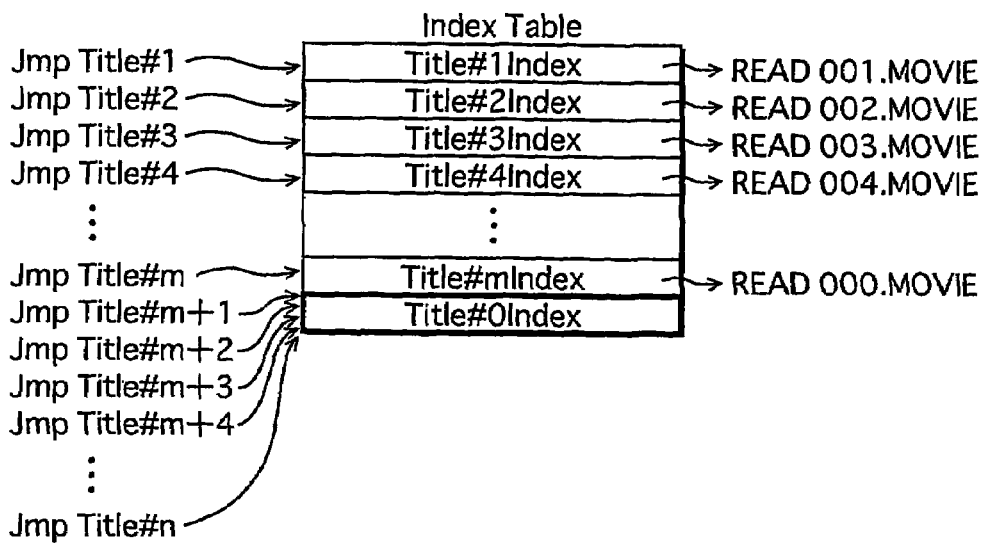
FIG. 25B shows indirect referencing in a core system.

FIG. 25B shows indirect referencing in a core system. Filenames "001.MOVIE, 002.MOVIE, 003.MOVIE, ..." are retrieved from Title#1Index to Title#mIndex when executing branch commands specifying labels Title#1 to Title#m as branch targets. However, when executing branch commands specifying labels Title#m+1 to Title#n as branch targets, filename "000.MOVIE" is retrieved from Title#0Index in place of Title#m+1Index to Title#nIndex. The playback device then executes the dynamic scenarios specified by these filenames. Thus concludes the description of indirect referencing by both a full system and a core system.

FIG. 26 schematically shows how branching from a MOVIE object to a Java object is performed. The MOVIE object in FIG. 26 comprises a pre-command in which GPRM (0) is set to "0", a command (PlayPL(PL#1)) instructing the playback device to perform PL playback, and a post-command instructing the playback device to perform branching to another dynamic scenario (IF(GPRM(0)=0){Jmp Title#m}else{Jmp Title#m+1}). As a result of this pre-command, GPRM(0) is initialized prior to PL playback. Also, as a result of this post-command, branching is performed to MOVIE object#m+1 if GPRM(0) shows "0" when initialized. On the other hand, branching is performed to another Title (Title#m) if a button selection is performed when a menu is displayed and GPRM(0) is set to a value other than "0".

Interactive graphics streams for realizing dialogue processing as described below are multiplexed onto AVClips. Interactive graphics streams are streams displaying buttons corresponding to characters A, B and C, GPRM(0) being set to "1" when character A is determined, "2" when character B is determined, and "3" when character C is determined.

The arrows jn1 and jn2 in FIG. 26 symbolically indicate the branching from a MOVIE object to a Java object. Jmp Title#m+1 in FIG. 26 is a branch command in a Java object, and specifies the Java object as a branch target using an indirect referencing format via the Index of label Title#m+1. The filename of the Java object is described in the Index of label Title#m+1, the playback device being able to find out which file to read as the Java object by referring to this Index.

In the Java object, "A.drawcharacter ( );" means that the Object of character A is drawn on the screen using one of the methods (i.e. the drawCharacter function in FIG. 26) of the Class "character A". Likewise, "B.drawcharacter( );" and "C.drawcharacter( );" mean respectively that the Objects of characters B and C are drawn on the screen using one of the methods (i.e. the drawCharacter function in FIG. 26) of the Classes "character B" and "character C".

Since "A.drawCharacter ( );", "B.drawcharacter( );" and "C.drawcharacter( );" are executed exclusively depending on the value of GPRM(0) (IF statements in FIG. 26), the CG of character A is drawn if GPRM(0) is "1", the CG of character B is drawn if GPRM(0) is "2", and the CG of character C is drawn if GPRM(0) is "3".

Figure 27:
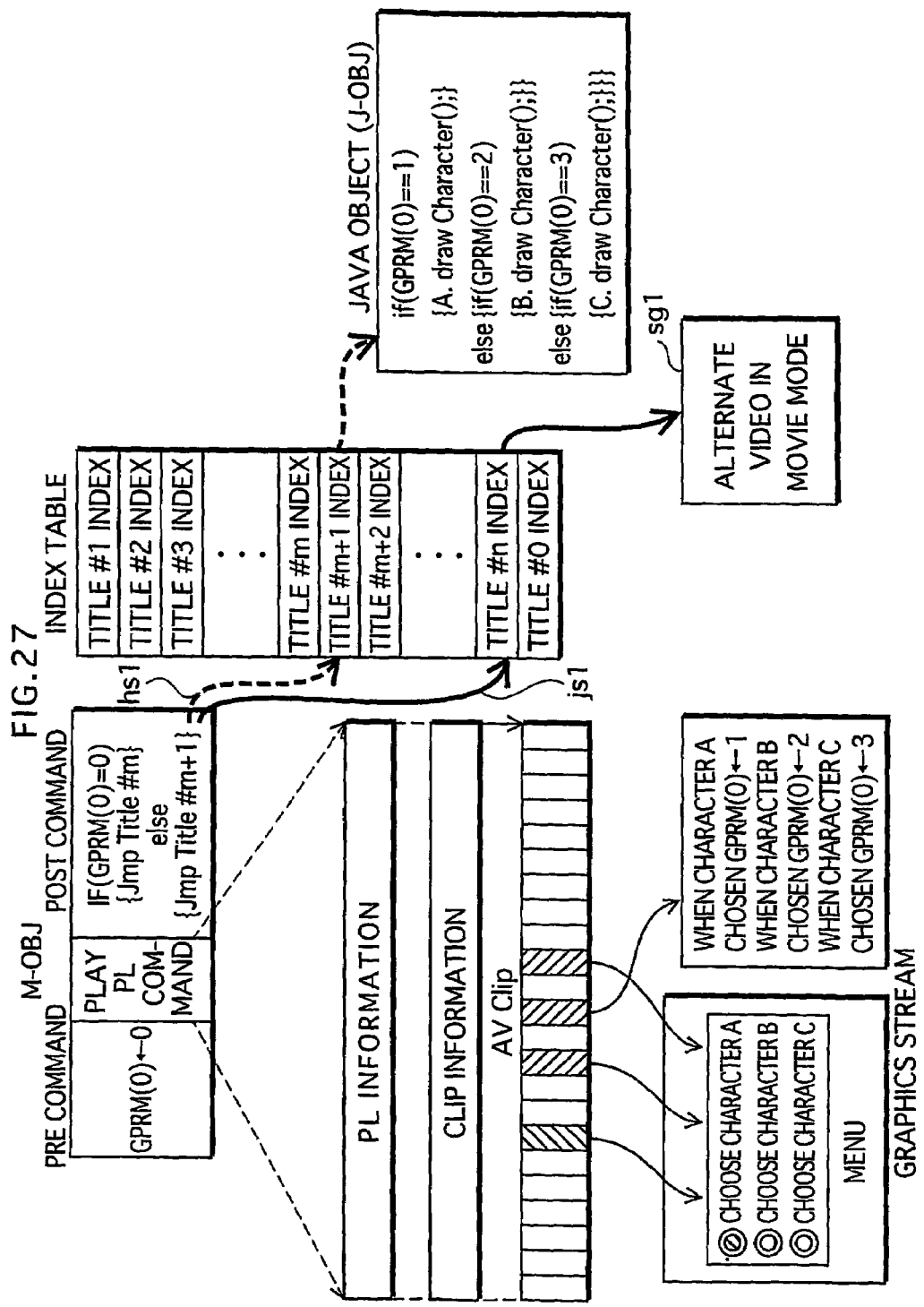
FIG. 27 shows how branching is performed when a BD-ROM having the scenario in FIG. 18 recorded thereon is mounted in a core-system playback device.

FIG. 27 shows what kind of branching is performed when a BD-ROM having the scenarios shown in FIG. 26 recorded thereon is loaded in a core system playback device. Depicting the arrows in FIG. 26 using the broken line hs1 in FIG. 27 shows that the branching in FIG. 26 is no longer valid because of the core system lacking an element for executing Java objects. The arrow js1 in FIG. 27 shows branching used in exception processing performed in place of the invalid branching. The branching used in exception processing is indirect referencing via the Index of Title#. The filename of MOVIE object sg1 is stored in the Index of Title#, MOVIE object sg1 being read by the playback device and executed in this branching. Because of displaying video in MOVIE objects when the BD-ROM is loaded in a playback device having only a core system, it is possible to avoid Stop and Restart.

Thus concludes the description relating to enhancement of the BD-ROM in embodiment 2. Enhancements on the playback device side will now be described.

A characteristic of module manager 20 in embodiment 2 is the branch control. Branch controls read dynamic scenarios identified as branch targets to memory, and have one of DVD-like module 16, Java module 17 and BROWSER module 18 execute the dynamic scenarios. Identification is necessary particularly when branch-target dynamic scenarios are specified using an indirect referencing format. Identification is carried out by referring to the branch-target labels of branch commands and retrieving filenames from Indexes corresponding to the labels. A judgment as to whether mode switching is necessary is performed in conjunction with this identification. The mode-switching judgment is performed by referring to the Index corresponding to the branch-target label so as to determine the file extension stored or the mode shown by stored attribute information. The stored content of the Index reveals whether mode switching is necessary. If mode switching is necessary, the branch-target dynamic scenario is read to memory, and a mode-transition request is outputted to the module that executes the post-switching mode. As a result of the mode-transition request being outputted, the module executing the post-switching mode executes the branch-target dynamic scenario in memory.

Figure 28:
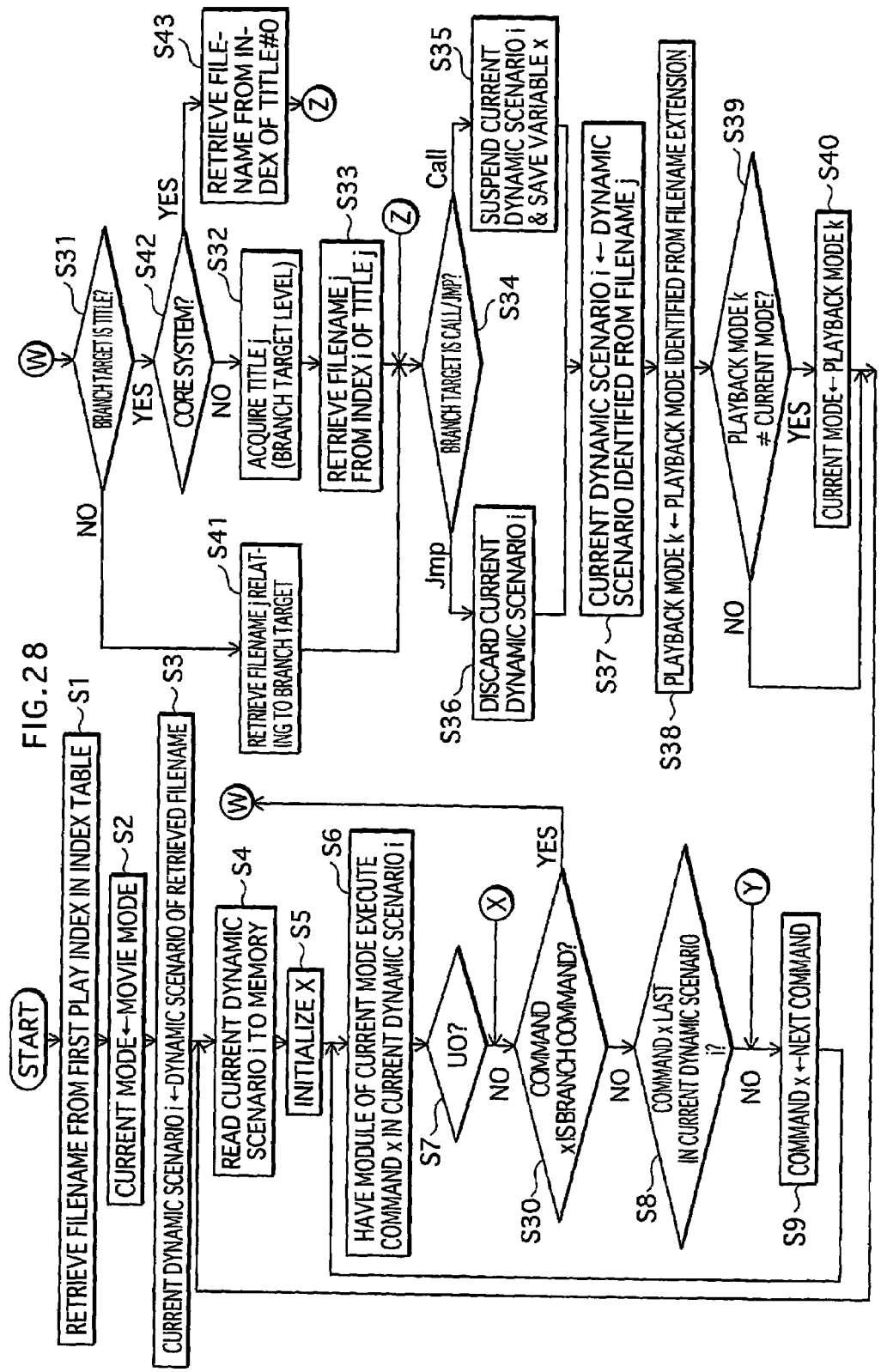
FIG. 28 shows processing procedures performed by module manager 20 in an embodiment 2.

The processing procedures by module manager 20 in embodiment 2 as a result of module manager 20 performing the above branch controls are as shown in FIG. 28. FIG. 28, being based on the flowchart shown in FIG. 20, depicts the differences between the two flowcharts.

Although commands in the current dynamic scenario i are executed one at a time by repeating the steps S6 to S9, step S30 has been newly added to the loop processing of steps S6 to S9 in the FIG. 28 flowchart.

Step S30 is a judgment as to whether or not command x is a branch command. If Step S30 is YES, module manager 20 returns to step S4 after setting the current dynamic scenario to the new dynamic scenario in steps S31 to s43. As a result, the new dynamic scenario is read to memory and executed.

The following description relates to the processing in steps S31 to S43. This processing involves branch controls, and differs depending on the judgment results of steps S31, S34, S39 and S42. Step S31 is a judgment as to whether the branch target of a branch command is described using a Title label. If YES, module manager 20 acquires the branch-target label Titlej after passing through the step S42 judgment (step S32), and retrieves filenamej from Indexi of Titlej in the Index Table (step S33). If NO, module manager 20 retrieves filenamej showing the branch target (step S41).

Step S34 is a judgment as to whether the branch command is a Call command or a Jmp command. If a Call command, module manager 20 saves variable x and SPRMs after suspending the current dynamic scenario i (step S35). If a Jmp command, module manager 20 discards the current dynamic scenario i (step S36).

Having passed through the above processing, module manager 20 sets the dynamic scenario identified from filenamej as the current dynamic scenario i (step S37), and sets the playback mode identified from the retrieved extension as playback mode k (step S38). After these settings, module manager 20 executes step S39. Step S39 is a judgment as to whether playback mode k is the current playback mode. If not the same, module manager 20 sets playback mode k as the current playback mode (step S40), and transfers to step S4. After that the processing of steps S4 to S9 is repeated with respect to the newly set current dynamic scenario. Step S42 is a judgment as to whether the playback device is a core system or a full system, and if a core system, module manager 20 retrieves the filename from Index of Title#0, and sets this as the branch target (step S43).

Since the playback device is set as a core system when difficulties are encountered with enhanced mode execution for some reason, and branching performed while referring to an Index in the Index Table for use in exception processing, it is possible according to the present embodiment as described above to avoid Stop, Restart, and the like.

Embodiment 3

Embodiment 3 relates to enhancements when playback devices and BD-ROMs of various specifications are introduced. When there is strong pressure to quickly commercialize BD-ROMs and playback devices, BD-ROM versions with few supportable functions, such as version 1.0 that only supports MOVIE mode and version 1.1 that supports MOVIE mode and enhanced modes, end up being commercialized and thrown on the market. In this case, the market end up getting populated with a number of versions of playback devices, such as version 1.0 and version 1.1 BD-ROMs, and version 1.0 and version 1.1 playback devices. This being the case, branching from a MOVIE object in MOVIE mode to a MOVIE object in an enhanced mode may occur with a version 1.1 BD-ROM loaded in a version 1.0 playback device, for example. In this case, it is not possible to execute the MOVIE object in an enhanced mode since the version 1.0 playback device only has a module for MOVIE mode. Thus with the present embodiment, Index Tables relating to all available versions are recorded on BD-ROMs. FIG. 29A is a version 1.1 BD-ROM. A version 1.1 Index Table and a version 1.0 Index Table are recorded on the BD-ROM in FIG. 29A. TITLE#1INDEX to TITLE#mINDEX exist in the version 1.0 Index Table. As shown in embodiment 2, these INDEXs are referred to when branching to MOVIE-mode dynamic scenarios.

TITLE#1INDEX to TITLE#mINDEX, TITLE#m+1IN-DEX to TITLE#nINDEX, and TITLE#0INDEX exist in the version 1. Index Table. As shown in embodiment 2, these INDEXs are referred to when branching to MOVIE-mode dynamic scenarios, enhanced mode dynamic scenarios, and dynamic scenarios used in exception processing.

When one of these versions of a BD-ROM is loaded in a playback device, the playback device selects MOVIE objects using the Index Table matching the version of the playback device from among the Index Tables relating to the plurality of versions recorded on the BD-ROM.

FIG. 29B assumes a state in which the BD-ROM shown in FIG. 29A is loaded in a version 1.0 playback device. Since the playback device in FIG. 29B is version 1.0, when branching occurs, branch-target MOVIE objects are identified by referring to the version 1.0 Index Table out of the version 1.0 and 1.1 Index Tables.

FIG. 29C assumes a state in which the BD-ROM shown in FIG. 29A is loaded in a version 1.1 playback device. Since the playback device in FIG. 29C is version 1.1, when branching occurs, branch-target MOVIE objects are identified by referring to the version 1.1 Index Table out of the version 1.0 and 1.1 Index Tables.

In order to perform the above processing, module manager 20 in a playback device according to embodiment 3 performs processing based on the flowchart in FIG. 30. When a BD-ROM is loaded in the playback device, module manager 20 acquires the version number in the device (step S45), reads whichever of the plurality of Index Tables recorded on the BD-ROM matches the acquired version number, and holds the read Index Table (step S46). Module manager 20 then performs the processing of steps S1 to S42 while referring to the held Index Table. Description of the processing of steps S1 to S42, being the same as that shown in embodiment 2, is omitted here.

According the present embodiment as described above, it is possible to guarantee compatibility with past versions of playback devices even when various versions of playback devices and BD-ROMs appear on the market, by choosing an Index Table that matches the version of the playback device and performing playback with reference to this Index Table.

Embodiment 4

Figure 31:
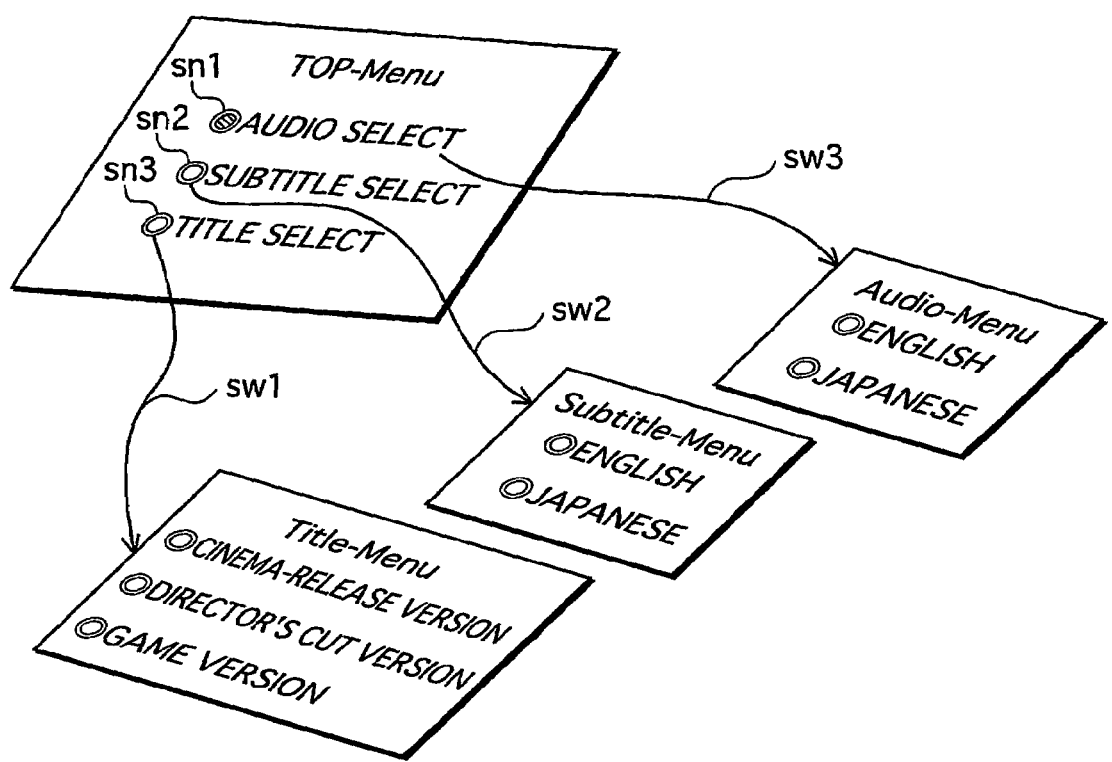
FIG. 31 shows a menu hierarchy realized by a BD-ROM.

The present embodiment relates to enhancements when realizing similar menu controls to DVD on a BD-ROM. FIG. 31 shows a menu hierarchy realized by a BD-ROM. The menu hierarchy in FIG. 31 is structured to place a TopMenu at the highest level, and to be able to select a subordinate TitleMenu, SubtitleMenu, and AudioMenu from the TopMenu. The arrows sw1, sw2 and sw3 in FIG. 31 schematically show menu switching by button selection. The TopMenu disposes buttons for receiving which of an audio selection, a subtitle selection, and a Title selection to perform (buttons sn1, sn2, sn3 in FIG. 31).

The TitleMenu disposes buttons for receiving movie work selections, such as selection of a cinema version of a movie work (Title), a director's cut version, or a game version. The AudioMenu disposes buttons for receiving whether audio playback is to be in Japanese or English, and the Subtitle-Menu disposes buttons for receiving whether subtitle display is to be in Japanese or English.

Figure 32:
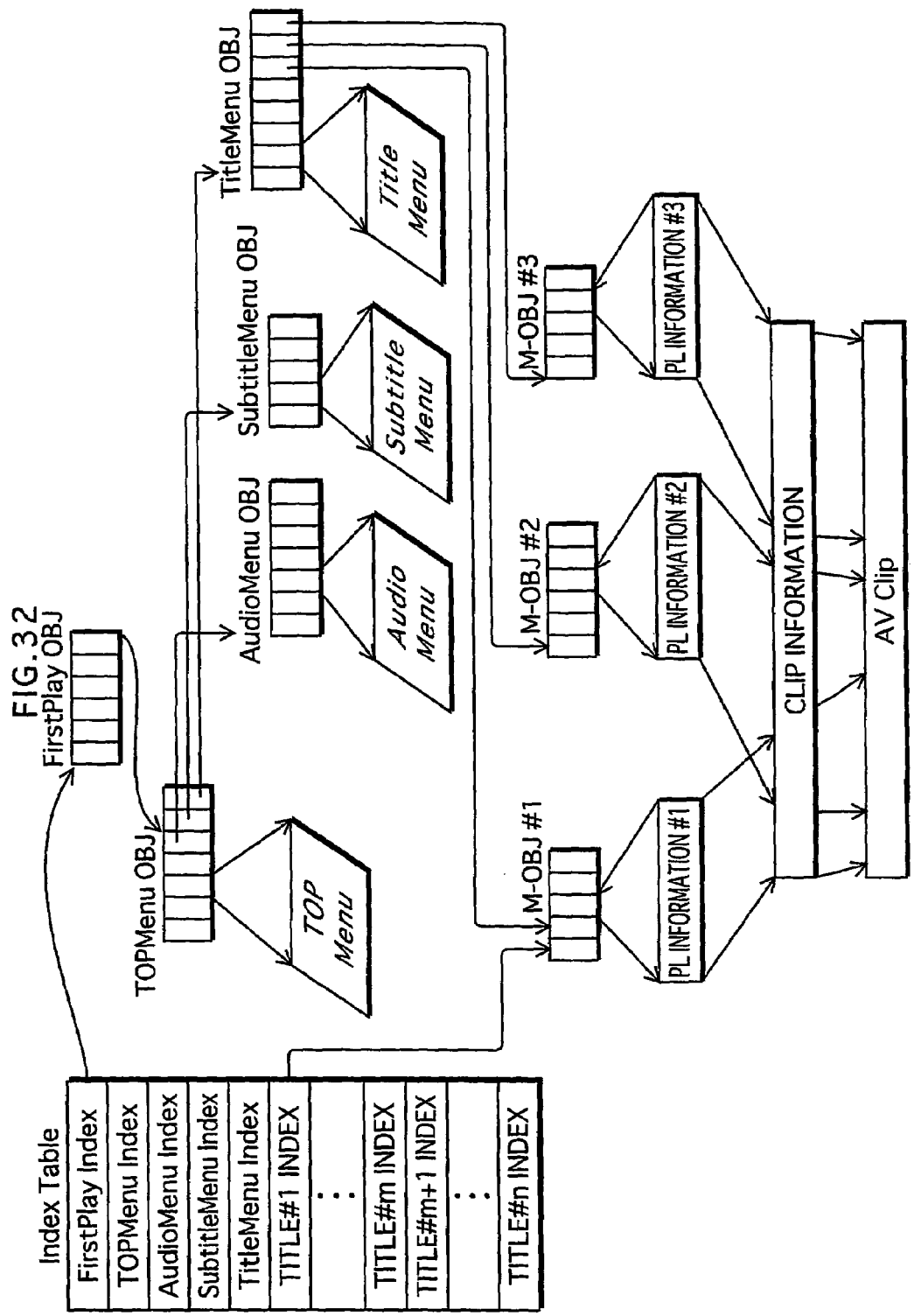
FIG. 32 shows MOVIE objects for operating menus having a hierarchy.

MOVIE objects for operating menus having such a hierarchy are shown in FIG. 32.

A FirstPlay object (FirstPlay OBJ) is a dynamic scenario describing a startup procedure when loading a BD-ROM in a playback device. The square boxes representing the FirstPlay object show commands for executing this setup procedure. The last command of the FirstPlay object is a branch command, the branch target being a TopMenu object.

The TopMenu object (TOPMenu OBJ) is a dynamic scenario for controlling the behavior of the TopMenu. The TopMenu object is the object called when a user requests a menu call, and equates to the status-setting routine mentioned in embodiment 1. The square boxes representing the TopMenu object schematize individual commands that express this control procedure. Included in these commands are a command for changing a state of buttons in the TopMenu in response to operations from the user, and a branch command for branching in response to the activation of buttons. The branch command realizes menu switching from the TopMenu to the Title-Menu, from the TopMenu to the SubtitleMenu, and from the TopMenu to the AudioMenu.

An AudioMenu object (AudioMenu OBJ) is a dynamic scenario for controlling the behavior of the AudioMenu. The square boxes structuring the AudioMenu object schematize individual commands that express this control procedure. Included in these commands is a command for changing a state of buttons in the AudioMenu in response to operations from the user, and a command for updating SPRMs used in audio setting in response to the activation of buttons.

A SubtitleMenu object (SubtitleMenu OBJ) is a dynamic scenario for controlling the behavior of the SubtitleMenu. The square boxes structuring the SubtitleMenu object schematize individual commands that express this control procedure. Included in these commands is a command for changing a state of buttons in the SubtitleMenu in response to operations from the user, and a command for updating SPRMs used in audio setting in response to the activation of buttons.

A TitleMenu object (TitleMenu OBJ) is a dynamic scenario for controlling the behavior of the TitleMenu. The TitleMenu object is the object called when a user requests a Title search, and equates to the dynamic scenario used for Title searching mentioned in embodiment 1. The square boxes structuring the TitleMenu object schematize individual commands that express this control procedure. Included in these commands are a command for changing a state of buttons in the TitleMenu in response to operations from the user, and a branch command for branching in response to the activation of buttons. The branch command realizes branching to individual Titles.

Menu behavior such as that realized in DVD can be realized by these MOVIE objects for use with menus. Thus concludes the description of MOVIE objects relating to menu controls.

Enhancement of the Index Table in the present embodiment will now be described. A FirstPlay Index, a TOPMenu Index, an AudioMenu Index, a SubtitleMenu Index, and a TitleMenu Index are added to the Index Table in the present embodiment. As described in embodiment 1, these indexes are also referred to by dynamic scenarios relating to each of the three modes.

The FirstPlay Index is referred to during BD-ROM startup. The filename of the FirstPlay object is described in this index.

The TopMenu Index, AudioMenu Index, SubtitleMenu Index, and TitleMenu Index are referred to when user operations are conducted to directly call the AudioMenu, Subtitle-Menu, and TitleMenu. A direct call by a user is conducted by the user depressing an Audio select key, a Subtitle select key, or a Title select key on a remote controller.

Thus concludes the description of enhancements to MOVIE objects in the present embodiment. Enhancement of a playback device in the present embodiment will now be described. To operate MOVIE objects such as these, module manager 20 needs to perform the processing procedures shown in the FIG. 33 flowchart.

Figure 33:
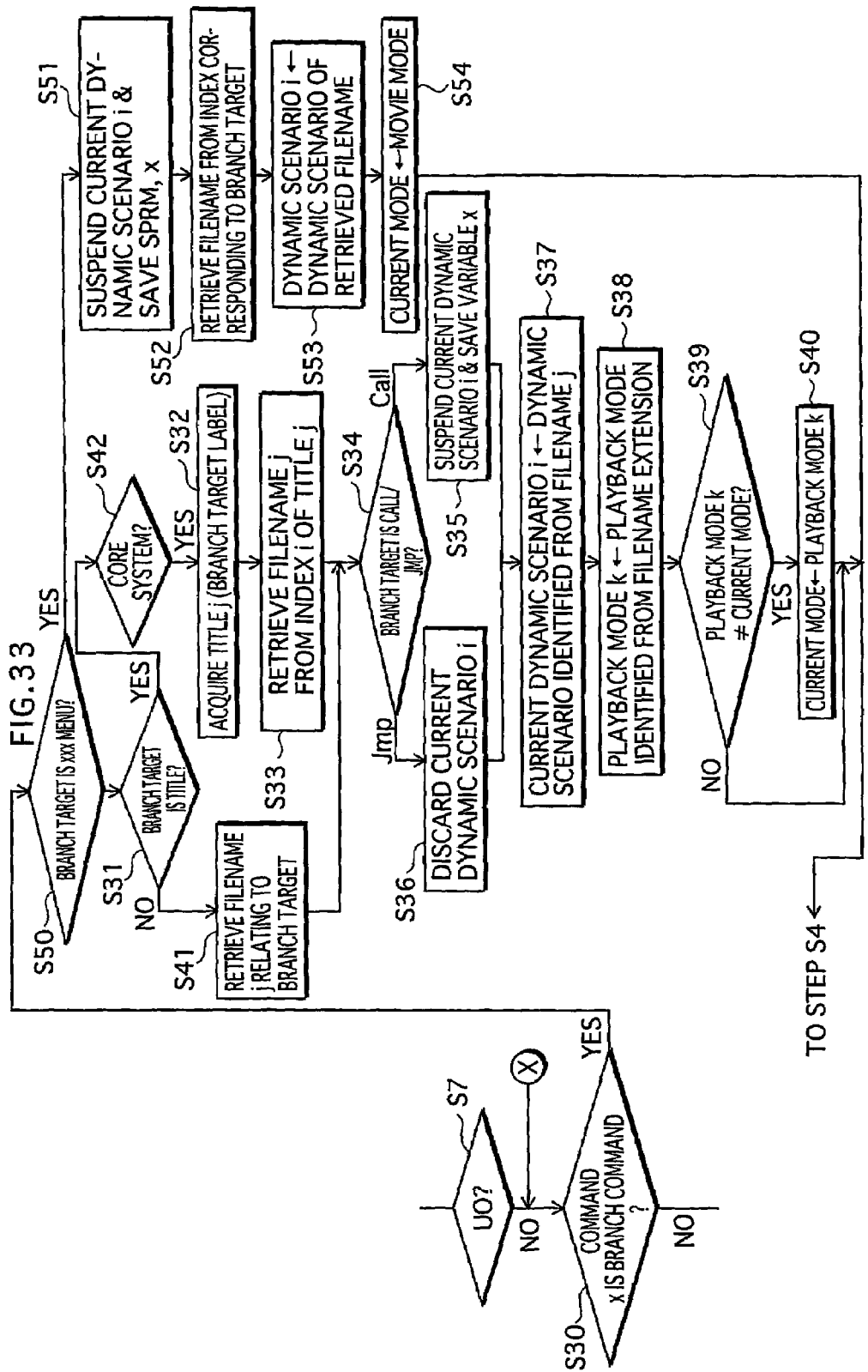
FIG. 33 is a flowchart showing branch-control processing procedures.

In the present embodiment, module manager 20, which originally performs menu controls, performs branch controls using the processing procedures shown in FIG. 33. This flowchart differs in that step S50 has been inserted between steps S30 and S31. If YES in step S50, module manager 20 performs the steps S51 to S54 processing and returns to step S4. Steps S51 to S54 involve the setting of a scenario for conducting menu controls as the current dynamic scenario. That is, if the branch target of the branch command is xxxMenu (step S50YES), module manager 20 suspends the current dynamic scenario i, saves SPRMs and variable x (step S52), retrieves a filename from the Index corresponding to the branch-target menu (step S52), sets the dynamic scenario of the retrieved filename as the current dynamic scenario i (step S53), and returns the current mode to MOVIE mode (step S54). After that module manager 20 proceeds to execute the current dynamic scenario.

Since branching to dynamic scenarios for menu controls is realized in indirect referencing via the Indexes of the Index Table, it is possible according to the present embodiment as described above to branch to dynamic scenarios for use in menu controls, even when a menu key is depressed during execution of Java mode or Browser mode. Audio and Subtitle switching from a Java virtual machine and Browser mode is made possible, thus realizing Audio and Subtitle switching similar to normal DVD even when playback is performed using a Java virtual machine or Browser mode.

Embodiment 5

Embodiment 5 relates to an enhancement for preventing any detrimental effects that may be exerted on other modes by data provided for MOVIE mode. Controls in MOVIE mode can be performed not only by MOVIE objects but also by commands (button commands) in interactive graphics streams multiplexed onto AVClips.

Button commands are executed when buttons described by graphics streams are activated. Having button commands incorporated in AVClips is convenient in the description of playback controls for having a playback device execute specific processing according to timings at which individual frames of particular moving images appear on a screen; that is, playback controls synchronized closely with the moving image content. Also, since button commands are multiplexed on the actual AVClip, it is not necessary to store all of the button commands corresponding to the AVClip in memory, even when there are several hundred sections wanting to perform playback controls. Since button commands are read from a BD-ROM for every ACCESS UNIT together with video packets, it is preferable to have button commands corresponding to a moving-image section for current playback reside in memory, and then to delete these button commands from memory when playback of this moving-image section and store button commands corresponding to the next moving-image section in memory. Since button commands are multiplexed onto AVClips, it is possible to reduce the installed memory to a minimum required amount, even when, for instance, there are several hundred button commands.

When button commands are embedded in a stream, the problem arises of interference from dynamic scenarios in Java mode. For example, if button commands embedded in a stream are supplied to modules when executing playback controls in Java mode, Java mode dynamic scenarios and button commands end up being executed at the same time, inviting player errors. With the present embodiment, which resolves this problem, PlayItems are provided with a filter specification function.

Filter specification refers to distinguishing between playable and unplayable elementary streams multiplexed on an AVClip.

Figure 34:
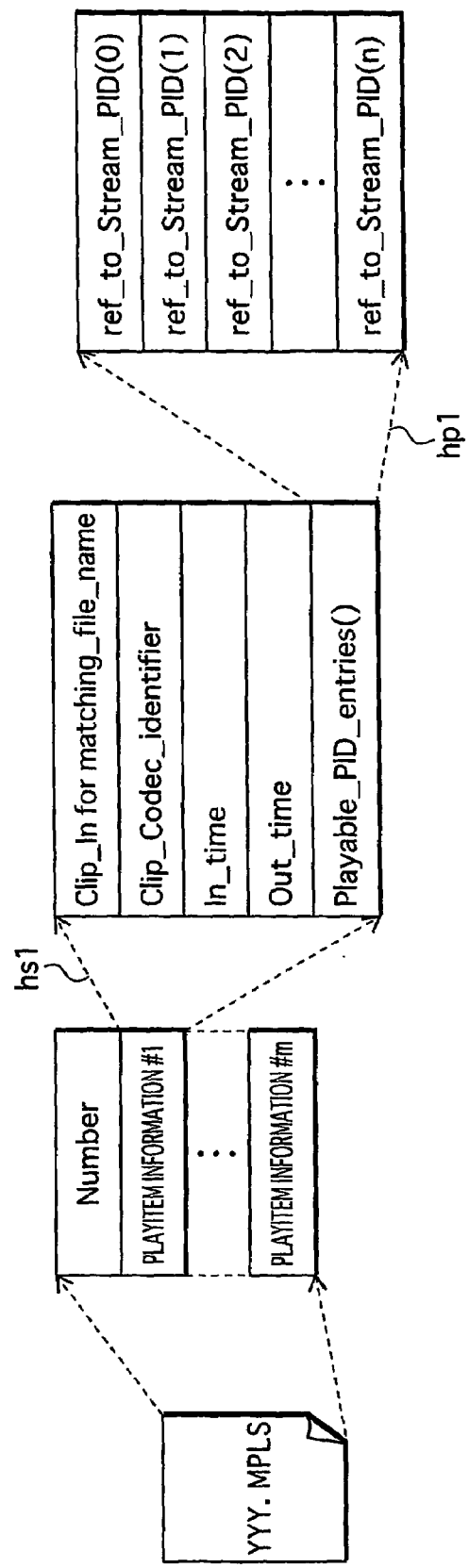
FIG. 34 shows an internal structure of a PlayItem pertaining to an embodiment 5.

FIG. 34 shows an internal structure of a PlayItem pertaining to embodiment 5. "Playable_PID_entries" has been added in FIG. 34. The leader hp1 in FIG. 34 highlights the structure of Playable_PID_entries. As revealed below, Playable_PID_entries enumerates PID elementary streams for playback.

Figure 35:
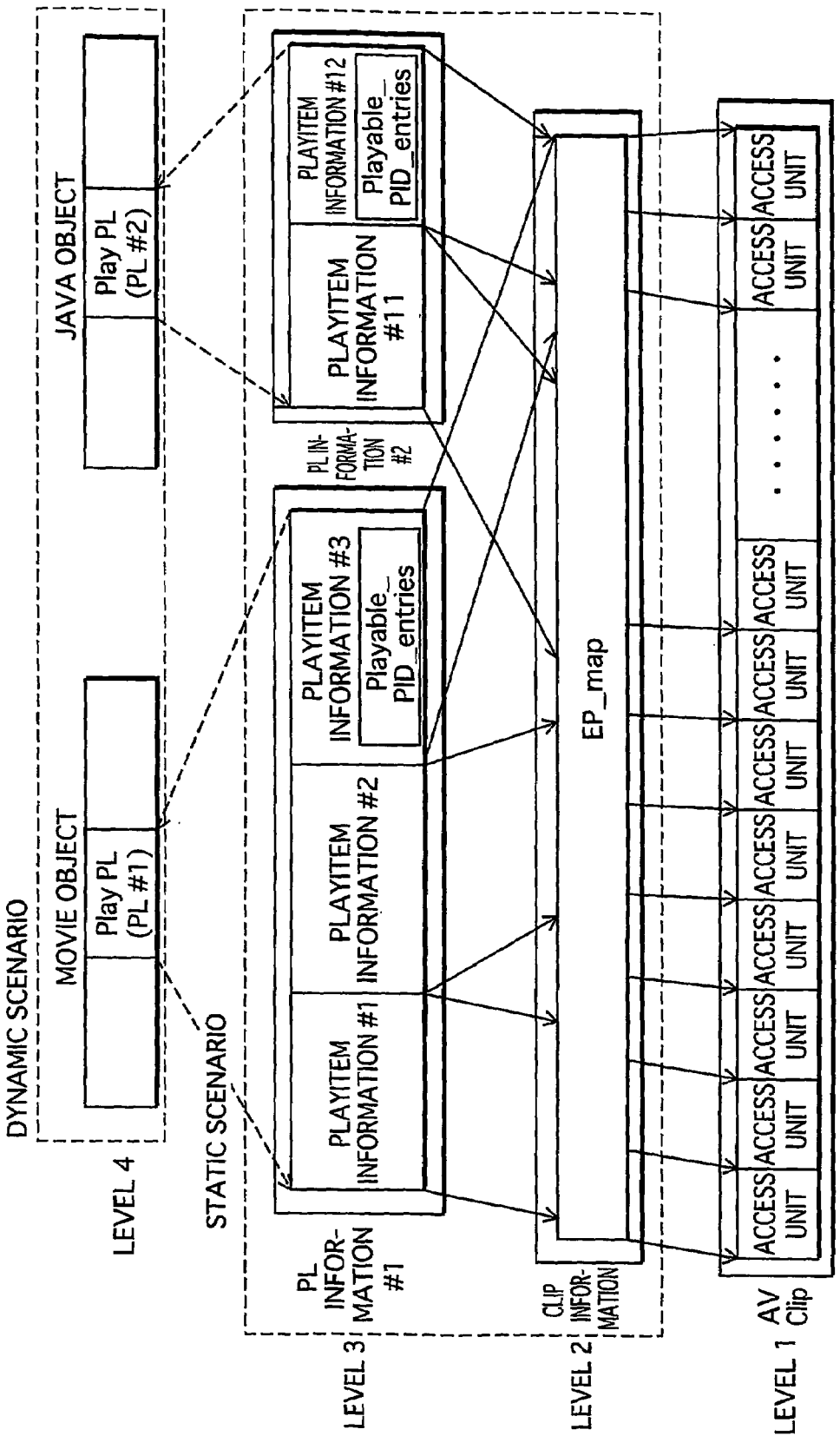
FIG. 35 shows a hierarchical structure of a PlayList with respect to which playback controls are performed by MOVIE and Java objects.

The following description relates to which playback controls are realized by filter specifications in PlayItems. FIG. 35 shows the hierarchical structure of PLs in which playback controls are performed by Java objects. The MOVIE object at level 4 in FIG. 35 includes a command (PlayPL (PL#1)) for having PL#1 played. PlayItem#3 of the three PlayItems #1, #2 and #3 structuring PL#1 includes Playable_PID_entries, meaning that filter specification is possible.

The Java object at level 4 in FIG. 35 includes a command (PlayPL(PL#2)) for having PL#2 played. PlayItem#12 of the two PlayItems structuring PL#2 includes Playable_PID_entries, meaning that filter specification is possible.

Figure 36:
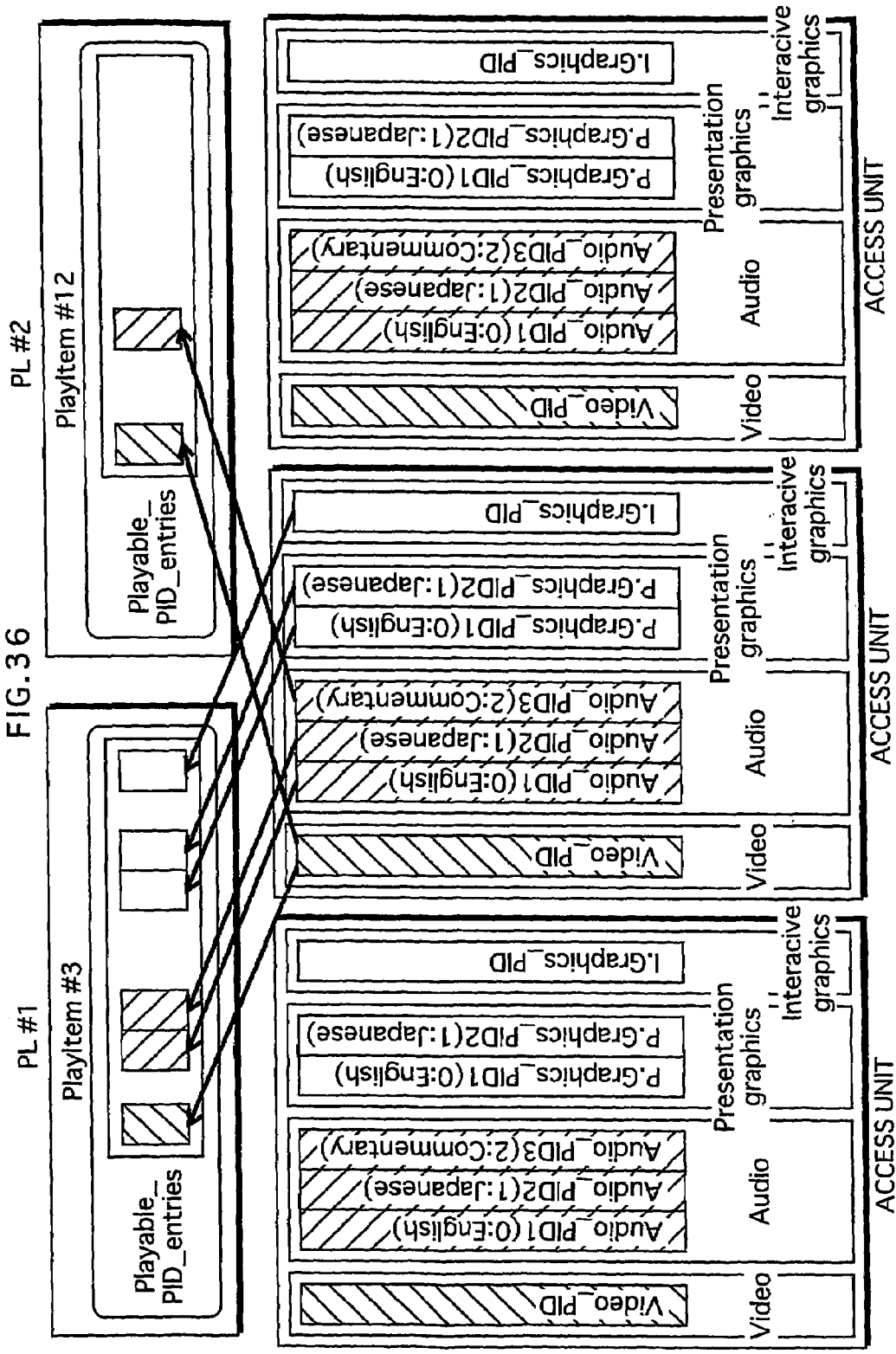
FIG. 36 shows how filter specifications are performed as a result of Playable_PID_entries in PlayItems #3 and #12.

FIG. 36 shows what filter specifications are performed by Playable_PID_entries in PlayItems #3 and #12. In FIG. 36, ACCESS UNITs structuring an AVClip are shown at the bottom, and two PlayItems #3 and #12 are shown at the top. One video stream, three audio streams, two presentation graphics streams, and one interactive graphics stream are multiplexed in the ACCESS UNITs. A "Video_PID" PID is appended to the video stream, "Audio_PID" PIDs are appended to the audio streams, "P.Graphics_PID" PIDs are appended to the presentation graphics streams, and "I.Graphics_PID" PIDs are appended to the interactive graphics streams. Of the three audio streams, the one having "Audio_PID1" appended is English audio (0:English), the one having "Audio_PID2" appended is Japanese audio (1:Japanese), and the one having "Audio_PID3" appended is Commentary audio (2:Commentary). Of the two presentation graphics streams, the one having "P.Graphics_PID1" appended is English audio (0:English), and the one having "P.Graphics_PID2" appended is Japanese audio (1:Japanese).

PlayItems #3 and #12 at the top of FIG. 36 have different filter specifications. The enumeration of squares in PlayItems #3 and #12 are the actual content of Playable_PID_entries, PlayItem#3 being set to allow playback of the Video_PID video stream, the Audio_PID1 and Audio_PID2 audio streams, the P.Graphics_PID1 and P.Graphics_PID2 presentation graphics streams, and the I.Graphics_PID interactive graphics stream. PlayItem#12 is set to allow playback of the Video_PID video stream, and the Audio_PID3 audio stream. When playing PlayItem#3, Playable_PID_entries in PlayItem#3 are set to PID filter 4 in the playback device. As a result, PID filter 4 outputs the Video_PID video stream to video decoder 5, outputs the Audio_PID1 and Audio_PID2 audio streams to audio decoder 7, and outputs the P.Graphics_PID1 and P.Graphics_PID2 presentation graphics streams as well as the I.Graphics_PID interactive graphics stream to graphics decoder 9. Since PlayItem#3 is set so that all of the graphics streams are playable, playback of all of the graphics streams multiplexed on the AVClip is possible.

On the other hand, since PlayItem#12 is set so that not all of the graphics streams are playable, controls using Java language are possible without there being interference from dynamic scenarios in Java mode.

Figure 37:
FIG. 37 shows how playback output is made possible by Playable_PID_entries in PlayItems #3 and #12.

FIG. 37 shows possible playback outputs resulting from Playable_PID_entries in PlayItems #3 and #12. Since playback of the Video_PID video stream, the Audio_PID1 and Audio_PID2 audio streams, the P.Graphics_PID1 and P.Graphics_PID2 presentation graphics streams, and the I.Graphics_PID interactive graphics stream is possible with PlayItem#3, it is possible with playback using MOVIE objects to perform playback output of the video stream following the playback output of the Audio_PID1 audio stream (i.e. the narration "She's a captive of her own lies" in FIG. 37), the P.Graphics_PID1 presentation graphics stream (the Japanese subtitle "彼女は自分のうそに酔いしれた"), and the I.Graphics_PID interactive graphics stream (CONTINUE?●YES ◎NO).

PlayItem#12 is set so that not all of the graphics streams are playable, making it possible to only perform playback output of two stream; namely, the Video_PID video stream and the Audio_PID3 audio stream. If the Java object instructing the playback of this PlayItem draws a virtual studio (i.e. the room containing a camera, chair and light in FIG. 37), the Java object for performing the drawing will receive no interference from commands included in the graphics streams. It is thus possible to realize Java-mode specific processing, while avoiding interference from commands included in graphics streams. The Audio_PID3 audio stream set to playable by PlayItem#12 is a commentary by the movie director (i.e. the lines "I take my hat off to her outstanding acting ability"), and by having such commentary by the director played in the virtual studio, it is possible to create the atmosphere of a movie set.

As a result of this Java object, it is possible to listen to the movie director's comments while playing movie scenes as background images in a room modeled on a movie studio.

By recording this Title on a BD-ROM as a bonus track Title, the product value of the BD-ROM can be increased. Using the filter specification in a PlayItem to record the bonus track Title on the BD-ROM brings about the following merits.

The commentary of world-renown movie directors is of definite interest to movie buffs, and exists on currently available DVDs as something that increases the added value of the movie work.

While being able to listen to the director's commentary is the greatest attraction of this Title, playing movies scenes as background images also helps to increases Title's attractiveness. In other words, being able to listen to behind-the-scenes talk relating to the movie production while viewing highlight scenes from the movie increases the aura of the commentary. The problem in this case becomes one of how to handle audio streams relating to the commentary. The orthodox approach would be to provide movie scenes that one wants to use as background images separately from the main feature, and to multiplex these with audio streams so as to create the bonus track. However, this approach means that movie scenes for use as background images need to be recorded on the BD-ROM separately from the main feature, increasing the number of recording items and creating capacity-related problems.

Another possible method involves multiplexing audio streams for the commentary on video streams for the main feature together with audio streams used in the main feature. This allows scenes from the main feature to be uses as background images to the commentary, although the danger here is that the commentary data will also be heard when playing the main feature. As such, the filter specification in the PlayItem structuring the main feature Title is set so that only the audio stream of the commentary is OFF and any remaining audio streams are ON. On the other hand, the filter specification in the PlayItem structuring the bonus Title is set so that only the audio stream of the commentary is ON and any remaining audio streams are OFF. By doing this, it is preferable to multiplex all audio streams relating to the main feature and commentary together on a single AVClip for recording on a BD-ROM.

Since it is not necessary to create separate AvClips for the commentary and main feature (i.e. an AvClip only for audio streams of the main feature, and an AvClip only for audio streams of the commentary), it is possible to reduce the number of AVClips for recording on a BD-ROM, and make authoring easier.

Thus concludes the description of enhancements to a BD-ROM in embodiment 5. An enhancement to a playback device in embodiment 5 will now be described.

Figure 38:
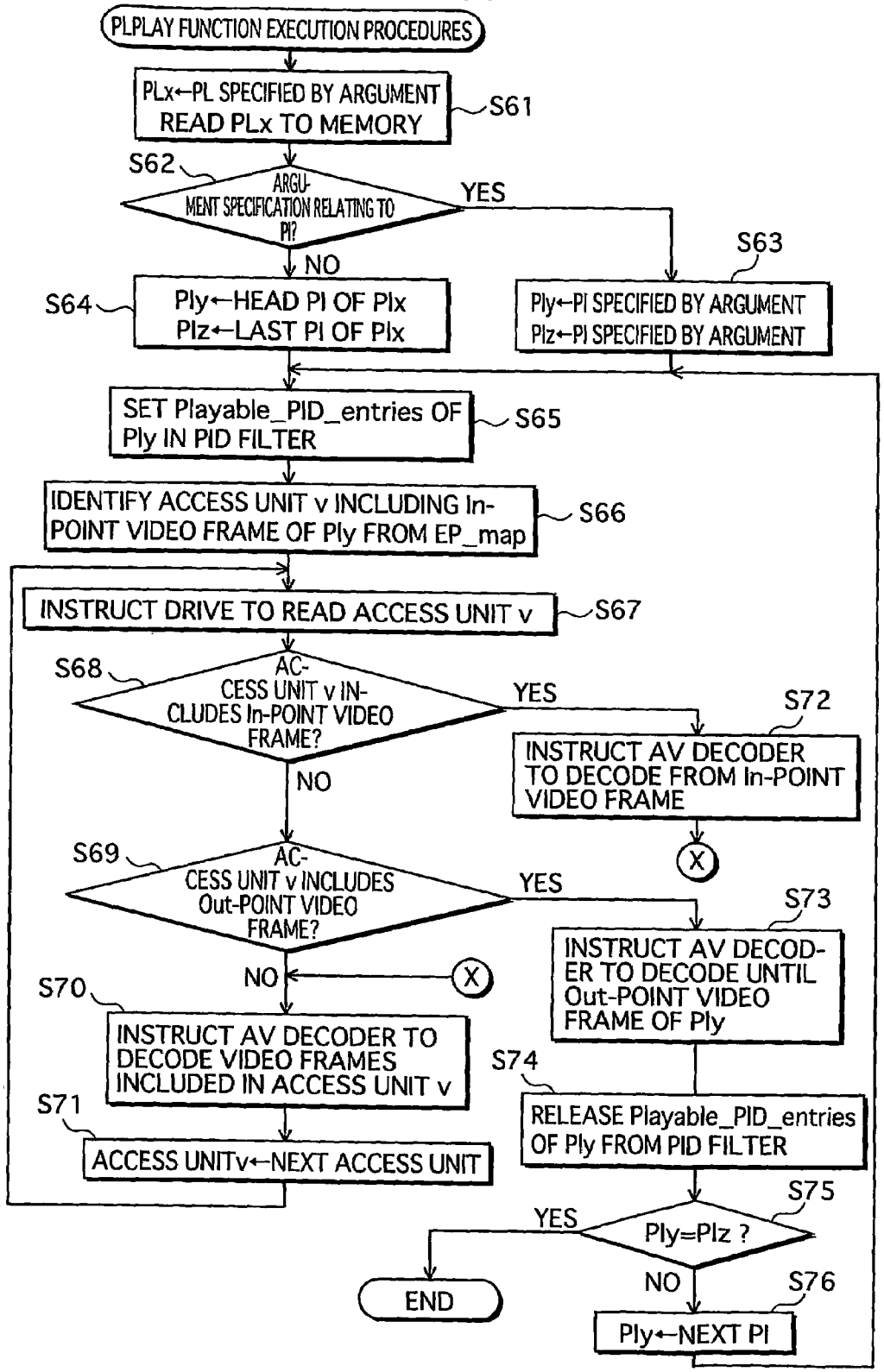
FIG. 38 is a flowchart showing PLPlay function execution procedures performed by a playback control engine 12.

The processing performed by a playback device in embodiment 5 is realized by playback control engine 12 executing the processing procedures in FIG. 38.

FIG. 38 is a flowchart showing the execution procedures of a PLPlay function performed by playback control engine 12. In this flowchart, PLx is the PL targeted for processing, PIy is the PI targeted for processing, and ACCESS UNITv is the ACCESS UNIT targeted for processing. This flowchart comprises the following procedures: setting the PL specified by an argument of the PLPlay function as PLx, reading PLx to memory (step S61), identifying the PI targeted for processing (steps S62 to S64), and reading the ACCESS UNIT structuring this PI (steps S65 to S76).

Step S62 is a judgment as to whether there is a PI argument specification. If there is an argument specification, playback control engine 12 sets PIy to the argument specified PI, and sets PIz to the same argument specified PI (step S63). PIz is the PI defining the end of the reading range. Both PIy and PIz are set to the argument specified PI because of it only being necessary to read this PI in the case of a PI being specified by an argument.

If there is no argument specification, playback control engine 12 sets PIy to the head PI in PLx, and sets PIz to the last PI in PLx (step S64).

Steps S65 to S76 show the reading of an ACCESS UNIT structuring PIy, and a decoding procedure. This procedure involves setting Playable_PID_entries in PIy to PID filter 4 (step S65), setting ACCESS UNITv that includes the In-point video frame in PIy from the EP_map (step S66), instructing BD-ROM drive 1 to read ACCESS UNITv (step S67), and then, after passing through the judgments of steps S68 to S69, instructing video decoder 5 to decode video frames included in ACCESS UNITv (step S70), and setting ACCESS UNITv to the next ACCESS UNIT (step S71). After that the processing of steps S67 to S71 is repeated for all of the ACCESS UNITs belonging to PIy.

Step S68 is a judgment as to whether ACCESS UNITv includes the In-point video frame. If the In-point video frame is included (step S68=YES), playback control engine 12 instructs video decoder 5 to decode from the In-point video frame to the last video frame in ACCESS UNITv (step S72), and moves to step S70.

Step S69 is a judgment as to whether ACCESS UNITv includes the Out-point video frame. If the Out-point video frame is included (step S69=YES), playback control engine 12 instructs video decoder 5 to decode from the head video frame to the Out-point video frame in ACCESS UNITv (step S73) and releases Playable_PID_entries in PIy from PID filter 4 (step S74). As a result, the filter specification by PIy is set to OFF. The step S75 judgment is then performed. Step S75, which is the final judgment in the flowchart, judges whether PIy is now PIz. Playback control engine 12 ends the flowchart if step S75 is YES, and sets PIy to the next PI if NO (step S76), before returning to step S65. After that the processing of steps S65 to S77 is repeated until judged YES at step S75. Thus concludes the description of the processing procedures performed by playback control engine 12.

Since PlayItems are provided with a filter specification that sets which of the plurality of elementary streams multiplexed in an AVClip are playable and which are unplayable, it is possible according to the present embodiment to avoid any effects exerted by button commands in elementary streams multiplexed on AVClips as a result of dynamic scenarios in each mode choosing compatible PlayItems. As such, Java module 17 no longer receives any interference from button commands, which contributes to the stable operation of the playback device.

Embodiment 6

Figure 39:
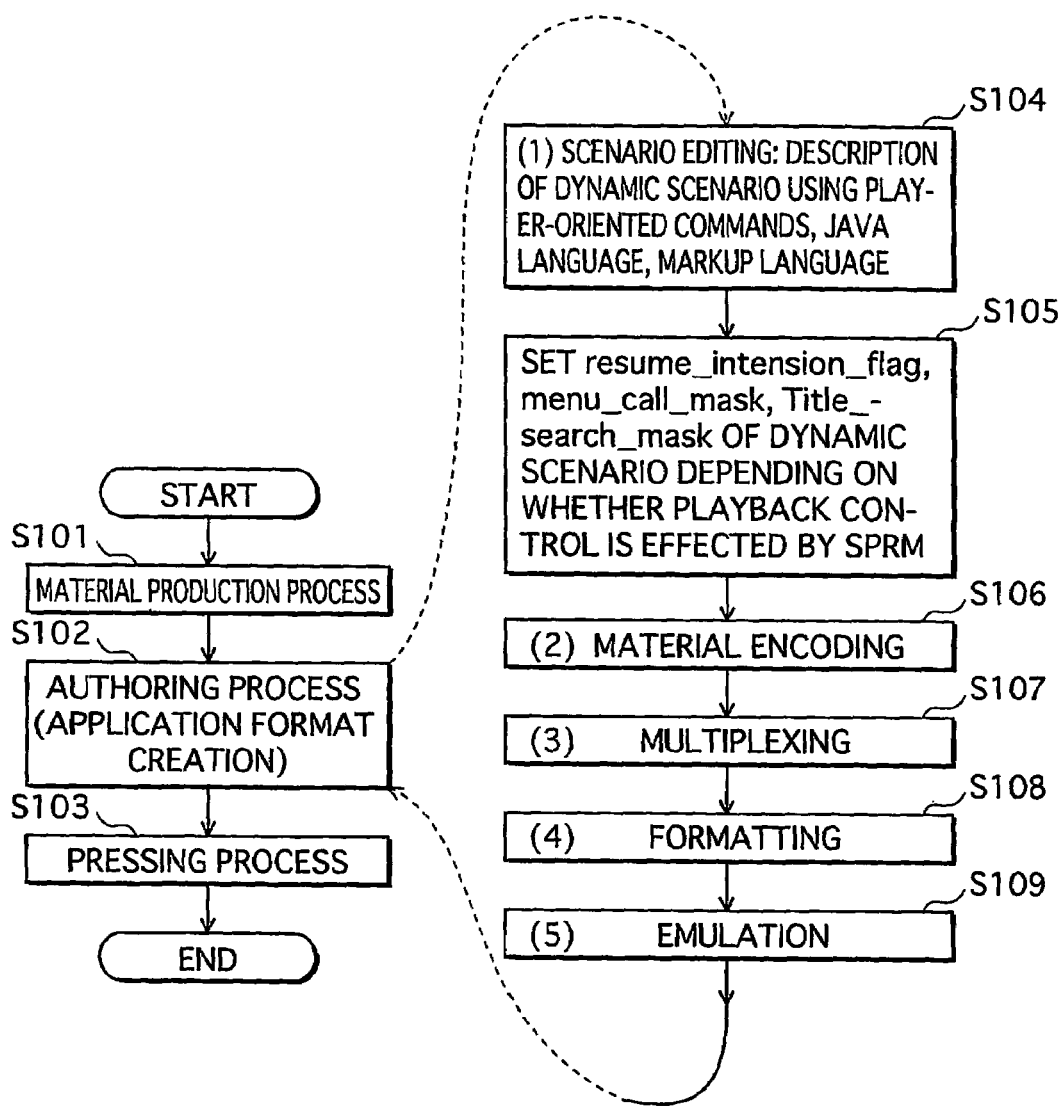
FIG. 39 is a flowchart showing production processes for a BD-ROM.

The present embodiment relates to BD-ROM production processes. FIG. 39 is a flowchart showing BD-ROM production processes pertaining to embodiment 6.

The BD-ROM production processes includes a material production process S101 for creating materials such as moving image records and audio records, an authoring process S102 for generating an application format, and a pressing process S103 for creating the BD-ROM master and pressing/laminating to complete the BD-ROM.

Of these processes, the authoring process targeting the BD-ROM comprises the processes of steps S104 to S109.

Scenario editing process S104 is for converting an outline created in the planning stage into a format comprehensible to a playback device. The scenario editing result is created as BD-ROM scenarios. Also, multiplexing parameters are also created in the scenario editing so as to realize multiplexing.

Once dynamic scenarios have been competed in the processes, the resume_intension_flag, menu_call_mask, Title_search_mask of each dynamic scenario is set in step S105. These settings are performed according to the effects of SPRMs exerted on playback controls by the dynamic scenarios. Detrimental effects resulting from menu calls and title searches during playback are prevented as a result of these settings.

Material encoding process S106 is a task for respectively encoding video, audio and sub-video material to obtain video, and audio and graphics streams.

In multiplexing process S107, video, audio, and graphics streams obtained as a result of the material encoding are interleave-multiplexed, and the result is converted to a single digital stream.

In formatting process S108, various types of information are created based on BD-ROM-oriented scenarios, and the scenarios and digital streams are adapted to a BD-ROM format.

Emulation process S109 is for confirming whether the authoring result is correct.

Because of being able to describe Java objects and Webpage objects using Java and markup languages, it is possible in the authoring processes described above to develop Java objects and Webpage objects using the same sensibility as that applied in the development of normal computer-oriented software. Therefore, the present embodiment has the effect of increasing the efficiency of scenario creation.

Remarks

The above description by no means shows the implementation of all configurations of the present invention. Implementation of the present invention is still possible according to implementation of configurations that carry out the following modifications (A), (B), (C), (D), . . . . The inventions pertaining to the claims of the present application range from expanded disclosure to generalized disclosure of the plurality of embodiments disclosed above and the modified configurations thereof. The degree of expansion or generalization is based on the particular characteristics of technical standards in the technical field of the present invention at the time of application.

However, since the inventions pertaining to the claims reflect the means for resolving technical issues relating to the prior art, the technical range of the inventions pertaining to the claims does not extend beyond the technical range recognized by those knowledgeable in the art with respect to resolving technical issues relating to the prior art. As such, the inventions pertaining to the claims of the present application possess a material correspondence with the disclosures in the detailed description.

(A) In all of the embodiments, an optical disk pertaining to the present invention is implemented as a BD-ROM. However, the optical disk of the present invention is characterized by the recorded dynamic scenarios and Index Table, and these characteristics are not dependent on the physical properties of a BD-ROM. Any form of recording media is applicable as long as there exists the capacity to record dynamic scenarios and Index Tables. For example, optical disks such as DVD-ROM, DVD-RAM, DVD-RW, DVD-R, DVD+RW, DVD+R, CD-R, CD-RW, and the like, and optical-magnetic disks such as PD, MO and the like are applicable. Semiconductor cards such a compact flash cards, PCM-CIA cards and the like are also applicable, as are (i) magnetic recording disks such as flexible disks, SuperDisk, Zip, Clik! and the like, and (ii) removable hard disk drives such as ORB, Jaz, SparQ, SyJet, EZFley, microdrive and the like. Furthermore, the recording medium may also be a built-in hard disk.

Dynamic scenarios, Index Tables, and PlayList information may be recorded on a different recording medium to AVClips and stream management information. These may then be read in parallel and played as a single video edit.

(B) Although the playback devices in all of the embodiments output AVClips recorded on a BD-ROM to a TV after decoding, the playback device may be structured from only a BD-ROM drive, and the TV may be equipped with all of the other elements. In this case, the playback device and the TV can be incorporated into a home network connected using IEEE1394. Also, although the playback devices in the embodiments are of a type used after connecting to a television, integral display-playback devices are also applicable. Furthermore, the playback device may be only those parts of the playback devices of the embodiments that perform essential parts of the processing. Because these playback devices are all inventions disclosed in the specification of the present application, acts involving the manufacture of playback devices based on an internal structure of the playback devices shown in embodiments 1 to 6 are implementations of the inventions disclosed in the specification of the present application. Acts that involve transferring (retail when cost is involved; a gift when no cost is involved), lending, or importing of playback devices shown in embodiments 1 to 6 are also implementations of the present invention. Acts that involve approaching the general user about transfer, rental or the like by means of show-widow displays, catalogue solicitation, pamphlet distribution and the like are also implementations of these playback devices.

(C) Because of the information processing by computer programs shown in the flowcharts of FIGS. 20-22, FIG. 28, FIG. 30, FIG. 33, and FIG. 38 being realized specifically using hardware resources, computer programs showing the processing procedures in the flowcharts form an invention in their own right. Although all of the embodiments show embodiments that relate to the implementation of computer programs pertaining to the present invention in an incorporated form in the playback devices, the computer programs shown in embodiments 1 to 6 may be implemented in their own right, separate from the playback devices. The implementation of the computer programs in there own right includes acts that involve: (1) production of the programs, (2) transference of the programs, either gratuitous or otherwise, (3) lending of the programs, (4) importing of the programs, (5) providing the programs publicly via bi-directional electronic communications circuits, and (6) approaching the general user about transfer, rental and the like by means of show-widow displays, catalogue solicitation, pamphlet distribution, and so forth.

(D) Consider that the element of "time" relating to the steps executed in time-series in the flowcharts of FIGS. 20-22, FIG. 28, FIG. 30, FIG. 33, and FIG. 38 is a required item for specifying the invention. If this is the case, then the processing procedures shown by the flowcharts can be understood as disclosing the usage configurations of the playback method. Execution of the processing in the flowcharts so as to achieve the original objects of the present invention and to enact the actions and effects by performing the processing of the steps in time-series is, needless to say, an implementation of the recording method pertaining to the present invention.

(E) With embodiment 5, Menus (ChapterMenu) for displaying lists of Chapters and MOVIE objects for controlling the behavior of these Menus may be recorded on a BD-ROM, and branching enabled from the Top Menu. Also, these Menus may be called by the depressing of a Chapter key on a remote controller.

(F) When recording on a BD-ROM, extension headers preferably are appended to TS packets structuring AVClips. The extension headers, which are called TP_extra_header, include an "Arrival_Time_Stamp" and a "copy_permission_indicator", and have a 4-byte data length. TP_extra_header-attached TS packets (hereinafter, abbreviated to "EX-attached TS packet") are arranged into groups of 32 packets, and written into three sectors. Each group comprising 32 EX-attached TS packets is 6,144 bytes in length (=32×192), and matches the 6,144-byte size of three sectors (=2048×3). The grouping of 32 EX-attached TS packets contained in three sectors is referred to as an "Aligned Unit".

A playback device 200 transmits Aligned Units in transmission processing as described below, when used in a home network connected via IEEE1394. That is, a device on the side of the sender removes the TP_extra_header from each of the 32 EX-attached TS packets included in an Aligned Unit, and outputs the TS packets after encoding the TS packet body based on a DTCP standard. When outputting TS packets, isochronous packets are inserted between all adjacent TS packets. The positioning of isochronous packets is based on times shown in the Arrival_Time_Stamp in each TP_extra_header. Playback device 200 outputs a DTCP_Descriptor following the outputting of the TS packets. The DTCP_Descriptor shows a copy permissibility setting in each TP_extra_header. Here, if the DTCP_Descriptor is described so as to show "copy prohibited", TS packets will not be recorded on other devices when used in a home network connected via IEEE1394.

(G) Although digital streams recorded on a recording medium in the embodiments are AVClips, the digital streams may be VOBs (Video Objects) complying with a DVD-Video standard or a DVD-Video Recording standard. VOBs are program streams compliant with ISO/IEC13818-1 obtained by multiplexing video and audio streams. Also, video streams in AVClips may be MPEG-4 format, WMV format, or the like. Furthermore, audio streams may be a Linear-PCM format, Dolby-AC3 format, MP3 format, MPEG-AAC format, a Dts, or WMA (Windows media audio).

(H) In the structure of the playback devices, only the current dynamic scenario is stored in dynamic scenario memory 15 and only current stream management information and current PL information is stored in the static scenario memory 11. However, a plurality of scenarios, stream management information and PL information may be stored in advance, as with cache memory. By doing this, the time lag until reading this data from the BD-ROM can be shortened. Also, although BACKUP memory 14 saves the stored values of registers in stack form, when consideration is given to the relationship with memory size, it is realistic to arrange the stored values for saving on the one level.

(I) Movie works in the embodiments may be obtained by encoding analog video signals broadcast by analog broadcast, or may be stream data constituted from transport streams broadcast by digital broadcast.

Also, contents may be obtained by encoding analog/digital video signals recorded on videotape. Furthermore, contents may be obtained by encoding analog/digital video signals taken directly from a video camera. Alternatively, the contents may be digital copyrighted works distributed from a distribution server.

(J) Java module 17 may be a Java platform installed in a device in order to transmit satellite broadcasts. If Java module 17 is this Java platform, a playback device pertaining to the present invention shares processing as MHP-use STBs.

Furthermore, Java module 17 may be a Java platform installed in a device in order to perform mobile telephone processing controls. If Java module 17 is this Java platform, a playback device pertaining to the present invention shares processing as a mobile telephone.

Also, BROWSER module 18 may be computer-installed Browser software such as Microsoft's Internet Explorer, and the like.

(K) In the layer model shown in the drawings, Browser mode and MOVIE mode may be disposed over Java mode. Particularly because of the light burden on the playback device of the execution of control procedures based on dynamic scenarios, the interpretation of dynamic scenarios in MOVIE mode, and the like, no problems arise even when MOVIE mode is executed over Java mode. Also, when developing playback devices and movie works, operation assurance can be dealt with in a single mode.

Furthermore, Java mode processing may be executed only in Java mode, without providing three modes. As shown in embodiment 2, since playback controls synchronized with PL playback are possible even in Java mode, the necessity of providing MOVIE mode is removed. Furthermore, controls in dynamic scenario may be only MOVIE mode or only Browser mode.

INDUSTRIAL APPLICABILITY

Recording media and playback devices pertaining to the present invention are capable of imparting interactive controls on movie works, thus making it possible to supply the market with movie works having high added value and to invigorate the markets for movies, consumer appliances, and the like. As such, recording media and playback devices pertaining to the present invention are highly applicable in the movie and consumer appliance industries.

The invention claimed is:

1. A computer-readable medium comprising:
   video data;
   management information that stores at least one piece of playback path information of the video data; and
   a first MOVIE object and a second MOVIE object,
   wherein the first MOVIE object includes a control command for controlling the management information and attribute information for controlling execution of the first MOVIE object,
   the attribute information includes a resume flag indicating whether to resume the first MOVIE object when a transition has been made to the second MOVIE object during execution of the first MOVIE object and a resume call is then made during execution of the second MOVIE object.

2. The computer-readable medium of claim 1, wherein the second MOVIE object belongs to a menu title,
   the attribute information further includes a menu call mask flag indicating whether or not to mask a transition to the second MOVIE object during execution of the first MOVIE object, and
   the resume flag is valid when the menu call mask flag indicates that the transition to the second MOVIE object is not to be masked during execution of the first MOVIE object.

3. The computer-readable medium of claim 1, wherein a setting of whether or not to execute a resume according to the resume flag is made respectively for each of a plurality of titles, each title being composed of a scenario and a piece of playback path information.

4. The computer-readable medium of claim 1, wherein at least one of the first MOVIE object and the second MOVIE object is a dynamic scenario including dynamic playback control procedures for executing management information.

5. The computer-readable medium of claim 4, wherein the dynamic scenario includes one of a Java mode and a Browser mode, the Java mode being a playback mode for Java virtual machines, the Browser mode being a playback mode for browsers.

6. The computer-readable medium of claim 1, wherein the resume flag further indicates whether to resume the control command of the first MOVIE object when the transition has been made to the second MOVIE object during execution of the first MOVIE object and the resume call is then made during execution of the second MOVIE object.

7. The computer-readable medium of claim 1, further comprising:

another management information that stores at least one piece of playback path information of the video data, wherein the second MOVIE object includes another control command for controlling the another management information.

8. A playback device for playing back, in accordance with a scenario, video data recorded on a recording medium, comprising:

a module operable to interpret a control procedure shown in the scenario, a playback unit operable to play back the video data in accordance with the interpretation by the module; and a reception unit operable to receive a user operation during playback of the video data, wherein the recording medium has recorded thereon, management information that stores at least one piece of playback path information of the video data; and a first MOVIE object and a second MOVIE object, the first MOVIE object including a control command for controlling the management information and attribute information for controlling execution of the first MOVIE object, the attribute information including a resume flag, and when the resume flag is ON, the playback unit resumes execution of the first MOVIE object when a resume call is made during execution of the second MOVIE object, and when the resume flag is OFF, the playback unit does not resume execution of the first MOVIE object when a resume call is made during execution of the second MOVIE object.

9. The playback device of claim 8, wherein the second MOVIE object belongs to a menu title the attribute information further includes a menu call mask flag indicating whether or not to mask a transition to the second MOVIE object during execution of the first MOVIE object, and the resume flag is valid when the menu call mask flag indicates that the transition to the second MOVIE object is not to be masked during execution of the first MOVIE object.

10. The playback device of claim 8, wherein the playback unit executes control of whether or not to execute a resume respectively for each of a plurality of titles, each title being composed of a MOVIE object and a piece of playback path information.

11. The playback device of claim 8, wherein at least one of the first MOVIE object and the second MOVIE object is a dynamic scenario including dynamic playback control procedures for executing management information.

12. The playback device of claim 11, wherein the dynamic scenario includes one of a Java mode and a Browser mode, the Java mode being a playback mode for Java virtual machines, the Browser mode being a playback mode for browsers.

13. The playback device of claim 8, wherein the resume flag further indicates whether to resume the control command of the first MOVIE object when the transition has been made to the second MOVIE object during execution of the first MOVIE object and the resume call is then made during execution of the second MOVIE object.

14. The playback device of claim 8, wherein the recording medium further has recorded thereon:

another management information that stores at least one piece of playback path information of the video data, wherein the second MOVIE object includes another control command for controlling the another management information.

15. A recording method, comprising the steps of:

creating application data; and recording the created application data on a recording medium, wherein the application data includes video data, management information that stores at least one piece of playback path information of the video data, and a first MOVIE object and a second MOVIE object, the first MOVIE object including a control command for controlling the management information and attribute information for controlling execution of the first MOVIE object, the attribute information including a resume flag, and the resume flag indicating whether to resume the first MOVIE object when a transition has been made to a scenario of the second MOVIE object during execution of the first MOVIE object and a resume call is then made during execution of the second MOVIE object.

16. The recording method of claim 15, wherein at least one of the first MOVIE object and the second MOVIE object is a dynamic scenario including dynamic playback control procedures for executing management information.

17. The recording method of claim 16, wherein the dynamic scenario includes one of a Java mode and a Browser mode, the Java mode being a playback mode for Java virtual machines, the Browser mode being a playback mode for browsers.

18. The recording method of claim 15, wherein the resume flag further indicates whether to resume the control command of the first MOVIE object when the transition has been made to the second MOVIE object during execution of the first MOVIE object and the resume call is then made during execution of the second MOVIE object.

19. The recording method of claim 15, wherein the application data further includes:

another management information that stores at least one piece of playback path information of the video data, wherein the second MOVIE object includes another control command for controlling the another management information.

20. An integrated circuit for, in a playback device, executing control for playing back, in accordance with a scenario, video data recorded on a recording medium, comprising:

a module operable to interpret a control procedure shown in the scenario;

a playback unit operable to play back the video data in accordance with the interpretation by the module; and a reception unit operable to receive a user operation during playback of the video data, wherein the recording medium has recorded thereon management information that stores at least one piece of playback path information of the video data, and a first MOVIE object and a second MOVIE object, the first MOVIE object including a control command for controlling the management information and attribute information for controlling execution of the first MOVIE object, the attribute information including a resume flag, and when the resume flag is ON, the playback unit resumes execution of the first MOVIE object when a resume call is made during execution of the second MOVIE object, and when the resume flag is OFF, the playback unit does not resume execution of the first MOVIE object when a resume call is made during execution of the second MOVIE object.

21. The integrated circuit of claim 20, wherein at least one of the first MOVIE object and the second MOVIE object is a dynamic scenario including dynamic playback control procedures for executing management information.

22. The integrated circuit of claim 21, wherein the dynamic scenario includes one of a Java mode and a Browser mode, the Java mode being a playback mode for Java virtual machines, the Browser mode being a playback mode for browsers.

23. The integrated circuit of claim 20, wherein the resume flag further indicates whether to resume the control command of the first MOVIE object when the transition has been made to the second MOVIE object during execution of the first MOVIE object and the resume call is then made during execution of the second MOVIE object.

24. The integrated circuit of claim 20, wherein the recording medium further has recorded thereon:
- another management information that stores at least one piece of playback path information of the video data,
- wherein the second MOVIE object includes another control command for controlling the another management information.

25. A playback method for playing, in accordance with a scenario, video data recorded on a recording medium, comprising the steps of:
- interpreting a control procedure shown in the scenario;
- playing the video data in accordance with the interpretation; and
- receiving a user operation during playback of the video data,
- wherein the recording medium has recorded thereon
- management information that stores at least one piece of playback path information of the video data, and
- a first MOVIE object and a second MOVIE object,
- the first MOVIE object including a control command for controlling the management information and attribute information for controlling execution of the first MOVIE object,
- the attribute information including a resume flag, and
- when the resume flag is ON, the playback unit resumes execution of the first MOVIE object when a resume call is made during execution of the second MOVIE object, and when the resume flag is OFF, the playback unit does not resume execution of the first MOVIE object when a resume call is made during execution of the second MOVIE object.

26. The playback method of claim 25, wherein at least one of the first MOVIE object and the second MOVIE object is a dynamic scenario including dynamic playback control procedures for executing management information.

27. The playback method of claim 26, wherein the dynamic scenario includes one of a Java mode and a Browser mode, the Java mode being a playback mode for Java virtual machines, the Browser mode being a playback mode for browsers.

28. The playback method of claim 25, wherein the resume flag further indicates whether to resume the control command of the first MOVIE object when the transition has been made to the second MOVIE object during execution of the first MOVIE object and the resume call is then made during execution of the second MOVIE object.

29. The playback method of claim 25, wherein the recording medium further has recorded thereon:
- another management information that stores at least one piece of playback path information of the video data,
- wherein the second MOVIE object includes another control command for controlling the another management information.

* * * * *

UNITED STATES PATENT AND TRADEMARK OFFICE
CERTIFICATE OF CORRECTION

PATENT NO. : 7,542,659 B2 Page 1 of 1
APPLICATION NO. : 10/546052
DATED : June 2, 2009
INVENTOR(S) : Masayuki Kozuka et al.

It is certified that error appears in the above-identified patent and that said Letters Patent is hereby corrected as shown below:

In the Claims
Claims 2-7, 9-14, 16-24 and 26-29 were cancelled and should be removed.

Signed and Sealed this

Sixteenth Day of February, 2010

David J. Kappos
*Director of the United States Patent and Trademark Office*